US010501401B2

(12) United States Patent
Xiang et al.

(10) Patent No.: US 10,501,401 B2
(45) Date of Patent: Dec. 10, 2019

(54) PRODRUGS OF GAMMA-HYDROXYBUTYRIC ACID, COMPOSITIONS AND USES THEREOF

(71) Applicant: XW Laboratories Inc., Grand Cayman (KY)

(72) Inventors: Jia-Ning Xiang, Palo Alto, CA (US); Xuesong Xu, Wuhan (CN); Xuan Zhang, Wuhan (CN)

(73) Assignee: XW LABORATORIES INC., Grand Cayman (KY)

( * ) Notice: Subject to any disclaimer, the term of this patent is extended or adjusted under 35 U.S.C. 154(b) by 0 days.

(21) Appl. No.: 16/275,165

(22) Filed: Feb. 13, 2019

(65) Prior Publication Data

US 2019/0218168 A1 Jul. 18, 2019

Related U.S. Application Data

(63) Continuation of application No. 15/762,559, filed as application No. PCT/CN2016/099763 on Sep. 22, 2016.

(30) Foreign Application Priority Data

Sep. 23, 2015 (WO) ................. PCT/CN2015/090326
Aug. 31, 2016 (CN) .......................... 2016 1 0782104

(51) Int. Cl.
| | | |
|---|---|---|
| A61K 31/221 | (2006.01) |
| C07C 69/78 | (2006.01) |
| C07C 255/57 | (2006.01) |
| C07D 213/79 | (2006.01) |
| C07D 213/80 | (2006.01) |
| C07D 309/12 | (2006.01) |
| C07C 271/22 | (2006.01) |
| C07C 271/34 | (2006.01) |
| C07C 69/612 | (2006.01) |
| C07D 317/64 | (2006.01) |
| C07D 333/38 | (2006.01) |
| C07C 229/08 | (2006.01) |
| C07C 233/47 | (2006.01) |
| C07D 207/16 | (2006.01) |
| C07D 307/68 | (2006.01) |
| C07C 69/22 | (2006.01) |
| C07C 69/34 | (2006.01) |
| C07C 69/618 | (2006.01) |
| C07C 69/74 | (2006.01) |
| C07C 69/96 | (2006.01) |
| C07C 229/34 | (2006.01) |
| C07C 317/14 | (2006.01) |
| C07D 207/12 | (2006.01) |
| C07D 211/44 | (2006.01) |
| C07D 277/30 | (2006.01) |

(52) U.S. Cl.
CPC .............. *C07C 69/78* (2013.01); *C07C 69/22* (2013.01); *C07C 69/34* (2013.01); *C07C 69/612* (2013.01); *C07C 69/618* (2013.01); *C07C 69/74* (2013.01); *C07C 69/96* (2013.01); *C07C 229/08* (2013.01); *C07C 229/34* (2013.01); *C07C 233/47* (2013.01); *C07C 255/57* (2013.01); *C07C 271/22* (2013.01); *C07C 271/34* (2013.01); *C07C 317/14* (2013.01); *C07D 207/12* (2013.01); *C07D 207/16* (2013.01); *C07D 211/44* (2013.01); *C07D 213/79* (2013.01); *C07D 213/80* (2013.01); *C07D 277/30* (2013.01); *C07D 307/68* (2013.01); *C07D 309/12* (2013.01); *C07D 317/64* (2013.01); *C07D 333/38* (2013.01); *C07C 2601/08* (2017.05); *C07C 2601/14* (2017.05); *C07C 2601/16* (2017.05)

(58) Field of Classification Search
CPC ............................. A61K 31/22; A61K 31/221
USPC .................................................. 514/547, 551
See application file for complete search history.

(56) References Cited

U.S. PATENT DOCUMENTS

| | | | |
|---|---|---|---|
| 3,845,770 | A | 11/1974 | Theeuwes et al. |
| 3,916,899 | A | 11/1975 | Theeuwes et al. |
| 5,547,986 | A | 8/1996 | Tinti et al. |
| 6,458,772 | B1 | 10/2002 | Zhou et al. |
| 6,472,431 | B2 | 10/2002 | Cook et al. |
| 6,780,889 | B2 | 8/2004 | Cook et al. |
| 6,818,787 | B2 | 11/2004 | Gallop et al. |
| 6,974,802 | B2 | 12/2005 | Zhou et al. |
| 7,015,200 | B2 | 3/2006 | Mamelak et al. |
| 7,071,173 | B2 | 7/2006 | Zhou et al. |
| 7,262,219 | B2 | 8/2007 | Cook et al. |
| 7,668,730 | B2 | 2/2010 | Reardan et al. |
| 7,765,106 | B2 | 7/2010 | Reardan et al. |
| 7,765,107 | B2 | 7/2010 | Reardan et al. |

(Continued)

FOREIGN PATENT DOCUMENTS

| | | |
|---|---|---|
| CN | 1422278 A | 6/2003 |
| CN | 101511388 A | 8/2009 |

(Continued)

OTHER PUBLICATIONS

Ahn, King Chang et al. Hapten and Antibody Production for a Sensitive Immunoassay Determining a Human Urinary Metabolite of the Pyrethroid insecticide Perrnethrin. J. Agric. Food Chem. Jun. 25, 2004 (Jun. 25, 2004), No. 15, vol. 52, pp. 4583-4594.
Co-pending U.S. Appl. No. 15/762,559, filed Mar. 23, 2018.
PCT/CN2015/090326 International Search Report and Written Opinion dated Jan. 6, 2016.
PCT/CN2016/099763 International Search Report and Written Opinion dated Jan. 3, 2017.

(Continued)

*Primary Examiner* — Charanjit Aulakh
(74) *Attorney, Agent, or Firm* — Wilson Sonsini Goodrich & Rosati

(57) ABSTRACT

The present disclosure discloses prodrugs of gamma-hydroxybutyric acid as well as compositions and uses thereof.

30 Claims, No Drawings

(56) References Cited

U.S. PATENT DOCUMENTS

| | | | |
|---|---|---|---|
| 7,797,171 | B2 | 9/2010 | Reardan et al. |
| 7,825,238 | B2 | 11/2010 | Zhou et al. |
| 7,851,506 | B2 | 12/2010 | Cook et al. |
| 7,895,059 | B2 | 2/2011 | Reardan et al. |
| 8,263,650 | B2 | 9/2012 | Cook et al. |
| 8,324,275 | B2 | 12/2012 | Cook et al. |
| 8,410,304 | B2 | 4/2013 | Luchi et al. |
| 8,457,988 | B1 | 6/2013 | Reardan et al. |
| 8,461,197 | B2 | 6/2013 | Tung |
| 8,461,203 | B2 | 6/2013 | Cook et al. |
| 8,524,944 | B2 | 9/2013 | Levin et al. |
| 8,589,182 | B1 | 11/2013 | Reardan et al. |
| 8,591,922 | B1 | 11/2013 | Allphin et al. |
| 8,731,963 | B1 | 5/2014 | Reardan et al. |
| 8,759,394 | B2 | 6/2014 | Tung et al. |
| 8,772,306 | B1 | 7/2014 | Eller |
| 8,859,619 | B2 | 10/2014 | Cook et al. |
| 8,901,173 | B2 | 12/2014 | Allphin et al. |
| 8,952,029 | B2 | 2/2015 | Eller |
| 8,952,062 | B2 | 2/2015 | Cook et al. |
| 9,050,302 | B2 | 6/2015 | Eller |
| 9,051,261 | B2 | 6/2015 | Tung |
| 9,132,107 | B2 | 9/2015 | Allphin et al. |
| 9,309,182 | B2 | 4/2016 | Tung et al. |
| 9,486,426 | B2 | 11/2016 | Eller et al. |
| 9,539,330 | B2 | 1/2017 | Cook et al. |
| 9,555,017 | B2 | 1/2017 | Allphin et al. |
| 9,795,567 | B2 | 10/2017 | Rourke et al. |
| 9,815,763 | B2 | 11/2017 | Tung et al. |
| 10,040,748 | B2 | 8/2018 | Tung et al. |
| 10,195,168 | B2 | 2/2019 | Allphin et al. |
| 2002/0077334 | A1 | 6/2002 | Cook et al. |
| 2006/0210630 | A1 | 9/2006 | Liang et al. |
| 2011/0034727 | A1 | 2/2011 | Luchi et al. |
| 2011/0039929 | A1 | 2/2011 | Cook et al. |
| 2011/0119085 | A1 | 5/2011 | Reardan et al. |
| 2012/0020833 | A1 | 1/2012 | Cook et al. |
| 2013/0324759 | A1 | 12/2013 | Mamelak et al. |
| 2014/0249222 | A1 | 9/2014 | Eller |
| 2015/0073052 | A1 | 3/2015 | Cook et al. |
| 2016/0106680 | A1 | 4/2016 | Bhandari et al. |
| 2016/0154947 | A1 | 6/2016 | Reardan et al. |
| 2016/0180058 | A1 | 6/2016 | Reardan et al. |
| 2017/0049731 | A1 | 2/2017 | Eller |
| 2017/0224825 | A1 | 8/2017 | Cook et al. |
| 2018/0042855 | A1 | 2/2018 | Rourke et al. |
| 2018/0200210 | A1 | 7/2018 | Eller |
| 2018/0207117 | A1 | 7/2018 | Cundy et al. |
| 2019/0022042 | A1 | 1/2019 | Dill |

FOREIGN PATENT DOCUMENTS

| | | |
|---|---|---|
| CN | 102076342 A | 5/2011 |
| CN | 102850397 A | 1/2013 |
| CN | 103370289 A | 10/2013 |
| NZ | 549273 A | 12/2007 |
| WO | WO-9941275 A1 | 8/1999 |
| WO | WO-9951613 A1 | 10/1999 |
| WO | WO-02063299 A1 | 8/2002 |
| WO | WO-2004001055 A2 | 12/2003 |
| WO | WO-2006029155 A2 | 3/2006 |
| WO | WO-2006053186 A2 | 5/2006 |
| WO | WO-2009129350 A2 | 10/2009 |
| WO | WO-2009137717 A1 | 11/2009 |
| WO | WO-2010009433 A1 | 1/2010 |
| WO | WO-2010124046 A1 | 10/2010 |
| WO | WO-2011111027 A2 | 9/2011 |
| WO | WO-2011139271 A1 | 11/2011 |
| WO | WO-2012112492 A1 | 8/2012 |
| WO | WO-2013164316 A1 | 11/2013 |
| WO | WO-2014031840 A1 | 2/2014 |
| WO | WO-2014093791 A1 | 6/2014 |
| WO | WO-2014134380 A1 | 9/2014 |
| WO | WO-2014199316 A1 | 12/2014 |
| WO | WO-2015062640 A1 | 5/2015 |
| WO | WO-2015083129 A1 | 6/2015 |
| WO | WO-2015106175 A1 | 7/2015 |
| WO | WO-2017049470 A1 | 3/2017 |
| WO | WO-2017050259 A1 | 3/2017 |
| WO | WO-2018015563 A1 | 1/2018 |
| WO | WO-2018191221 A1 | 10/2018 |

OTHER PUBLICATIONS

Lee, Jae Koo et al. Development of an Immunoassay for the Residues of the Herbicide Bensulfuron-Methyl. J. Agric. Food Chem.Feb. 20, 2002 (Feb. 20, 2002), No. 7, vol. 50, pp. 1791-1803.

Stadlwieser, Josef et al. Combinatorial Solid-Phase Synthesis of Structurally Complex Thiazolylhydantoines. Angew. Chem. Int. Ed. Dec. 31, 1998 (Dec. 31, 1998), No. 10, vol. 37, pp. 1402-1404.

SciFinder. Mar. 12, 2019 (Mar. 12, 2019), CAS Registry No. 1822708-15-5.

SciFinder, Mar. 12, 2019 (Mar. 12, 2019) CAS Registry No. 81055-72-3, 128321-03-9.

Alderman, et al. A review of cellulose ethers in hydrophilic matrices for oral controlled-release dosage forms. Int. J. Pharm. Tech. Prod. Mfr 5.3 (1984): 1-9.

Bamba, et al. Release mechanisms in gelforming sustained release preparations. International Journal of Pharmaceutics. vol. 2, Issues 5-6, Jun. 1979, pp. 307-315.

During et al. Controlled release of dopamine from a polymeric brain implant: In vivo characterization. Ann. Neurol. 1989;25:351-356.

EP16848140.6 European Search Report dated Mar. 19, 2019.

Goodson, in Medical Applications of Controlled Release, Chapter 6: Dental Application. supra, vol. 2, pp. 115-138 (1984).

Greene, et al. Protective Groups in Organic Synthesis. John Wiley & Sons, New York, NY, (3rd Edition, 1999).

Haralambidis, et al., The synthesis of polyamide-oligonucleotide conjugate molecules. Nucleic Acids Research, 1990; vol. 18, No. 3: 493-498.

Howard, et al. Intracerebral drug delivery in rats with lesion-induced memory deficits. J Neurosurg. Jul. 1989;71(1):105-12.

Langer, et al. Medical Applications of Controlled Release. CRC Press, Boca Raton, 1974.

Langer. New methods of drug delivery. Science, New Series, vol. 249, No. 4976 (Sep. 28, 1990), pp. 1527-1533.

Levy, et al. Inhibition of calcification of bioprosthetic heart valves by local controlled-release diphosphonate. Science. Apr. 12, 1985;228(4696):190-2.

Ranger and Peppas, J., Macromol. Sci. Rev. Macromol. Chem. 23:61 (1983).

Remington's Pharmaceutical Sciences, Mack Pub. Co., New Jersey (1991).

Smolen, et al. Controlled Drug Bioavailability. vol. 1, Drug Product Design and Performance (1984).

Blom et al., Preparative LC-MS Purification: Improved Compound specific method optimization. J. Combi. Chem. 2004, 6(6), 874-883.

U.S. Appl. No. 15/762,559 Office Action dated May 17, 2019.

Verma, et al. Osmotically controlled oral drug delivery. Drug Dev Ind Pharm. Jul. 2000;26(7):695-708.

Alshaikh, et al., Sodium oxybate for narcolepsy with cataplexy: Systematic review and meta-analysis. Journal of clinical sleep medicine. 2012; 8(4): 451-458.

Berner, J.E., A case of sodium oxybate treatment of tardive dyskinesia and bipolar disorder. J. Clinical psychiatry, May 2008; 69: 862-867.

EP16848140.6 European Search Report dated Jun. 25, 2019.

Khatami, et al., Long-term efficacy of sodium oxybate in 4 patients with chronic cluster headache. Neurology, Jul. 5, 2011; 77: 67-70.

Klein, et al., γ-Hydroxybutyrate (Xyrem) ameliorates clinical symptoms and neuropathology in a mouse model of Alzheimer disease. Neurobiology of Aging, 2015; 36: 832-844.

Ondo, et al., Sodium Oxybate for Excessive Daytime Sleepiness in Parkinson Disease. Arch Neurol. 2008; 65(10): 1337-1340.

Shneerson, J.M., Successful treatmnent of REM sleep behavior disorder with sodium oxybate. Clin. Neuropharm 2009; 32: 158-159.

(56) References Cited

OTHER PUBLICATIONS

Spitzer, et al., Treatment of the Narcoleptiform Sleep Disorder in Chronic Fatigue Syndrome and Fibromyalgia with Sodium Oxybate. World Institute of Pain. 2010; 10(1): 54-59.
Staud, R., Sodium oxybate for the treatment of fibromyalgia. Expert Opin. Pharmacother., 2011; 12(11): 1789-1798.
U.S. Appl. No. 15/762,559 Notice of Allowance dated Aug. 19, 2019.

PRODRUGS OF GAMMA-HYDROXYBUTYRIC ACID, COMPOSITIONS AND USES THEREOF

CROSS-REFERENCE

This application is a continuation of U.S. patent application Ser. No. 15/762,559, filed Mar. 23, 2018, which is a 371 U.S. National Stage Application of PCT Application No. PCT/CN2016/099763, filed Sep. 22, 2016, which claims the benefit of PCT Application No. PCT/CN2015/090326, filed Sep. 23, 2015, and further claims benefit of Chinese Patent Application No. 201610782104.1, filed Aug. 31, 2016; the entire contents of each of which are incorporated herein by reference.

FIELD OF THE INVENTION

The present disclosure generally relates to prodrugs of gamma-hydroxybutyric acid (GHB), as well as compositions and uses thereof.

BACKGROUND OF THE INVENTION

Narcolepsy is a chronic neurological disorder characterized by excessive daytime sleepiness (EDS), cataplexy, sleep paralysis, hypnagogic hallucinations, and disturbed nocturnal sleep. EDS is usually present and appears first. Cataplexy occurs in approximately 70% of patients with narcolepsy while the other symptoms feature less frequently and in various combinations. The prevalence of narcolepsy in the United States and Europe ranges from 20 to 67 per 100,000.

GHB is a naturally-occurring central nervous system (CNS) transmitter. The GHB sodium salt also called sodium oxybate, currently being marketed by Jazz Pharmaceuticals plc as Xyrem, is the first and only drug approved by the U.S. Food and Drug Administration (FDA) to treat cataplexy associated with narcolepsy. Sodium oxybate has been shown to be highly efficacious with a ~70% reduction of the total number of cataplexy episodes. In Europe, sodium oxybate is used medicinally for various purposes including narcolepsy, alcohol dependence, and opiate dependence. In November 2005, the FDA approved an expanded indication for sodium oxybate as a treatment for excessive daytime sleepiness (EDS). In addition, sodium oxybate has also been conducted in the clinical trial in the U.S. for fibromyalgia syndrome, a pain of fibromyalgia that is notoriously difficult to treat. Sodium oxybate also has potential to treat other CNS disorders such as insomnia, hallucinogenic dreams and sleep paralysis.

Despite its efficacious effect and advantageous position in treating EDS and cataplexy associated with narcolepsy, sodium oxybate displays a sub-optimal pharmacokinetics profile that makes it difficult to provide optimal therapeutic benefits. The deficiencies of sodium oxybate include: 1) variable oral bioavailability and unpredictable drug plasma concentrations resulting from its erratic absorption in patients; 2) short plasma half-life ($t_{1/2}$<1 hr); 3) significant food effect (high fat meal may significantly delay and decrease absorption of sodium oxybate); 4) high bolus oral dosing caused unpleasant GI disturbance; 5) poor patient compliance and inconvenient drug administration (due to the twice per night dosage regimen), 6) risk of hypernatremia (due to intake of large amount of sodium salt form compounds). Consequently, these deficiencies prevent sodium oxybate from providing the maximum therapeutic benefit that it can possibly achieve. Therefore, there remains a continuing need for compounds derived from GHB to overcome some or all of the above described deficiencies.

SUMMARY OF THE INVENTION

The present disclosure provides, inter alia, a compound of Formula I:

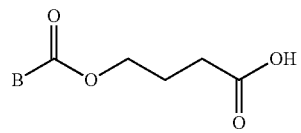

Formula (I)

or a pharmaceutically acceptable salt, ester, hydrate, or solvate thereof, wherein the variables are defined below.

The present disclosure further provides a pharmaceutical composition comprising one or more compounds of the present disclosure.

The present disclosure also provides use of one or more compounds in the manufacture of a medicament for treating a disease, wherein the disease is narcolepsy, excessive daytime sleepiness, cataplexy, neurodegenerative disease, sleep disturbance syndrome, fibromyalgia, chronic fatigue, schizophrenia, binge eating disorder, Parkinson disease, tardive dyskinesia, or Alzheimer's disease.

The present disclosure further provides a method of treating a disease, comprising administering to a subject an effective amount of one or more compounds of the present disclosure, wherein the disease is narcolepsy, excessive daytime sleepiness, cataplexy, neurodegenerative disease, sleep disturbance syndrome, fibromyalgia, chronic fatigue, schizophrenia, Binge eating disorder, Parkinson disease, tardive dyskinesia, or Alzheimer's disease.

The present disclosure also provides a compound of the present disclosure for use in any of the methods described herein.

DETAILED DESCRIPTION OF THE INVENTION

Compound

In one aspect, the present disclosure provides a compound of Formula I:

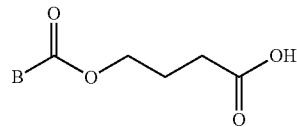

Formula (I)

or a pharmaceutically acceptable salt, ester, hydrate, or solvate thereof, wherein, B is

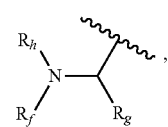

—(O)R$^1$, —R$^2$(OCO)R$^3$, substituted or unsubstituted C$_{5-10}$ aryl, C$_{1-12}$ alkyl, C$_{5-12}$ aralkyl, C$_{2-12}$ alkenyl, C$_{6-12}$ aralkenyl, C$_{2-12}$ alkynyl, C$_{3-8}$ cycloalkyl, 3-10 membered heterocyclic alkyl, or 5-10 membered heterocyclic aryl, wherein the one or more substituents are selected from the group consisting of C$_{1-12}$ alkyl, amino, substituted amino, amino protecting group, —R$^4$—S—R$^5$, halogen, hydroxyl, cyano, mono-, di- or tri-halo-C$_{1-6}$ alkyl, C$_{2-12}$ alkenyl, C$_{2-12}$ alkynyl, C$_{1-12}$ alkoxy, C$_{5-10}$ aryl, C$_{5-10}$ alkylaryl, C$_{3-8}$ cycloalkyl, C$_{1-12}$ alkylsulfonyl, 3-8 membered heterocyclic alkyl, 3-10 membered heterocyclic aryl, C$_{5-10}$ aryloxyl, C$_{5-10}$ arylcarbonyl, C$_{1-6}$ alkylcarbonyloxyl or C$_{1-4}$ alkyloxycarbonyl;

wherein

R$^1$ and R$^3$ are independently C$_{1-12}$ alkyl, C$_{2-12}$ alkenyl, C$_{1-12}$ aralkyl, C$_{6-12}$ aralkenyl, C$_{2-12}$ alkynyl, C$_{5-10}$ aryl, C$_{3-8}$ cycloalkyl, 3-10 membered heterocyclic alkyl, 5-10 membered heterocyclic aryl, or

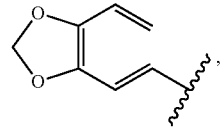 [SMILES: */C=C/C1=C(C=C)OCO1]

any of which can be optionally mono- or independently multi-substituted by —R$^4$—S—R$^5$, halogen, hydroxyl, cyano, amino, substituted amino, C$_{1-12}$ alkyl, C$_{2-12}$ alkenyl, C$_{2-12}$ alkynyl, C$_{5-10}$ aryl, C$_{1-12}$ alkoxy, C$_{3-8}$ cycloalkyl, 3-8 membered heterocyclic alkyl, or 3-10 membered heterocyclic aryl, C$_{1-4}$ alkylsulfonyl, C$_{5-10}$ aryloxyl, C$_{5-10}$ to arylcarbonyl, C$_{1-4}$ alkyloxycarbonyl, or C$_{1-12}$ alkylcarbonylamino;

R$^2$ is C$_{1-6}$ alkylene or C$_{1-6}$ alkyleneoxyl, any of which is optionally further substituted with C$_{1-6}$ alkyl;

R$^4$ is a bond, C$_{1-6}$ alkylene, C$_{5-10}$ arylene, or C$_{5-12}$ arylenealkylene, any of which is optionally further substituted with C$_{1-3}$ alkyl, and R$^5$ is hydrogen or C$_{1-12}$ alkyl, R$_g$ is hydrogen, C$_{1-6}$ alkyl, phenyl, or phenylmethyl, any of which is optionally mono- or independently multi-substituted by halogen, hydroxyl, methylthio, C$_{1-4}$ alkyl, or C$_{5-8}$ aryl; and R$_h$ and R$_f$ are independently hydrogen, C$_{1-6}$ alkyl, C$_{1-6}$ alkylcarbonyl, C$_{1-6}$ alkoxylcarbonyl, C$_{3-6}$ cycloalkoxylcarbonyl, or an amino protecting group;

or

R$_f$ and R$_g$ together with C, O, N or S atom form a 4-8 membered heterocyclic alkyl or

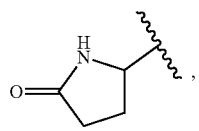 [SMILES: *C1CCC(=O)N1]

any of which is optionally mono- or independently multi-substituted by halogen, hydroxyl or C$_{1-4}$ alkyl, and R$_h$ is hydrogen, C$_{1-6}$ alkyl or an amino protecting group.

In some embodiments, B is C$_{1-8}$ alkyl substituted with C$_{2-6}$ alkyl, aryl or amino group and B is not linear alkyl. In some embodiments, B is C$_{2-6}$ alkenyl substituted with C$_{1-6}$ alkyl, aryl or amino group. In some embodiments, B is substituted or unsubstituted C$_{3-8}$ cycloalkyl, wherein the substituent is selected from the group consisting of halogen, hydroxyl and C$_{1-6}$ alkyl. In some embodiments, B is substituted or unsubstituted 3-8 membered heterocyclic alkyl, wherein the substituent is selected from the group consisting of halogen, hydroxyl and C$_{1-6}$ alkyl. In some embodiments, B is substituted or unsubstituted 5-8 membered heterocyclic aryl, wherein the substituent is selected from the group consisting of halogen, hydroxyl and C$_{1-6}$ alkyl.

In some embodiments, B is —CHR$^{13}$R$^{14}$, wherein R$^{13}$ and R$^{14}$ are independently selected from the group consisting of hydrogen, C$_{1-6}$ alkyl, C$_{5-10}$ aryl and amino group, wherein R$^{13}$ and R$^{14}$ cannot be methyl at the same time. In some embodiments, R$^{13}$ and R$^{14}$ can be cyclized to form a C$_{3-8}$ cycloalkyl. In some embodiments, R$^{13}$ and R$^{14}$ together with a O, N or S atom form a 3-8 membered heterocyclic alkyl.

The present disclosure also provides a compound having the chemical structure shown in Formula (IA):

Formula (IA)

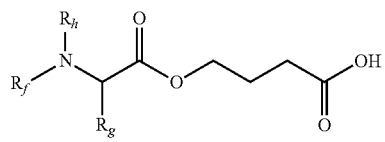

or a pharmaceutically acceptable salt, ester, hydrate, or solvate thereof, wherein, R$_g$ is hydrogen, C$_{1-6}$ alkyl, phenyl, or phenylmethyl, any of which is optionally mono- or independently multi-substituted by halogen, hydroxyl, methylthio, C$_{1-4}$ alkyl, or C$_{5-8}$ aryl; and R$_h$ and R$_f$ are independently hydrogen, C$_{1-6}$ alkyl, C$_{1-6}$ alkylcarbonyl, C$_{1-6}$ alkoxylcarbonyl, C$_{3-6}$ cycloalkoxylcarbonyl or an amino protecting group.

In some embodiments, R$_g$ is hydrogen or C$_{1-3}$ alkyl. In some embodiments, at least one of R$_h$ and R$_f$ is hydrogen or C$_{1-3}$ alkyl. In some embodiments, both R$_h$ and R$_f$ are hydrogen or C$_{1-3}$ alkyl. In some embodiments, R$_h$ is hydrogen or C$_{1-3}$ alkyl and R$_f$ is —COR$^5$, and R$^5$ is C$_{1-3}$ alkyl, C$_{1-3}$ alkoxyl, or C$_{5-6}$ cycloalkyloxyl. In some embodiments, when R$_f$ or R$_h$ is an amino protecting group, R$_g$ is not isopropyl or benzyl.

The present disclosure also provides a compound having the chemical structure shown in Formula (IA):

Formula (IA)

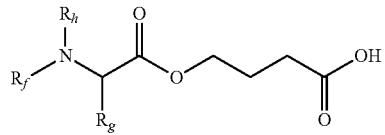

or a pharmaceutically acceptable salt, ester, hydrate, or solvate thereof, wherein, R$_f$ and R$_g$ together with C, O, or N atom form a 4-6 membered heterocyclic alkyl or

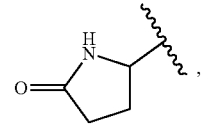 [SMILES: *C1CCC(=O)N1]

any of which is optionally mono- or independently multi-substituted by halogen, hydroxyl, C$_{1-4}$ alkyl or an amino protecting group;

R$_h$ is hydrogen, C$_{1-3}$ alkyl or an amino protecting group.

The present disclosure also provides a compound having the chemical structure shown in Formula (IA-1):

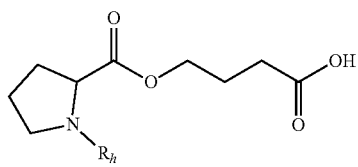

Formula (IA-1)

or a pharmaceutically acceptable salt, ester, hydrate, or solvate thereof, wherein, $R_h$ is hydrogen, $C_{1-3}$ alkyl or an amino protecting group.

The present disclosure also provides a compound having the chemical structure shown in Formula (IA-2):

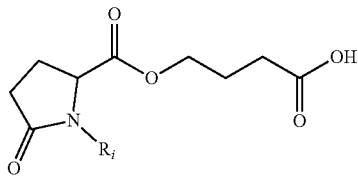

Formula (IA-2)

or a pharmaceutically acceptable salt, ester, hydrate, or solvate thereof, wherein, $R_i$ is hydrogen, $C_{1-4}$ alkyl or an amino protecting group.

The present disclosure also provides a compound having the chemical structure shown in Formula (IB):

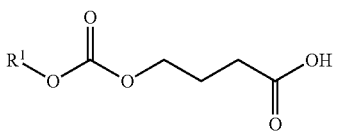

Formula (IB)

or a pharmaceutically acceptable salt, ester, hydrate, or solvate thereof, wherein, $R^1$ is $C_{1-8}$ alkyl, $C_{5-8}$ aryl, $C_{5-12}$ aralkyl, 3-10 membered heterocyclic alkyl or

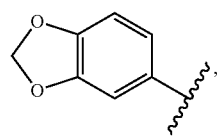

any of which is optionally mono- or independently multi-substituted by halogen, cyano, hydroxyl, $C_{1-12}$ alkyl or $C_{1-4}$ alkoxy.

In some embodiments, $R^1$ is

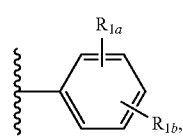

and wherein $R_{1a}$ and $R_{1b}$ are independently hydrogen, $C_{1-12}$ alkyl, $C_{1-4}$ alkoxy or halogen. In some embodiments, $R^1$ is

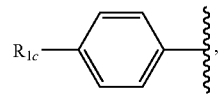

and $R_{1c}$ is hydrogen, $C_{1-12}$ alkyl or halogen.

The present disclosure also provides a compound having the chemical structure shown in Formula (IC):

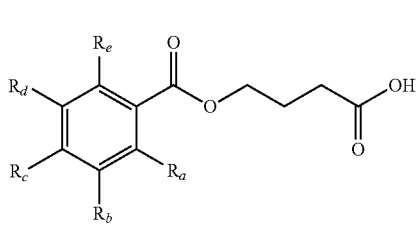

Formula (IC)

or a pharmaceutically acceptable salt, ester, hydrate, or solvate thereof, wherein, $R_a$, $R_b$, $R_c$, $R_d$ and $R_e$ are independently hydrogen, halogen, $C_{1-12}$ alkyl, $C_{1-12}$ alkoxy, cyano, $C_{1-12}$ alkylsulfonyl, $C_{1-6}$ alkylcarbonyloxyl, $C_{1-4}$ alkyloxycarbonyl, mono-, di- or tri-halo-$C_{1-6}$ alkyl, $C_{5-10}$ aryloxyl or $C_{5-10}$ arylcarbonyl; and when $R_a$, $R_b$, $R_c$, $R_d$ and $R_e$ are all hydrogen, at least one of $R_a$, $R_b$, $R_c$, $R_d$ and $R_e$ is not protium.

In some embodiments, $R_b$, $R_c$, $R_d$ are all hydrogen, and $R_e$ and $R_a$ are independently hydrogen, halogen, $C_{1-3}$ alkyl, $C_{1-3}$ alkoxy, cyano, $C_{1-3}$ alkylsulfonyl, $C_{1-3}$ alkylcarbonyloxyl, $C_{1-3}$ alkyloxycarbonyl, or mono-, di- or tri-halo-$C_{1-3}$ alkyl. In some embodiments, one of $R_e$ and $R_a$ is hydrogen. In some embodiments, not all of $R_a$, $R_b$, $R_c$, $R_d$ and $R_e$ are hydrogen at the same time.

The present disclosure also provides a compound having the chemical structure shown in Formula (ID):

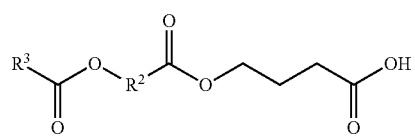

Formula (ID)

or a pharmaceutically acceptable salt, ester, hydrate, or solvate thereof, wherein, $R^2$ is $-(CR^6R^7)_m-$, wherein m=1-6 and $R^6$ and $R^7$ are independently hydrogen or $C_{1-3}$ alkyl;

$R^3$ is $C_{1-12}$ alkyl, $C_{5-8}$ aryl, 3-8 membered heterocyclic alkyl, or 5-8 membered heterocyclic aryl, which are each optionally mono- or independently multi-substituted by halogen, unsubstituted or substituted amino, $C_{1-6}$ alkyl or $C_{1-6}$ alkoxy; wherein when the amino is substituted it can be optionally mono- or independently multi-substituted by $C_{1-6}$ alkyl, or $C_{1-6}$ alkylcarbonyl.

In some embodiment, $R^2$ is $-CH_2-$. In some embodiment, $R^3$ is methyl, ethyl, phenyl, which are each optionally mono- or independently multi-substituted by methoxyl, methyl or ethyl.

The present disclosure also provides a compound having the chemical structure shown in Formula (ID-1):

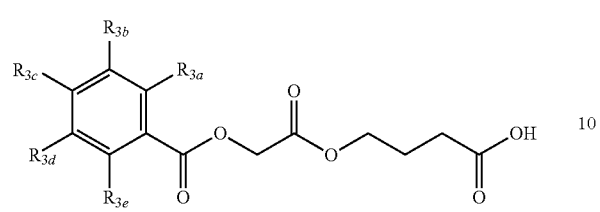

Formula (ID-1)

or a pharmaceutically acceptable salt, ester, hydrate, or solvate thereof, wherein, $R_{3a}$, $R_{3b}$, $R_{3c}$, $R_{3d}$ and $R_{3e}$ are independently hydrogen, halogen, $C_{1-6}$ alkyl, or $C_{1-6}$ alkoxy.

The present disclosure also provides a compound having the chemical structure shown in Formula (ID-2):

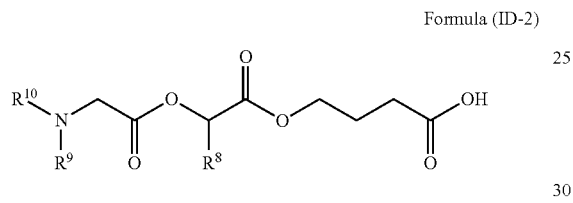

Formula (ID-2)

or a pharmaceutically acceptable salt, ester, hydrate, or solvate thereof, wherein, $R^9$ and $R^{10}$ are independently hydrogen, $C_{1-6}$ alkyl or $C_{1-6}$ alkylcarbonyl; and $R^8$ is hydrogen or $C_{1-6}$ alkyl.

The present disclosure also provides a compound having the chemical structure shown in Formula (IE):

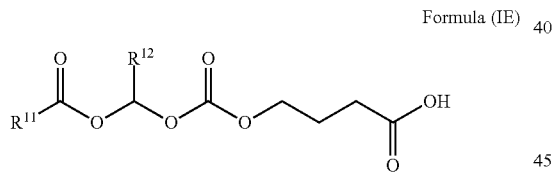

Formula (IE)

or a pharmaceutically acceptable salt, ester, hydrate, or solvate thereof, wherein, $R^{11}$ is $C_{1-8}$ alkyl or $C_{5-8}$ aryl, any of which is optionally mono- or independently multi-substituted by halogen, hydroxyl, $C_{1-6}$ alkyl or $C_{1-4}$ alkoxy;

$R^{12}$ is hydrogen or $C_{1-6}$ alkyl.

In some embodiments, the molecular weight of each of the compounds disclosed herein is no more than 450 Da. In some embodiments, the molecular weight of each of the compounds disclosed herein is 150-450 Da, 150-300 Da, or 200-300 Da.

In some embodiments, the compound is selected from:

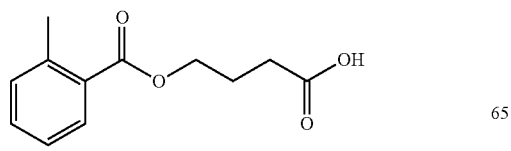

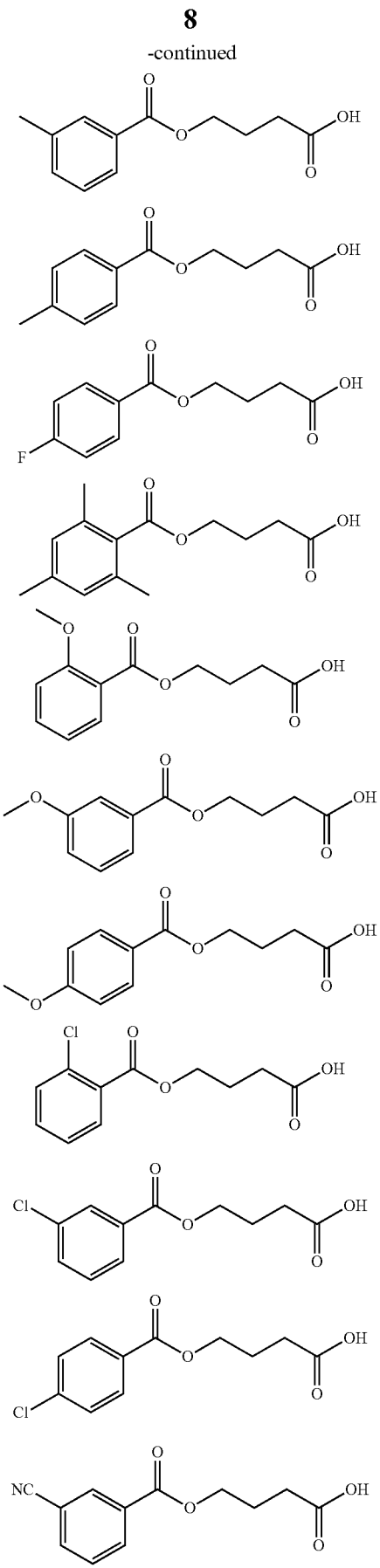

-continued
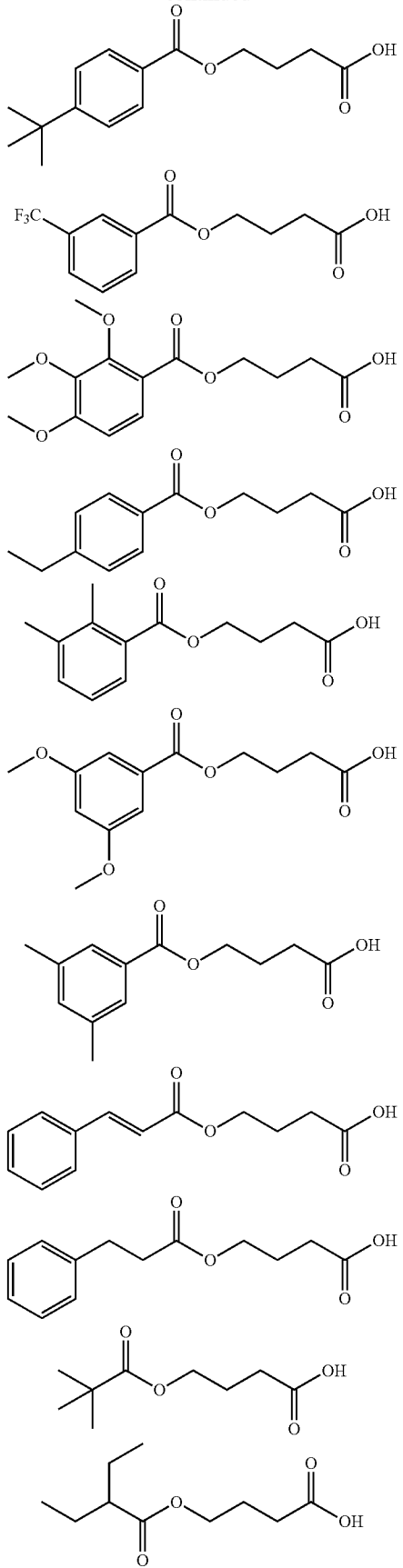
-continued
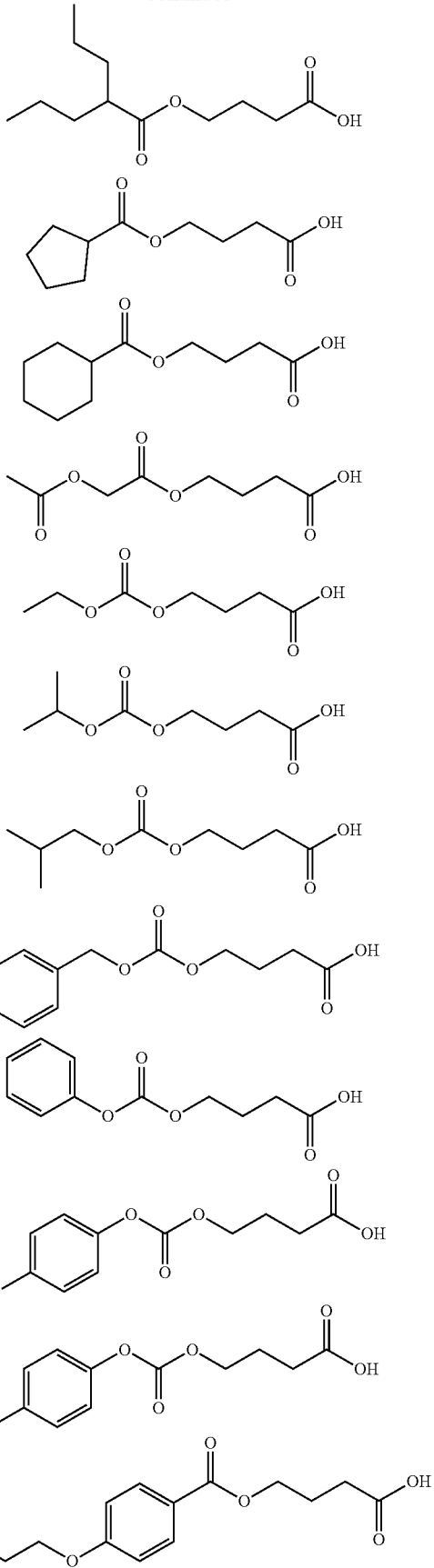

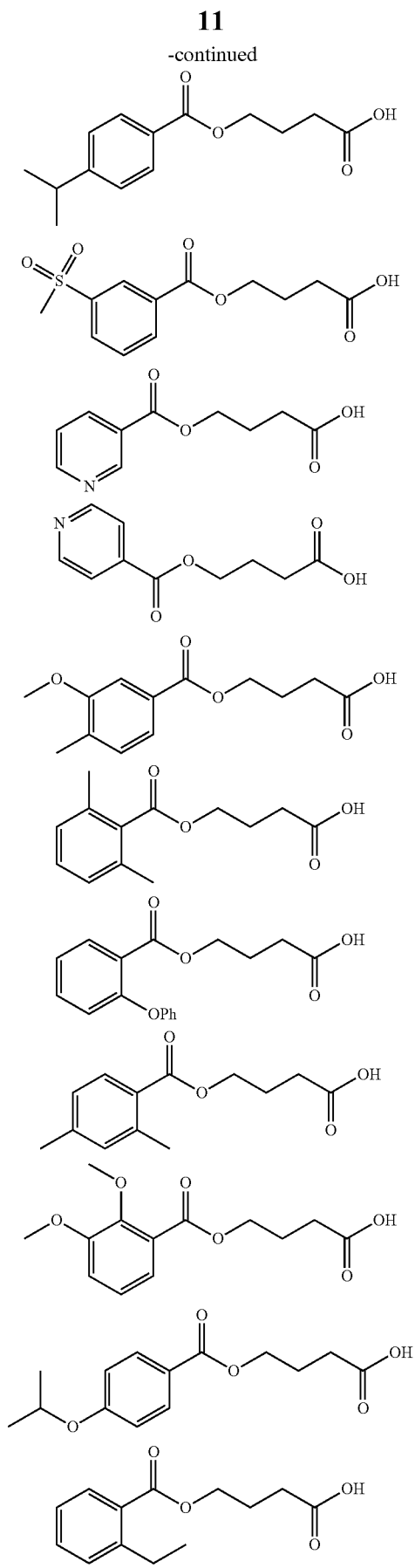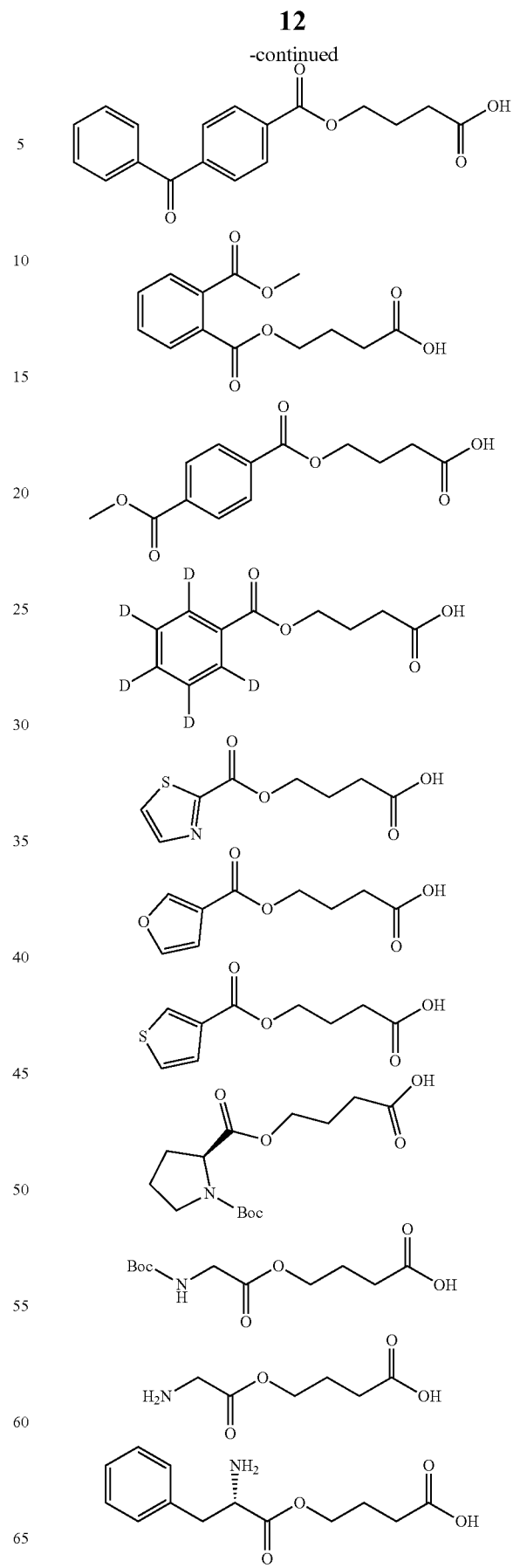

13
-continued
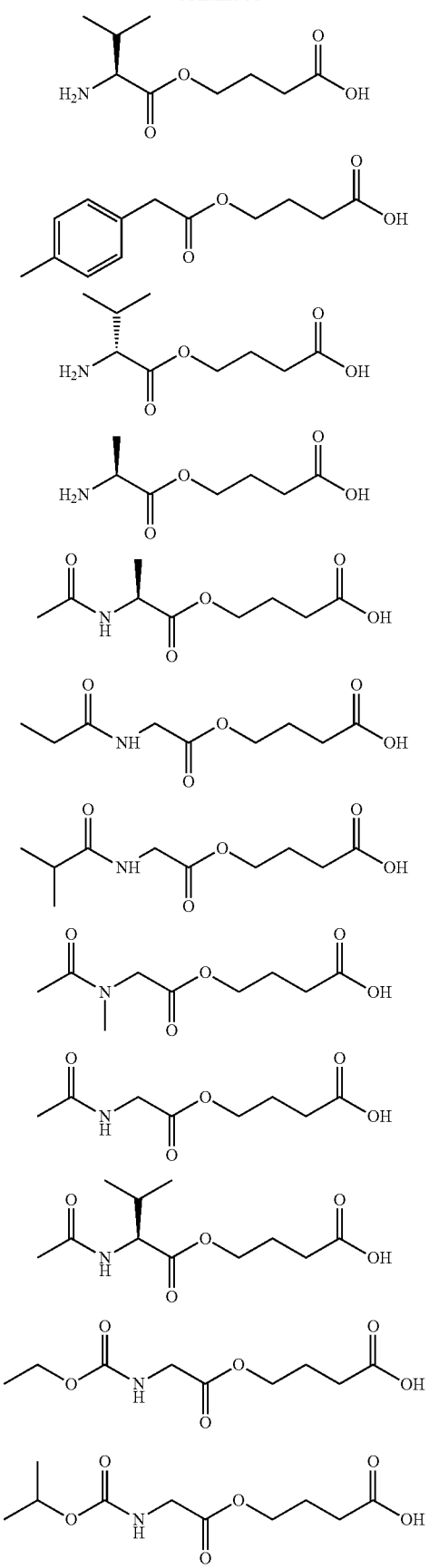
14
-continued
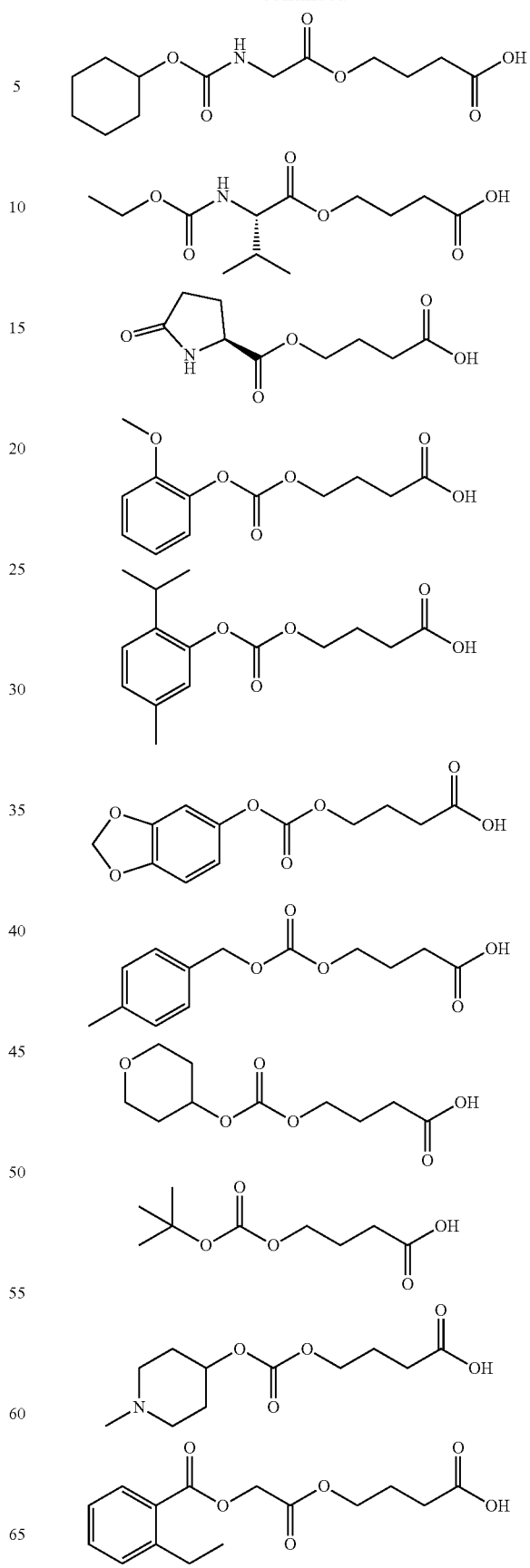

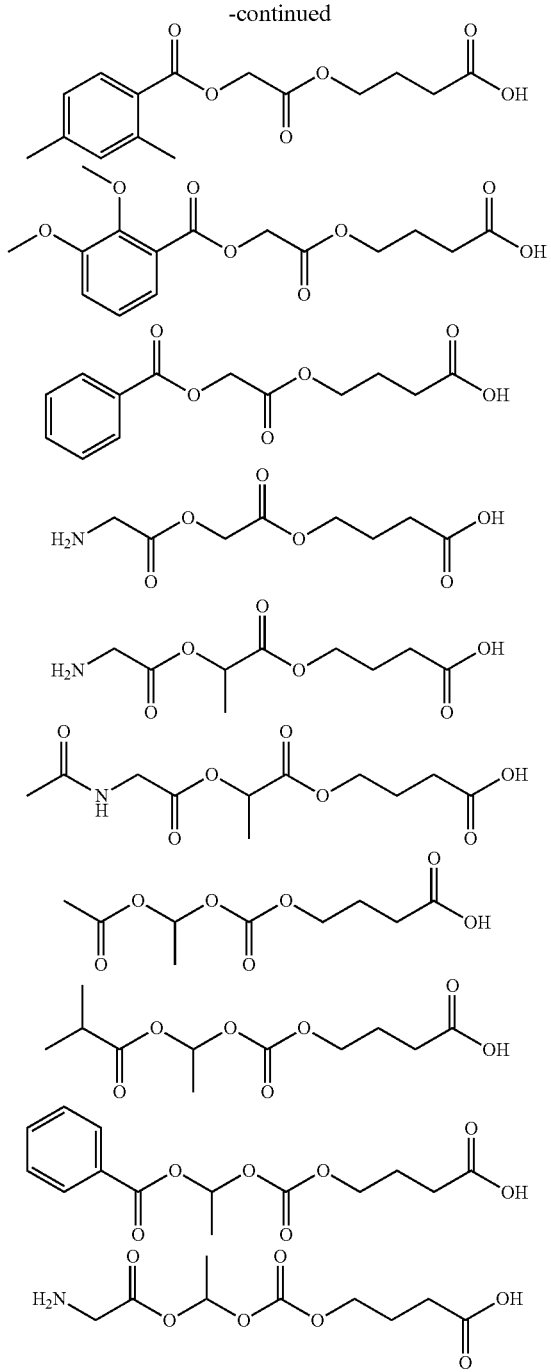

Various features of the present disclosure that are, for brevity, described in the context of a single embodiment, can also be provided separately or in any suitable subcombination.

As used herein, the term "substituted", when refers to a chemical group, means the chemical group has one or more hydrogen atoms that is/are removed and replaced by substituents. As used herein, the term "substituent" has the ordinary meaning known in the art and refers to a chemical moiety that is covalently attached to, or if appropriate fused to, a parent group. As used herein, the term "optionally substituted" means that the chemical group may have no substituents (i.e. unsubstituted) or may have one or more substituents (i.e. substituted). It is to be understood that substitution at a given atom is limited by valency.

As used herein, the term "$C_{n-m}$" indicates a range of the carbon atoms numbers, wherein n and m are integers and the range of the carbon atoms numbers includes the endpoints (i.e. n and m) and each integer point in between. For examples, $C_{1-6}$ indicates a range of one to six carbon atoms, including one carbon atom, two carbon atoms, three carbon atoms, four carbon atoms, five carbon atoms and six carbon atoms.

As used herein, the term "alkyl", whether as part of another term or used independently, refers to a saturated hydrocarbon group that may be straight-chain or branched-chain. The term "$C_{n-m}$ alkyl" refers to an alkyl having n to m carbon atoms. In some embodiments, the alkyl group contains 1 to 12, 1 to 8, 1 to 6, 1 to 4, 1 to 3, or 1 to 2 carbon atoms. Examples of alkyl group include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like.

As used herein, the term "alkenyl", whether as part of another term or used independently, refers to an unsaturated hydrocarbon group that may be straight-chain or branched-chain having at least one carbon-carbon double bond. The term "$C_{n-m}$ alkenyl" refers to an alkenyl having n to m carbon atoms. In some embodiments, the alkenyl group contains 2 to 12, 2 to 10, 2 to 8, 2 to 6, 2 to 5, 2 to 4, or 2 to 3 carbon atoms. In some embodiments, the alkenyl group contains 1 to 6, 1 to 5, 1 to 4, 1 to 3, 1 to 2, or 1 carbon-carbon double bond. Examples of alkenyl groups include, but are not limited to, chemical groups such as ethenyl, n-propenyl, isopropenyl, n-butenyl, sec-butenyl, and the like.

As used herein, the term "alkynyl", whether as part of another term or used independently, refers to an unsaturated hydrocarbon group that may be straight-chain or branched-chain having at least one carbon-carbon triple bonds. The term "$C_{n-m}$ alkynyl" refers to an alkynyl having n to m carbon atoms. In some embodiments, the alkynyl group contains 2 to 12, 2 to 10, 2 to 8, 2 to 6, 2 to 5, 2 to 4, or 2 to 3 carbon atoms. In some embodiments, the alkynyl group contains 1 to 6, 1 to 5, 1 to 4, 1 to 3, 1 to 2, or 1 carbon-carbon triple bond. Examples of alkynyl groups include, but are not limited to, chemical groups such as ethynyl, propyn-1-yl, propyn-2-yl, and the like.

As used herein, the term "alkylene", whether as part of another term or used independently, refers to a bivalent saturated hydrocarbon moieties which is linear, or branched, and which connects two other parts of a molecule. The term "$C_{n-m}$ alkylene" refers to an alkylene having n to m carbon atoms. In some embodiments, the alkylene group contains 1 to 12, 1 to 10, 1 to 8, 1 to 6, 1 to 5, 1 to 4, or 1 to 3 carbon atoms. Examples of alkylene groups include, but are not limited to, chemical groups such as methylene, ethylene, 1-methyl-methylene, propylidene, butylidene and the like.

As used herein, the term "aryl" or "aromatic", whether as part of another term or used independently, refers to a mono- or polycyclic carbocyclic ring system radicals with alternating double and single bonds between carbon atoms forming the rings. In some embodiments, the aryl ring systems have 5 to 10, 5 to 8, or 5 to 6 carbon atoms in one or more rings. In some embodiment, the aryl ring system have 2 or more rings fused together. Examples of aryl groups include, but are not limited to, chemical groups such as phenyl, naphthyl, tetrahydronaphthyl, indanyl, idenyl and the like.

As used herein, the term "arylene", whether as part of another term or used independently, refers to a divalent aryl ring or ring system which connects two other parts of a molecule, i.e. the two parts are bonded to the ring in two distinct ring positions. When the aryl ring of the arylene is a monocyclic ring system, the two parts are bonded to the same ring in two distinct ring positions. When the aryl ring of the arylene is a polycyclic ring system, the two parts can be bonded to the same ring or different rings in two distinct ring positions. Arylene may be substituted or unsubstituted. Unsubstituted arylene has no substituents other than the two parts of the molecule it connects. Substituted arylene has substituents in addition to the two parts of the molecule it connects.

As used herein, the term "aralkyl", whether as part of another term or used independently, refers to a group of formula -alkyl-aryl. The term "$C_{n-m}$ aralkyl" refers to aralkyl with a total carbon number between n to m. In some embodiments, the alkyl moiety has 1 to 6, 1 to 4, 1 to 3, or 1 to 2 carbon atoms. In some embodiments, the aralkyl group has 5-12, 5-10, 5-8, or 6-7 carbon atoms. Examples of aralkyl groups include, but are not limited to, various alkyl benzenes and alkyl naphthalenes.

As used herein, the term "arylenealkylene", whether as part of another term or used independently, refers to a group of formula -alkylene-arylene, wherein the arylene and alkylene groups are as previously described, wherein the term "$C_{n-m}$ arylenealkylene" refers to an arylenealkylene group with a total carbon number between n to m. In some embodiments, the alkylene portion of the arylenealkylene moiety has 1 to 6, 1 to 4, 1 to 3, or 1 to 2 carbon atoms. In some embodiments, the arylene portion of the arylenealkylene moiety has 6 to 12, 6 to 11, 6 to 10, 6 to 9, or 6 to 8 ring forming carbon atoms. In some embodiments, the arylenealkylene moiety has 7-12, 7-10, 7-9, or 7-8 carbon atoms.

As used herein, the term "aralkenyl", whether as part of another term or used independently, refers to a group of formula -alkenyl-aryl, wherein the term "$C_{n-m}$ aralkenyl" refers to an aralkenyl group with a total carbon number between n to m. In some embodiments, the alkenyl moiety contains 2 to 12, 2 to 10, 2 to 8, 2 to 6, 2 to 5, 2 to 4, or 2 to 3 carbon atoms. In some embodiments, the aralkenyl group has 6-18, 6-12, 6-10, 6-8, or 6-7 carbon atoms. Examples of aralkenyl groups include, but are not limited to, chemical groups such as styryl, 3-(benzyl) prop-2-enyl, and 6-napthylhex-2-enyl.

As used herein, the term "cycloalkyl", whether as part of another term or used independently, refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. In some embodiments, the cycloalkyl is saturated cycloalkyl. Cycloalkyl groups can have 3, 4, 5, 6, 7, 8 ring-forming carbons ($C_{3-8}$). Examples of cycloalkyl groups include, but are not limited to, chemical groups such as cyclopropyl, cyclobutyl, cyclopentyl, cyclohexyl, cycloheptyl, cyclopentenyl, cyclohexenyl, cyclohexadienyl, cycloheptatrienyl, and the like. In some embodiments, a cycloalkyl used herein may be fused (i.e., having a bond in common with) with one or more aromatic rings, for example, benzo or thienyl derivatives of cyclopentane, cyclohexane, and the like. In some embodiments, a cycloalkyl group containing a fused aromatic ring can be attached through any ring-forming atom including a ring-forming atom of the fused aromatic ring.

As used herein, the term "cycloalkylene", whether as part of another term or used independently, refers to a bivalent saturated or partially saturated non-aromatic cyclic hydrocarbons group, and which connects two other parts of a molecule. The term "$C_{n-m}$ cycloalkylene" refers to a cycloalkylene having n to m carbon atoms. In some embodiments, the cycloalkylene group contains 3 to 12, 3 to 10, 3 to 8, 3 to 7, 3 to 6, 3 to 5, or 3 to 4 carbon atoms. Examples of cycloalkylene groups include, but are not limited to, chemical groups such as cyclopropylidene, cyclobutalidene and the like.

As used herein, the term "alkoxy", whether as part of another term or used independently, refers to a group of formula —O-alkyl. The term "$C_{n-m}$ alkoxy" means that the alkyl moiety of the alkoxy group has n to m carbon atoms. In some embodiments, the alkyl moiety has 1 to 6, 1 to 4, or 1 to 3 carbon atoms. Examples of alkoxy groups include, but are not limited to, chemical groups such as methoxy, ethoxy, propoxy (e.g., n-propoxy and isopropoxy), 1-butoxy, and the like.

As used herein, the term "aryloxyl" refers to a group of formula —O-aryl, wherein the aryl group is as previously described. "$C_{n-m}$ aryloxyl" means that the aryl moiety of the aryloxyl group has n to m carbon atoms. In some embodiments, the aryl moiety has 5 to 10, 5 to 8, or 5 to 6 carbon atoms.

As used herein, the term "alkylamino", whether as part of another term or used independently, refers to a group of formula —NH-alkyl. The term "$C_{n-m}$ alkylamino" means that the alkyl moiety of the alkylamino group has n to m carbon atoms. In some embodiments, the alkyl moiety has 1 to 6, 1 to 4, or 1 to 3 carbon atoms.

As used herein, the term "arylcarbonyl", whether as part of another term or used independently, refers to a group of formula —C(=O)-aryl, wherein the aryl group is as previously described. "$C_{n-m}$ arylcarbonyl" means that the aryl moiety of the arylcarbonyl group has n to m carbon atoms. In some embodiments, the aryl moiety has 5 to 10, 5 to 8, or 5 to 6 carbon atoms.

As used herein, the term "alkylcarbonyl", whether as part of another term or used independently, refers to a group of formula —C(=O)-alkyl. The term "$C_{n-m}$ alkylcarbonyl" means that the alkyl moiety of the alkylcarbonyl group has n to m carbon atoms. In some embodiments, the alkyl moiety has 1 to 6, 1 to 4, 1 to 3 or 1 to 2 carbon atoms.

As used herein, the term "alkoxycarbonyl", whether as part of another term or used independently, refers to a group of formula —C(=O)—O-alkyl. The term "$C_{n-m}$ alkoxycarbonyl" means that the alkyl moiety of the alkoxycarbonyl group has n to m carbon atoms. In some embodiments, the alkyl moiety has 1 to 6, 1 to 4, 1 to 3 or 1 to 2 carbon atoms.

As used herein, the term "cycloalkoxylcarbonyl", whether as part of another term or used independently, refers to a group of formula —C(=O)—O-cycloalkyl, wherein the cycloalkyl group is as previously described. The term "$C_{n-m}$ cycloalkyloxylcarbonyl" means that the cycloalkyl moiety of the cycloalkoxylcarbonyl group has n to m carbon atoms. In some embodiments, the cycloalkyl moiety has 3 to 8, 3 to 6, 3 to 5 or 3 to 4 carbon atoms.

As used herein, the term "alkylcarbonyloxyl", whether as part of another term or used independently, refers to a group of formula —O—C(=O)-alkyl. The term "$C_{n-m}$ alkylcarbonyloxyl" means that the alkyl moiety of the alkylcarbonyloxyl group has n to m carbon atoms. In some embodiments, the alkyl moiety has 1 to 6, 1 to 4, 1 to 3 or 1 to 2 carbon atoms.

As used herein, the term "n membered", wherein n is an integer typically employed in combination with a ring system to describe the number of ring-forming atoms in the ring system. For example, piperidinyl is an example of a 6 membered heterocycloalkyl ring, pyrazolyl is an example of a 5 membered heteroaryl ring, pyridyl is an example of a 6 membered heteroaryl ring, and 1,2,3,4-tetrahydro-naphthalene is an example of a 10 membered cycloalkyl group.

As used herein, the term "heterocyclic aryl" refers to aryl group wherein at least one ring atom in the aromatic ring is a heteroatom, and the remainder of the ring atoms being carbon atoms. The term "n-m membered heterocyclic aryl" refers to heterocyclic aryl having n to m ring-forming members. Example heteroatoms include, but are not limited to, oxygen, sulfur, nitrogen, phosphorus, and the like. In some embodiments, heterocyclic aryl can have 5 to 10, 5 to 8, or 5 to 6 ring-forming members. In some embodiments, heterocyclic aryl is 5 membered or 6 membered heterocyclic aryl. Examples of heterocyclic aryl include, but are not limited to, furanyl, thienyl, pyridyl, pyrrolyl, N-lower alkyl pyrrolyl, pyridyl-N-oxide, pyrimidyl, pyrazinyl, imidazolyl, indolyl and the like.

A 5 membered heterocyclic aryl is a heterocyclic aryl with a ring having five ring atoms, wherein one or more (e.g., 1, 2, or 3) ring atoms can be independently selected from N, O, P, and S. Exemplary 5 membered heterocyclic aryl are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A 6 membered heterocyclic aryl is a heterocyclic aryl with a ring having six ring atoms, wherein one or more (e.g., 1, 2, or 3) ring atoms can be independently selected from N, O, P, and S. Exemplary 6 membered heterocyclic aryl are pyridyl, pyrazinyl, pyrimidinyl, triazinyl and pyridazinyl.

As used herein, the term "heterocyclic alkyl" refers to cycloalkyl group wherein at least one ring atom in the ring systems is a heteroatom, and the remainder of the ring atoms being carbon atoms. The term "n-m membered heterocyclic alkyl" refers to heterocyclic alkyl having n to m ring-forming members. In addition, the ring may also have one or more double bonds, but not have a completely conjugated system. In some embodiments, the heterocyclic alkyl is saturated heterocyclic alkyl. Examples of heteroatoms include, but are not limited to, oxygen, sulfur, nitrogen, phosphorus, and the like. In some embodiments, heterocyclic alkyl has 3 to 8, 3 to 6, or 4 to 6 ring-forming carbons. Examples of heterocyclic alkyl include, but are not limited to, azetidine, aziridine, pyrrolidyl, piperidyl, piperazinyl, morpholinyl, thiomorpholinyl, homopiperazinyl, and the like.

As used herein the terms "halo" and "halogen" refer to an atom selected from fluorine, chlorine, bromine and iodine.

As used herein, "mono-, di- or tri-halo-$C_{n-m}$ alkyl" refers to an alkyl group that is substituted by one, two or three halo, wherein the alkyl group has n to m carbon atoms and the halo as substituent may be same or different. Examples of mono-, di- or tri-halo-$C_{n-m}$ alkyl include without limitation, trichloromethyl, chloromethyl, bischloromethyl, chlorobromomethyl.

As used herein the terms "cyano" refer to a group of formula —CN.

As used herein, the term "hydroxyl" refers to a group of formula —OH.

As used herein, the term "methylthio" refers to a group of formula —S—$CH_3$.

As used herein, the term "alkylsulfonyl" refers to a group of formula -sulfonyl-alkyl. The term "$C_{n-m}$ alkylsulfonyl" refers to alkylsulfonyl wherein the alkyl moiety has n to m carbon atoms. In some embodiments, the alkyl group has 1 to 6, 1 to 4, or 1 to 3 carbon atoms. Examples of alkylsulfonyl groups include without limitation, methanesulfonyl, ethanesulfonyl, tert-butanesulfonyl, and the like.

As used herein, the term "amino" refers to a group of formula —$NH_2$.

As used herein, the term "substituted amino" refers to an amino that is mono- or independently substituted by one or more substituents. Examples of substituents include, but are not limited to, halogen, hydroxyl, $C_{1-4}$ alkyl, $C_{5-8}$ aryl, $C_{1-6}$ alkoxyl, $C_{3-8}$ cycloalkyl, 3-8 membered heterocyclic alkyl, or 3-8 membered heterocyclic aryl, $C_{1-4}$ alkylsulfonyl, $C_{5-10}$ aryloxyl, $C_{5-10}$ arylcarbonyl or $C_{1-6}$ alkyloxycarbonyl, amino protecting group, and the like.

As used herein, the term "amino protecting group" refers to a substituent that protects an amino functionality against undesirable reactions during synthetic procedures. Examples of amino protecting groups include, but are not limited to, carbamate-protecting groups, such as 2-trimethyl-silylethoxycarbonyl (Teoc), 1-methyl-1-(4-bi-phenylyl)-ethoxycarbonyl (Bpoc), t-butoxycarbonyl (Boc), allyloxycarbonyl (Alloc), 9-fluorenyl-methyloxycarbonyl (Fmoc), and benzyl-oxycarbonyl (Cbz); amide-protecting groups, such as formyl, acetyl, trihaloacetyl, benzoyl, and nitrophenylacetyl; sulfonamide-protecting groups, such as 2-nitrobenzenesulfonyl; and imine- and cyclic imide-protecting groups, such as phthalimido and dithiasuccinoyl.

As used herein, the term "compound" is meant to include all stereoisomers (eg. enantiomers and diastereomers), geometric iosomers, tautomers, and isotopes of the structures depicted. Compounds herein identified by name or structure as one particular tautomeric form are intended to include other tautomeric forms unless otherwise specified.

The compounds described herein can be asymmetric (e.g., having one or more stereocenters). All stereoisomers, such as enantiomers and diastereomers, are intended unless otherwise indicated. Compounds of the present disclosure that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, carbon-carbon double bonds, and the like can also be present in the compounds described herein, and all such stable isomers are contemplated in the present disclosure. Cis and trans geometric isomers of the compounds of the present disclosure are described and may be isolated as a mixture of isomers or as separated isomeric forms.

In some embodiments, the compounds described herein have the (R)-configuration. In some embodiments, the compounds described herein have the (S)-configuration.

Resolution of racemic mixtures of compounds can be carried out by any of numerous methods known in the art. An example method includes fractional recrystallization using a chiral resolving acid, which is an optically active, salt-forming organic acid. Suitable resolving agents for fractional recrystallization methods are, for example, optically active acids, such as the D and L forms of tartaric acid, diacetyltartaric acid, dibenzoyltartaric acid, mandelic acid, malic acid, lactic acid or the various optically active camphorsulfonic acids such as β-camphorsulfonic acid. Other resolving agents suitable for fractional crystallization methods include stereoisomerically pure forms of α-methylbenzylamine (e.g., S and R forms, or diastereomerically pure forms), 2-phenylglycinol, norephedrine, ephedrine, N-methylephedrine, cyclohexylethylamine, 1,2-diaminocyclohexane, and the like.

Resolution of racemic mixtures can also be carried out by elution on a column packed with an optically active resolving agent (e.g., dinitrobenzoylphenylglycine). Suitable elution solvent composition can be determined by one skilled in the art.

Compounds of the present disclosure also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

Compounds of the present disclosure can also include all isotopes of atoms occurring in the intermediates or final compounds. Isotopes include those atoms having the same atomic number but different mass numbers. For example, isotopes of hydrogen include protium, deuterium and tritium. In some embodiments, the isotope of hydrogen is protium and deuterium. In some embodiments, the hydrogens on the aromatic ring of the compounds include at least one deuterium. In some embodiments, the hydrogens on the aromatic ring of the compounds are all deuteriums.

In some embodiments, the compounds of the present disclosure can convert to GHB after oral administration. In some embodiments, the compounds of the present disclosure can enter into human circulatory system through a biological process after oral administration. In some embodiment, the compounds of the present disclosure convert to GHB in liver. In some embodiment, the compounds of the present disclosure convert to GHB in blood. In some embodiment, the GHB releasing efficiency of the compounds within 1 hour after contacting blood or liver is no less than 90%, 80%, 70%, 60%, 50%, 40%, 30%, 20%, or 10%. In some embodiment, the GHB releasing efficiency of the compounds within 2 hours after contacting blood or liver is no less than 90%, 80%, 70%, 60%, 50%, 40%, 30%, or 20%.

In some embodiments, the compounds of the present disclosure have higher oral bioavailability than the oral bioavailability of GHB sodium salt. In some embodiments, the oral bioavailability of the compounds of the present disclosure is 1.1, 1.2, 1.3, 1.4, 1.5, 1.6, 1.7, 1.8, 1.9, 2, 2.5, 3, or 4 times higher than the oral bioavailability of GHB sodium salt. In some embodiments, the compounds of the present disclosure have higher colonic absorption than the colonic absorption of GHB. In some embodiments, the colonic absorption of the compounds of the present disclosure is 1.1, 1.2, 1.3, 1.4, 1.5, 1.6, 1.7, 1.8, 1.9, 2, 2.5, 3, 4, 5, 6, 8, or 10 times higher than the colonic absorption of GHB. In some embodiment, the oral bioavailability of the compounds of the present disclosure is no less than 20%, 30%, 40%, 50%, 60%, 70%, 80%, or 90%.

Not to be limited by the theory, the nature of compounds of the present disclosure enables the compounds to be formulated to a stable solid formulation, especially the sustained or controlled-release formulation. For example, some compounds of the present disclosure can be formulated into a drug with controlled absorption in GI tract. In some embodiment, the oral absorption of the compounds in the colon is no less than 40%, 50%, 60%, 70%, 80%, 90% or more of the total oral absorption.

Synthesis Method

Compounds of the present disclosure, including salts, esters, hydrates, or solvates thereof, can be prepared using any known organic synthesis techniques and can be synthesized according to any of numerous possible synthetic routes.

The reactions for preparing compounds of the present disclosure can be carried out in suitable solvents, which can be readily selected by one skilled in the art of organic synthesis. Suitable solvents can be substantially non-reactive with the starting materials (reactants), the intermediates, or products at the temperatures at which the reactions are carried out, e.g., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected by a skilled artisan.

Preparation of compounds of the present disclosure can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, Protective Groups in Organic Synthesis, 3rd Ed., Wiley & Sons, Inc., New York (1999), which is incorporated herein by reference in its entirety.

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) ("Preparative LC-MS Purification: Improved Compound Specific Method Optimization" Karl F. Blom, Brian Glass, Richard Sparks, Andrew P. Combs J. Combi. Chem. 2004, 6(6), 874-883, which is incorporated herein by reference in its entirety) and normal phase silica chromatography. Exemplary synthetic schemes are listed below, the abbreviations for the reactants or for the chemical groups of the reactants included in the synthetic schemes are defined in the Examples.

For example, compounds of Formula I can be formed as shown in Scheme 1.

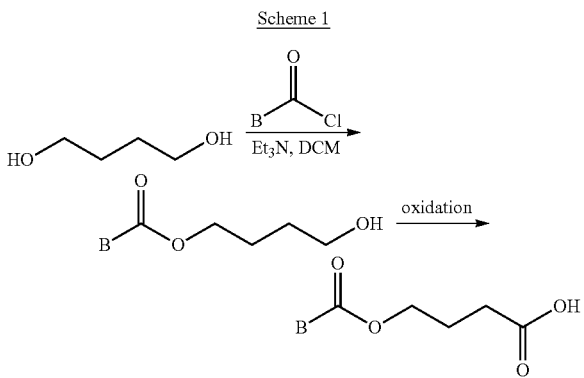

Alternatively, compounds of Formula I can be formed as shown in Scheme 2.

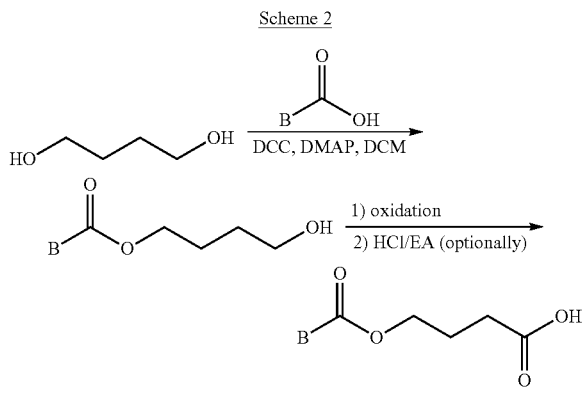

For example, compounds of Formula IA can be formed as shown in Scheme 3 (X in the scheme refers to any substituent group).

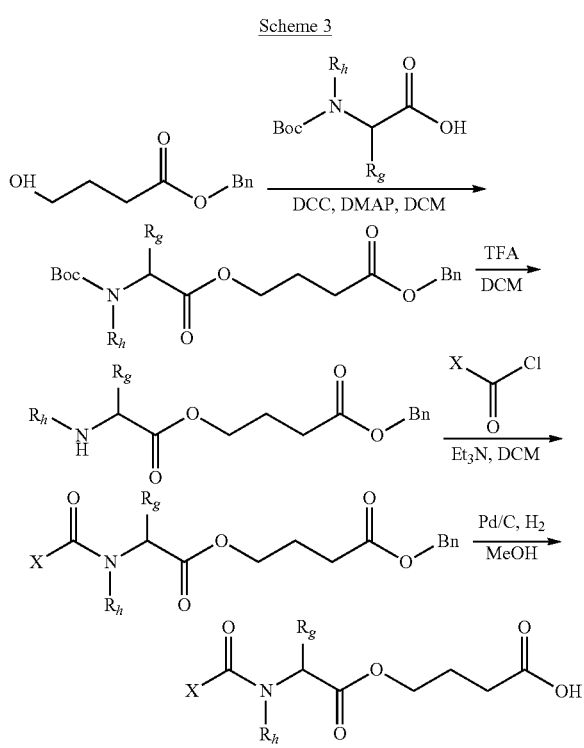

A representative compound of Formula IA can be formed as shown in Scheme 4.

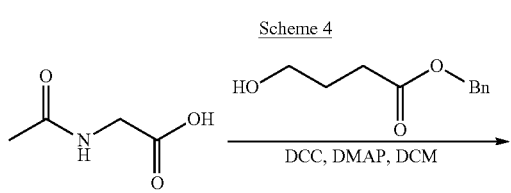

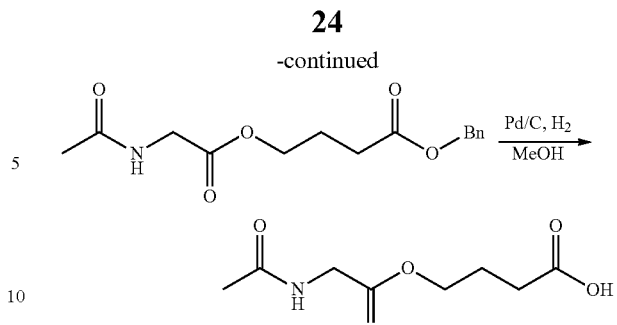

A representative compound of Formula IA can be formed as shown in Scheme 5.

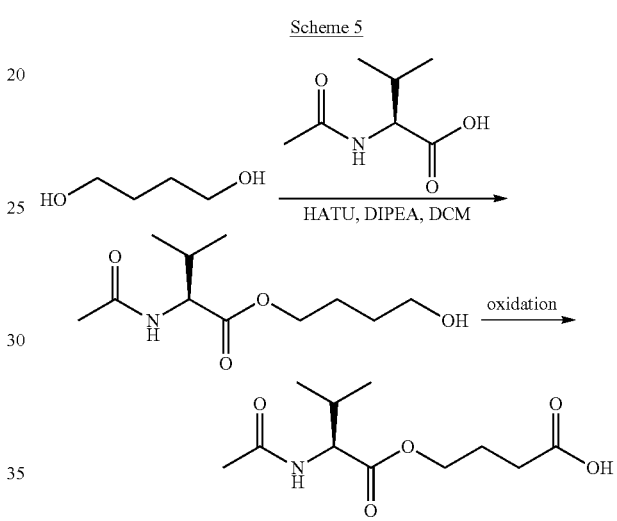

Alternatively, the compounds of Formula IA can be formed as shown in Scheme Scheme 6 (wherein X in the scheme refers to any substituent group).

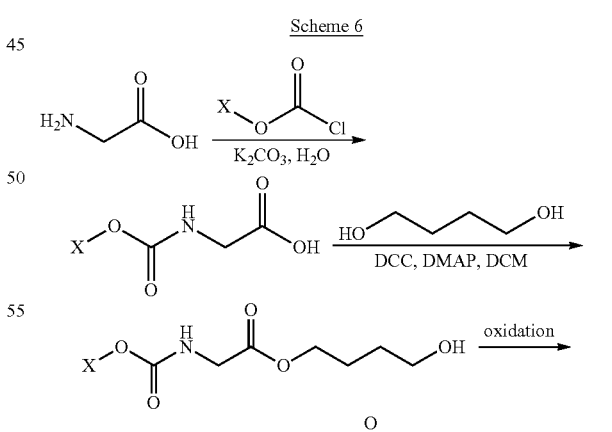

A representative compound of Formula IA can be formed as shown in Scheme 7.

Scheme 7

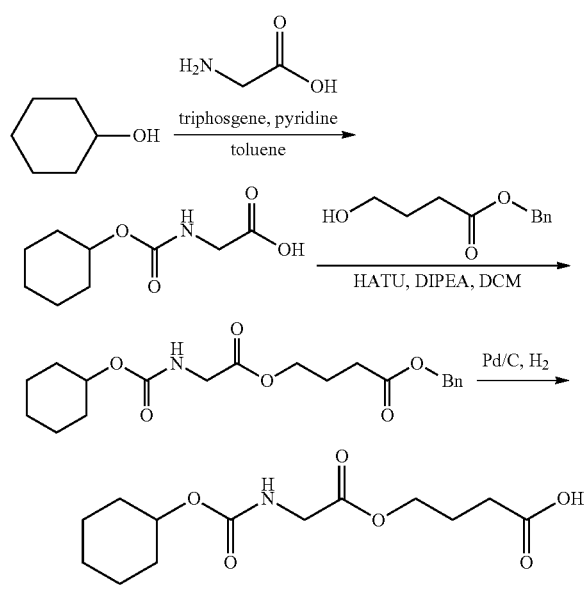

A representative compound of Formula IA can be formed as shown in Scheme 8.

Scheme 8

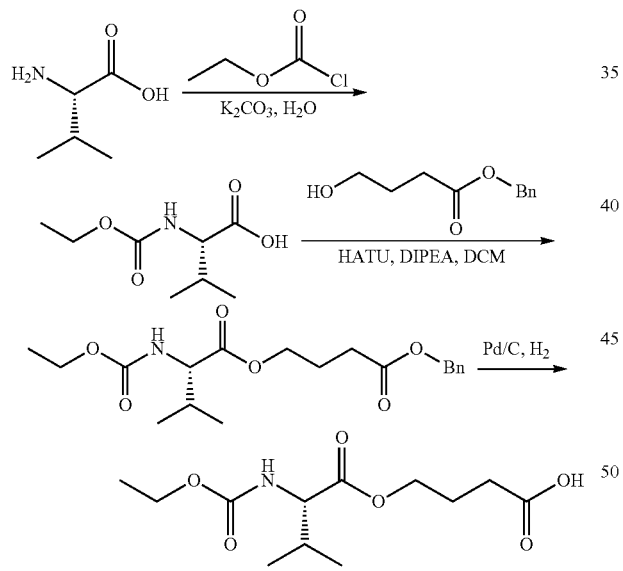

A representative compound of Formula IA-2 can be formed as shown in Scheme 9.

Scheme 9

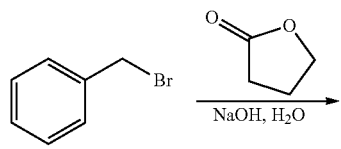

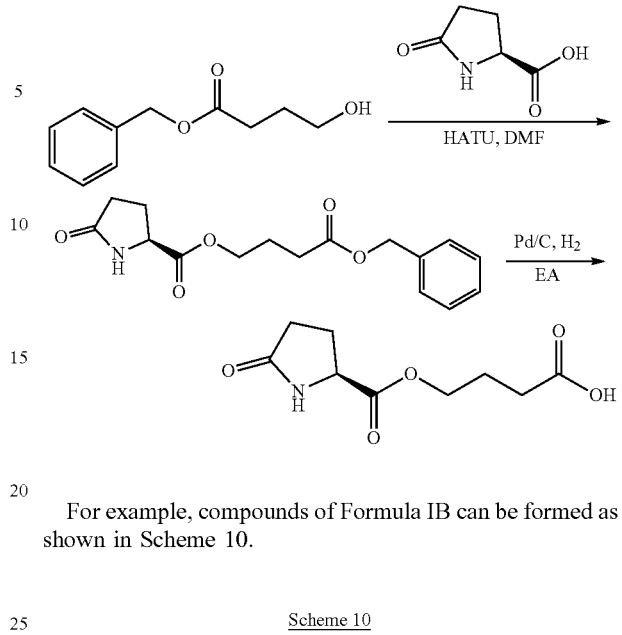

For example, compounds of Formula IB can be formed as shown in Scheme 10.

Scheme 10

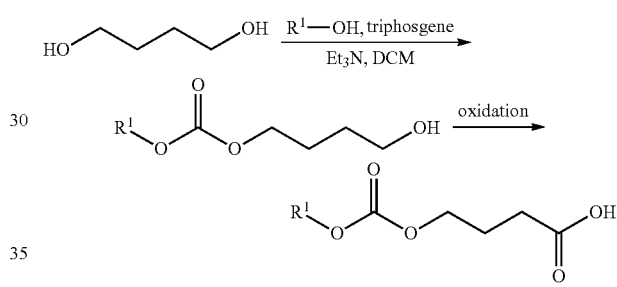

A representative compound of Formula IB can be formed as shown in Scheme 11.

Scheme 11

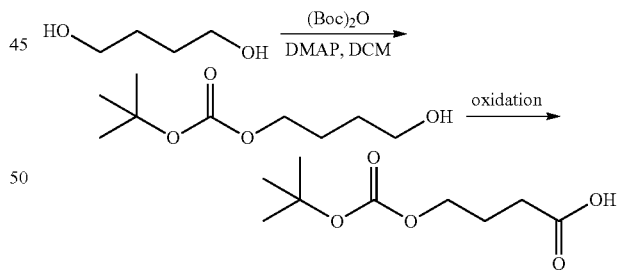

A representative compound of Formula IB can be formed as shown in Scheme 12.

Scheme 12

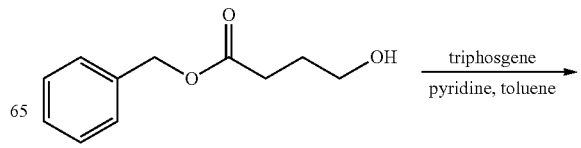

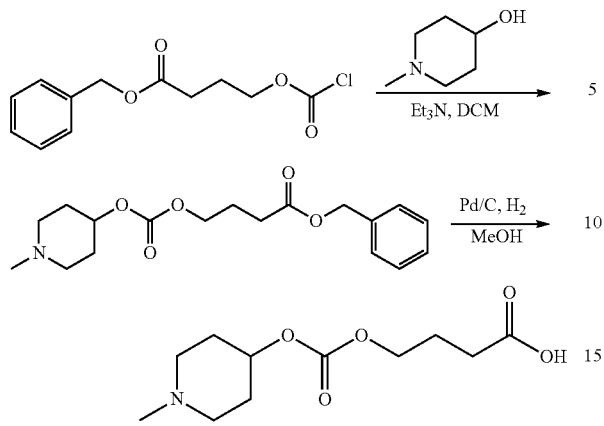

For example, compounds of Formula ID can be formed as shown in Scheme 13.

Scheme 13

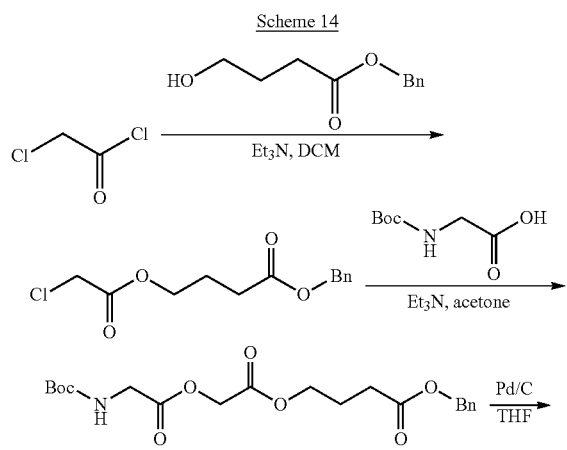

A representative compound of Formula ID-2 can be formed as shown in Scheme 14.

Scheme 14

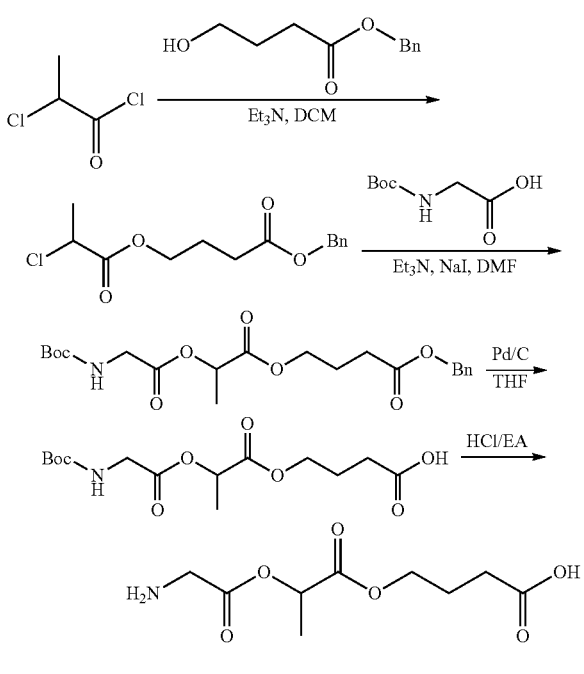

A representative compound of Formula ID-2 can be formed as shown in Scheme 15.

Scheme 15

A representative compound of Formula ID-2 can be formed as shown in Scheme 16.

Scheme 16

For example, compounds of Formula IE can be formed as shown in Scheme 17.

Scheme 17

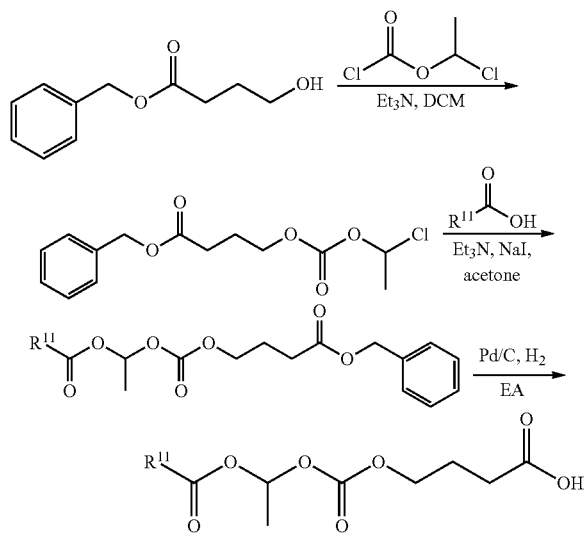

Pharmaceutical Composition

The present disclosure provides pharmaceutical composition comprising one or more compounds of the present disclosure, and a pharmaceutically acceptable carrier.

These pharmaceutical compositions can be prepared in a manner well known in the pharmaceutical art. In some embodiments, the compounds of the present disclosure may be admixed with pharmaceutically acceptable carrier for the preparation of pharmaceutical composition.

As used herein, the phrase "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio. In some embodiments, compounds, materials, compositions, and/or dosage forms that are pharmaceutically acceptable refer to those approved by a regulatory agency (such as U.S. Food and Drug Administration, China Food and Drug Administration or European Medicines Agency) or listed in generally recognized pharmacopoeia (such as U.S. Pharmacopoeia, China Pharmacopoeia or European Pharmacopoeia) for use in animals, and more particularly in humans.

As used herein, the term "pharmaceutically acceptable carrier" refers to any and all solvents, excipients, coatings, antibacterial and antifungal agents, flavoring agents, isotonic and absorption delaying agents, and the like that are pharmaceutically acceptable and can facilitate storage and administration of the compounds of the present disclosure to a subject. Pharmaceutically acceptable carrier that can be employed in present disclosure includes those generally known in the art, such as those described in "Remington Pharmaceutical Sciences" Mack Pub. Co., New Jersey (1991), which is incorporated herein by reference.

Examples of pharmaceutically acceptable carriers include, but are not limited to, solvents, liposomes, polymeric excipients and the like.

In certain embodiments, the pharmaceutically acceptable carrier is a solvent that can dissolve or disperse the compounds of the present disclosure. Illustrative examples of solvent include, without limitation, buffer saline, normal saline, phosphate buffer, citrate buffer, acetate buffer, bicarbonate buffer, sucrose solution, polysorbate solution, oil, ester, and alcohol.

In certain embodiments, the pharmaceutically acceptable carriers are liposomes, and the compounds of the present disclosure can be encapsulated within the aqueous portion or lipid portion of the liposomes. Illustrative examples of liposomes include, without limitation, liposomes based on 3[N—(N',N'-dimethylaminoethane) carbamoyl] cholesterol (DC-Chlo), liposomes based on N-(2,3-dioleoyloxy)propyl-N,N,N-trimethylammonium chloride (DOTMA), and liposomes based on 1,2-dioleoyloxy-3-trimethylammonium propane (DOTAP).

In certain embodiments, the pharmaceutically acceptable carriers are polymeric excipients such as, without limitation, microspheres, microcapsules, polymeric micelles and dendrimers. The compounds of the present disclosure may be encapsulated, adhered to, or coated on the polymer-based components by methods known in the art.

The form of pharmaceutical compositions depends on a number of criteria, including, but not limited to, route of administration, extent of disease, or dose to be administered. The pharmaceutical compositions can be formulated for oral, nasal, rectal, percutaneous, intravenous, or intramuscular administration. In accordance with the desired route of administration, the pharmaceutical compositions can be formulated in the form of tablets, pills, powders, lozenges, sachets, cachets, suspensions, emulsions, solutions, syrups, aerosols (as a solid or in a liquid medium) or ointments.

For oral administration, powders, granules, pills, tablets, caplets, capsules, and gelcaps are acceptable as solid dosage forms. These can be prepared, for example, by mixing one or more compounds of the present disclosure with at least one carrier such as sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, and/or polyvinylpyrrolidone. In some embodiments, solid dosage forms for oral administration can further comprise other carrier ingredients to aid in manufacture or administration with lubricants such as magnesium stearate, or preservatives such as paraben or sorbic acid, or anti-oxidants such as ascorbic acid, tocopherol or cysteine, a disintegrating agents, or chelating agents such as EDTA, binders, thickeners, flavoring agents or perfuming agents. In certain embodiments, solid dosage forms for oral administration may additionally comprise dyestuffs or pigments for identification. Tablets and pills may be further treated with suitable coating materials known in the art, such as moisture protective, enteric, or sustained release coatings.

For oral administration, emulsions, syrups, elixirs, suspensions, slurries and solutions are acceptable as liquid dosage forms. These can be prepared, for example, by mixing one or more compounds of the present disclosure with sterile inactive solvent, such as but not limited to, water, alcohol, oil and a combination thereof. In some embodiments, the inactive diluent used in the liquid dosage form for oral administration comprise oil, such as but not limited to, peanut oil, sesame oil, cottonseed oil, corn oil and olive oil. In some embodiments, the inactive diluent used in the liquid dosage form for oral administration comprise esters of fatty acids, such as but not limited to, ethyl oleate, isopropyl myristate, fatty acid glycerides and acetylated fatty acid glycerides. In some embodiments, the inactive diluent used in the liquid dosage form for oral administration comprise alcohols, such as but not limited to, ethanol, isopropyl alcohol, hexadecyl alcohol, glycerol and propylene glycol. In some embodiment, liquid dosage forms for oral administration can further comprise surfactants, suspending agents, emulsifying agents, stabilizers, flavoring agents, chelating agents, preservatives, antioxidants, solubilizers (such as propylene glycol, glycerin, or sorbitol), dyes, or thickeners. In some embodiments, the liquid dosage form for oral administration can further comprise pH adjusting agent, such as but not limited to, sodium hydroxide, hydrochloric acid, or malic acid.

The pharmaceutical composition of the present disclosure can be formulated so as to provide quick, sustained or delayed release of the active ingredient after administration to the patient by employing procedures known in the art. In some embodiments, the composition is formulated in a sustained released form. As used herein, the term "sustained released form" refers to release of the active agent from the pharmaceutical composition so that it becomes available for bio-absorption in the subject, primarily in the gastrointestinal tract of the subject, over a prolonged period of time (extended release), or at a certain location (controlled release). In some embodiments, the prolonged period of time can be about 1 hour to 24 hours, 2 hours to 12 hours, 3 hours to 8 hours, 4 hours to 6 hours, 1 to 2 days or more. In certain embodiments, the prolonged period of time is at least about 4 hours, at least about 8 hours, at least about 12 hours, or at least about 24 hours.

In some embodiments, the sustained release form of pharmaceutical compositions are tablets or pills, and the tablets or pills are coated or otherwise formulated to provide a dosage form affording the advantage of prolonged action. Factors affecting drug release are well known to the skilled artisan and have been described in the art (Bamba et al., *Int. J. Pharm.*, 1979, 2, 307), which is incorporated herein by reference in its entirety. For example, release rate of the active agent can not only be controlled by dissolution of the active agent in gastrointestinal fluid and subsequent diffusion out of the tablet or pills independent of pH, but can also be influenced by physical processes of disintegration and erosion of the tablet. In some embodiments, polymeric materials as described in "Medical Applications of Controlled Release," Langer and Wise (eds.), CRC Pres., Boca Raton, Fla. (1974); "Controlled Drug Bioavailability," Drug Product Design and Performance, Smolen and Ball (eds.), Wiley, New York (1984); Ranger and Peppas, 1983, *J Macromol. Sci. Rev. Macromol Chem.* 23:61, see also Levy et al., 1985, *Science* 228:190; During et al., 1989, *Ann. Neurol.* 25:351; Howard et al., 1989, *J. Neurosurg.* 71:105 can be used for sustained release. The above references are incorporated herein by reference in its entirety.

In some embodiments, polymeric materials are used for oral sustained release delivery. Examples of the polymeric materials include sodium carboxymethylcellulose, hydroxypropylcellulose, hydroxypropylmethylcellulose and hydroxyethylcellulose. Other cellulose ethers have been described in Alderman, *Int. J. Pharm. Tech. & Prod. Mfr.*, 1984, 5(3) 1-9, which is incorporated herein by reference in its entirety. In some embodiments, enteric-coated preparations can be used for oral sustained release administration. Examples of the coating materials include polymers with a pH-dependent solubility (i.e., pH-controlled release), polymers with a slow pH-dependent rate of swelling, dissolution or erosion (i.e., time-controlled release), polymers that are degraded by enzymes (i.e., enzyme-controlled release) and polymers that form firm layers that are destroyed by an increase in pressure (i.e., pressure-controlled release). In some embodiments, osmotic delivery systems are used for oral sustained release administration as described in Verma et al., *Drug Dev. Ind. Pharm.*, 2000, 26:695-708, which is incorporated herein by reference in its entirety. In a preferred embodiment, OROS™ osmotic devices are used for oral sustained release delivery devices as described in Theeuwes et al., U.S. Pat. No. 3,845,770; Theeuwes et al., U.S. Pat. No. 3,916,899, which are incorporated herein by reference in its entirety. In some embodiments, a controlled-release system can be placed in proximity of the target of the compounds and/or composition of the present disclosure, thus requiring only a fraction of the systemic dose, see. e.g., Goodson, in "Medical Applications of Controlled Release," supra, vol. 2, pp. 115-138 (1984), which is incorporated herein by reference in its entirety. Other controlled-release systems as described in Langer, 1990, *Science* 249:1527-1533 may also be used, which is incorporated herein by reference in its entirety.

The compositions can be formulated in a unit dosage form, each dosage containing from about 0.5 to about 30 g, about 1 to about 20 g, about 2 to about 20 g, about 3 to about 20 g, about 4 to about 20 g, about 5 to about 20 g, about 6 to about 20 g, about 7 to about 20 g, about 8 to about 20 g, about 9 to about 20 g, about 10 to about 20 g, about 11 to about 20 g, about 12 to about 20 g, about 13 to about 20 g, about 14 to about 20 g, about 15 to about 20 g, about 16 to about 20 g, about 17 to about 20 g, about 18 to about 20 g, 2 to about 18 g, about 2 to about 16 g, about 2 to about 14 g, about 2 to about 12 g, about 2 to about 10 g, about 2 to about 9 g, about 2 to about 8 g, about 2 to about 6 g of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical carrier.

Method for Treatment

The present disclosure provides, a method of treating a disease, comprising administering to a subject an effective amount of one or more compounds of the present disclosure.

In some embodiments, the disease is narcolepsy, excessive daytime sleepiness, cataplexy, neurodegenerative disease, sleep disturbance syndrome, fibromyalgia, chronic fatigue, schizophrenia, binge eating disorder, Parkinson disease, tardive dyskinesia, or Alzheimer's disease. In some embodiments, the disease is excessive daytime sleepiness or cataplexy associated with narcolepsy.

Administration may be via oral, nasal, intravenous, subcutaneous, sublingual, or intramuscular administration.

The frequency of administration of the compounds will vary depending upon what is being administered, the amount of the therapeutic agent, the purpose of the administration, the state of the patient, the manner of administration, and the like. Determination of frequency of administration is well within the capability of those skilled in the art. In some embodiments, the administration is conducted no more than two time per day, no more than one time per day, no more than two times per three days, no more than one time per two days, no more than one time per three days, no more than one time per five days, no more than one time per one week, or no more than one time per two weeks.

As used herein, the term "effective amount" means an amount of the therapeutic agent that is effective to provide a desired outcome. Determination of a therapeutically effective amount is well within the capability of those skilled in the art. Generally, a therapeutically effective amount can vary with the subject's history, age, condition, sex, as well as the severity and type of the medical condition in the subject, and administration of other agents that inhibit pathological processes in neurodegenerative disorders. In some embodiments, the effective amount of the therapeutic agent is from about 0.5 to about 30 g, about 1 to about 15 g, about 2 to about 15 g about 3 to about 10 g, about 4 to about 10 g.

As used herein, the term "treating" or "treatment" of any disease or disorder refers to delaying onset of the disease or disorder; ameliorating at least one of the clinical symptoms relating to the disease or disorder; or both.

Pharmaceutical Use

The present disclosure also provides use of one or more compounds of the present disclosure in the manufacture of a medicament for treating a disease. In some embodiments, the disease is narcolepsy, excessive daytime sleepiness, cataplexy, neurodegenerative disease, sleep disturbance syndrome, fibromyalgia, chronic fatigue, schizophrenia, binge eating disorder, Parkinson disease, tardive dyskinesia, or Alzheimer's disease. In some embodiments, the disease is excessive daytime sleepiness or cataplexy associated with narcolepsy.

The present disclosure also provides the compounds of the present disclosure for treating a disease. In some embodiments, the disease is narcolepsy, excessive daytime sleepiness, cataplexy, neurodegenerative disease, sleep disturbance syndrome, fibromyalgia, chronic fatigue, schizophrenia, binge eating disorder, Parkinson disease, tardive dyskinesia, or Alzheimer's disease. In some embodiments, the disease is excessive daytime sleepiness or cataplexy associated with narcolepsy.

EXAMPLES

The following examples are presented to illustrate the present disclosure. They are not intended to be limiting in any manner.

Example 1: Preparation and Characterization of Exemplary Compounds

Compounds encompassed in the present disclosure may be prepared via different schemes. Detailed preparation processes of 90 exemplary compounds via various schemes are described below and the characterization results are listed for each compound as well.

Unless stated otherwise, all reagents were purchased from commercial suppliers without further purification. Solvent drying by standard methods was employed when necessary. The plates used for thin-layer chromatography (TLC) were E. Merck silica gel 60F254 (0.24 nm thickness) precoated on aluminum plates, and then visualized under UV light (365 nm and 254 nm) or through staining with a 5% of dodecamolybdophosphoric acid in ethanol and subsequent heating. Column chromatography was performed using silica gel (200-400 mesh) from commercial suppliers. $^1$H NMR spectra were recorded on an Agilent 400-MR NMR spectrometer (400.00 MHz for 1H) at room temperature. Solvent signal was used as reference for $^1$H NMR (CDCl$_3$, 7.26 ppm; CD$_3$OD, 3.31 ppm; d$_6$-DMSO, 2.50 ppm; D$_2$O, 4.79 ppm). The following abbreviations were used to explain the multiplicities: s=singlet, d=doublet, t=triplet, q=quartet, br.s.=broad singlet, dd=double doublet, td=triple doublet, dt=double triplet, dq=double quartet, m=multiplet. Other abbreviations used in the experimental details are as follows: Ar=aryl, Boc=tert-butyloxy carbonyl, Bn=Benzyl, S= chemical shift in parts per million downfield from tetramethylsilane, DCC=dicyclohexylcarbodiimide, DCM= dichloromethane, DIPEA=diisopropylethylamine, DMAP= 4-(dimethylamino)pyridine, DMF=N,N'-dimethylformamide, EA=ethyl acetate, Et=ethyl, HATU=1-[bis(dimethylamino)methylene]-1H-1,2,3-triazolo[4,5-b]pyridinium 3-oxide hexafluorophosphate, Hex.=hexanes, Hz=hertz, J= coupling constant (in NMR), Me=methyl, min=minute (s), NMR=nuclear magnetic resonance, Ph=phenyl, ppm=parts per million, iPr=isopropyl, TBAF=tetrabutylammonium fluoride, tert=tertiary, TFA=trifluoroacetic acid, THF= tetrahydrofuran, TLC=thin-layer chromatography.

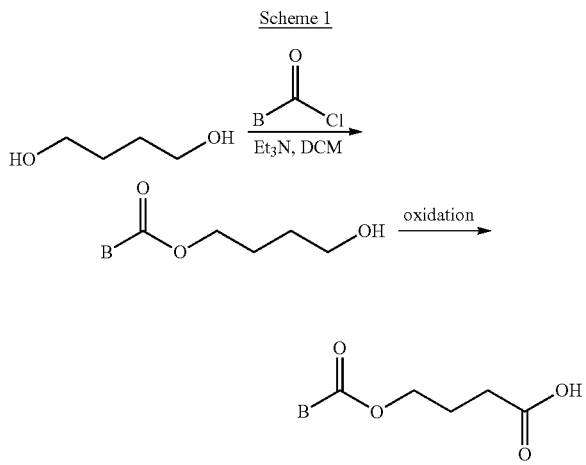

Scheme 1

Example 1-1

Intermediate Compound 1': 4-hydroxybutyl 2-methylbenzoate

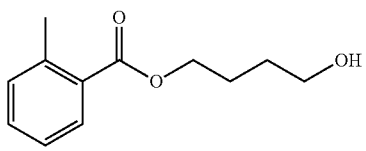

A solution of 2-methylbenzoyl chloride (770 mg, 5 mmol) in DCM (2 mL) was added dropwise during 10 min to a stirred solution of butane-1,4-diol (450 mg, 5 mmol) and Et$_3$N (505 mg, 5 mmol) in DCM (8 mL) at 0° C. The reaction was allowed to warm up gradually and stirred at 0-25° C. for over 1 h. After that, the reaction mixture was diluted with H$_2$O (5 mL) and stirred for 5 min. The aqueous phase was separated and extracted with DCM (5 mL). The combined organic phase was then washed with saturated brine (5 mL), dried over anhydrous Na$_2$SO$_4$ and evaporated. The residue was purified by a silica gel flash column with Hex/EA=10:1-3:1 to yield the titled compound (470 mg, 45%) as a colorless oil. $^1$H NMR was performed at 400 MHz with CDCl$_3$ as solvent to characterize the titled compound, results are as follows: δ=7.91 (d, J=8.0 Hz, 1H), 7.40 (t, J=7.4 Hz, 1H), 7.26-7.22 (m, 2H), 4.34 (t, J=6.8 Hz, 2H), 3.73 (t, J=6.4 Hz, 2H), 2.60 (s, 3H), 1.90-1.83 (m, 2H), 1.77-1.70 (m, 2H).

35

Compound 1: 4-(2-methylbenzoyloxy)butanoic Acid

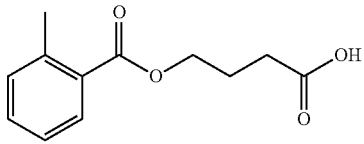 [SMILES: Cc1ccccc1C(=O)OCCCC(=O)O]

Jones reagent was added in portions to a stirred mixture of 4-hydroxybutyl 2-methylbenzoate (400 mg, 1.92 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), then dried over anhydrous $Na_2SO_4$ and concentrated. The residue was purified by a silica gel flash column with Hex/EA=3:1 to yield the titled compound (380 mg, 89%) as crystalline solids. $^1H$ NMR was performed at 400 MHz with $CDCl_3$ as solvent to characterize the titled compound, results are as follows: δ=7.91 (d, J=8.0 Hz, 1H), 7.40 (t, J=7.8 Hz, 1H), 7.28-7.22 (m, 2H), 4.36 (t, J=6.2 Hz, 2H), 2.61 (s, 3H), 2.55 (t, J=7.4 Hz, 2H), 2.15-2.08 (m, 2H).

Example 1-2

Intermediate Compound 2': 4-hydroxybutyl 3-methylbenzoate

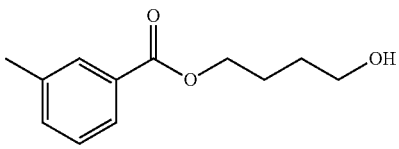

A solution of 3-methylbenzoyl chloride (616 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was then washed with saturated brine (5 mL), dried over anhydrous $Na_2SO_4$ and evaporated. The residue was purified by a silica gel flash column with Hex/EA=10:1-3:1 to yield the titled compound (410 mg, 49%) as a colorless oil. $^1H$ NMR was performed at 400 MHz with $CDCl_3$ as solvent to characterize the titled compound, results are as follows: δ=7.83-7.81 (m, 2H), 7.35-7.28 (m, 2H), 4.33 (t, J=6.6 Hz, 2H), 3.70 (t, J=6.4 Hz, 2H), 2.38 (s, 3H), 2.07 (s, 1H), 1.89-1.82 (m, 2H), 1.75-1.68 (m, 2H).

36

Compound 2: 4-(3-methylbenzoyloxy)butanoic Acid

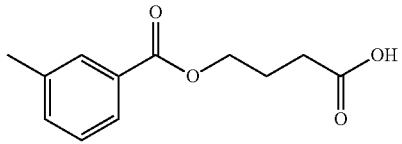 [SMILES: Cc1cccc(C(=O)OCCCC(=O)O)c1]

Jones reagent was added in portions to a stirred mixture of 4-hydroxybutyl 3-methylbenzoate (350 mg, 1.68 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=3:1 to yield the titled compound (333 mg, 89%) as a colorless oil. $^1H$ NMR was performed at 400 MHz with $CDCl_3$ as solvent to characterize the titled compound, results are as follows: δ=7.83-7.81 (m, 2H), 7.36-7.28 (m, 2H), 4.36 (t, J=6.2 Hz, 2H), 2.53 (t, J=7.2 Hz, 2H), 2.38 (s, 3H), 2.14-2.07 (m, 2H).

Example 1-3

Intermediate Compound 3': 4-hydroxybutyl 4-methylbenzoate

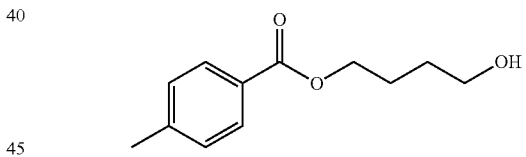

A solution of 4-methylbenzoyl chloride (616 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (470 mg, 56%) as a colorless oil. $^1H$ NMR was performed at 400 MHz with $CDCl_3$ as solvent to characterize the titled compound, results are as follows: δ=7.91 (d, J=8.4 Hz, 2H), 7.20 (d, J=8.4 Hz, 2H), 4.32 (t, J=6.6 Hz, 2H), 3.69 (t, J=6.6 Hz, 2H), 2.38 (s, 3H), 2.19 (br. s., 1H), 1.87-1.80 (m, 2H), 1.74-1.67 (m, 2H).

Compound 3: 4-(4-methylbenzoyloxy)butanoic Acid

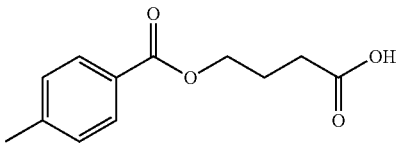 [SMILES: Cc1ccc(C(=O)OCCCC(=O)O)cc1]

Jones reagent was added in portions to a stirred mixture of 4-hydroxybutyl 4-methylbenzoate (400 mg, 1.92 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=3:1 to yield the titled compound (364 mg, 85%) as crystalline solids. $^1$H NMR was performed at 400 MHz with $CDCl_3$ as solvent to characterize the titled compound, results are as follows: δ=7.91 (d, J=8.0 Hz, 2H), 7.23 (d, J=8.0 Hz, 2H), 4.36 (t, J=6.2 Hz, 2H), 2.54 (t, J=7.4 Hz, 2H), 2.40 (s, 3H), 2.14-2.08 (m, 2H).

Compound 4: 4-(4-fluorobenzoyloxy)butanoic Acid

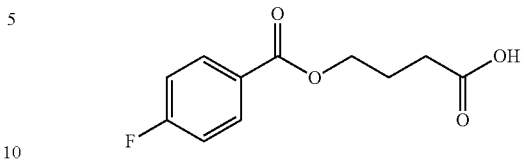

Jones reagent was added in portions to a stirred mixture of 4-hydroxybutyl 4-fluorobenzoate (500 mg, 2.36 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=5:1 to yield the titled compound (356 mg, 67%) as crystalline solids. $^1$H NMR was performed at 400 MHz with $CDCl_3$ as solvent to characterize the titled compound, results are as follows: δ=8.06-8.03 (m, 2H), 7.11 (t, J=8.6 Hz, 2H), 4.38 (t, J=6.4 Hz, 2H), 2.54 (t, J=7.2 Hz, 2H), 2.15-2.07 (m, 2H).

Example 1-4

Intermediate Compound 4': 4-hydroxybutyl 4-fluorobenzoate

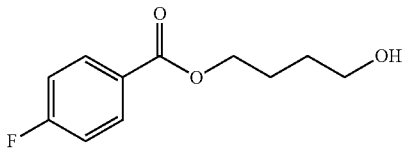 [SMILES: O=C(OCCCCO)c1ccc(F)cc1]

A solution of 4-fluorobenzoyl chloride (632 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (540 mg, 64%) as a colorless oil. $^1$H NMR was performed at 400 MHz with $CDCl_3$ as solvent to characterize the titled compound, results are as follows: δ=8.07-8.04 (m, 2H), 7.11 (t, J=8.6 Hz, 2H), 4.36 (t, J=6.4 Hz, 2H), 3.73 (t, J=6.4 Hz, 2H), 1.90-1.83 (m, 2H), 1.76-1.69 (m, 2H), 1.41 (br. s., 1H).

Example 1-5

Intermediate Compound 5': 4-hydroxybutyl 2,4,6-trimethylbenzoate

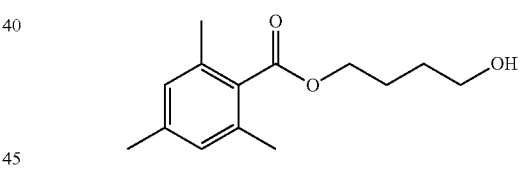

A solution of 2,4,6-trimethylbenzoyl chloride (728 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. was added a solution of 2,4,6-trimethylbenzoyl chloride (728 mg, 4 mmol) in DCM (5 mL) dropwise during 10 min. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (600 mg, 64%) as a colorless oil. $^1$H NMR was performed at 400 MHz with $CDCl_3$ as solvent to characterize the titled compound, results are as follows: δ=6.85 (s, 2H), 4.34 (t, J=6.6 Hz, 2H), 3.69 (t, J=6.6 Hz, 2H), 2.29 (s, 6H), 2.28 (s, 3H), 1.88-1.80 (m, 2H), 1.73-1.66 (m, 2H), 1.49 (br. s., 1H).

Compound 5:
4-(2,4,6-trimethylbenzoyloxy)butanoic Acid

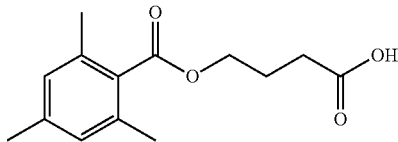 [SMILES: Cc1cc(C)c(C(=O)OCCCC(=O)O)c(C)c1]

Jones reagent was added in portions to a stirred mixture of 4-hydroxybutyl 2,4,6-trimethylbenzoate (500 mg, 2.12 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=5:1-3:1 to yield the titled compound (450 mg, 85%) as a white solid. $^1$H NMR was performed at 400 MHz with $CDCl_3$ as solvent to characterize the titled compound, results are as follows: δ=6.85 (s, 2H), 4.36 (t, J=6.4 Hz, 2H), 2.51 (t, J=7.2 Hz, 2H), 2.29 (s, 6H), 2.28 (s, 3H), 2.12-2.05 (m, 2H).

Example 1-6

Intermediate Compound 6': 4-hydroxybutyl 2-methoxybenzoate

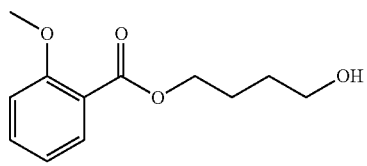 [SMILES: COc1ccccc1C(=O)OCCCCO]

A solution of 2-methoxybenzoyl chloride (680 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (370 mg, 41%) as a colorless oil. $^1$H NMR was performed at 400 MHz with $CDCl_3$ as solvent to characterize the titled compound, results are as follows: δ=7.79 (dd, J=1.6, 7.6 Hz, 1H), 7.49-7.45 (m, 1H), 7.00-6.97 (m, 2H), 4.35 (t, J=6.2 Hz, 2H), 3.90 (s, 3H), 3.77-3.68 (m, 2H), 1.91-1.83 (m, 2H), 1.77-1.69 (m, 2H), 1.56 (br. s., 1H).

Compound 6: 4-(2-methoxybenzoyloxy)butanoic Acid

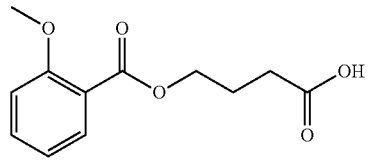 [SMILES: COc1ccccc1C(=O)OCCCC(=O)O]

Jones reagent was added in portions to a stirred mixture of 4-hydroxybutyl 2-methoxybenzoate (300 mg, 1.34 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (244 mg, 76%) as crystalline solids. $^1$H NMR was performed at 400 MHz with $CDCl_3$ as solvent to characterize the titled compound, results are as follows: δ=7.78 (dd, J=1.8, 7.8 Hz, 1H), 7.49-7.45 (m, 1H), 7.00-6.96 (m, 2H), 4.36 (t, J=6.0 Hz, 2H), 3.90 (s, 3H), 2.57 (t, J=7.4 Hz, 2H), 2.13-2.07 (m, 2H).

Example 1-7

Intermediate Compound 7': 4-hydroxybutyl 3-methoxybenzoate

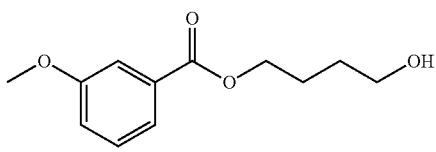 [SMILES: COc1cccc(C(=O)OCCCCO)c1]

A solution of 3-methoxybenzoyl chloride (680 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (420 mg, 47%) as a colorless oil. $^1$H NMR was performed at 400 MHz with $CDCl_3$ as solvent to characterize the titled compound, results are as follows: δ=7.63 (d, J=7.6 Hz, 1H), 7.56 (s, 1H), 7.34 (t, J=8.0 Hz, 1H), 7.10 (dd, J=2.4, 8.0 Hz, 1H), 4.36 (t, J=6.4 Hz, 2H), 3.85 (s, 3H), 3.73 (t, J=6.2 Hz, 2H), 1.91-1.84 (m, 2H), 1.76-1.69 (m, 2H).

Compound 7: 4-(3-methoxybenzoyloxy)butanoic Acid

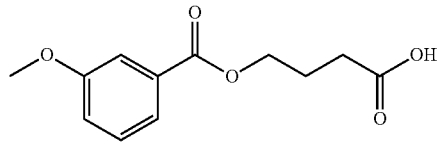 [SMILES: COc1cccc(C(=O)OCCCC(=O)O)c1]

Jones reagent was added in portions to a stirred mixture of 4-hydroxybutyl 3-methoxybenzoate (350 mg, 1.56 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=8:1-3:1 to yield the titled compound (287 mg, 77%) as crystalline solids. $^1$H NMR was performed at 400 MHz with $CDCl_3$ as solvent to characterize the titled compound, results are as follows: δ=7.63 (d, J=8.0 Hz, 1H), 7.55 (s, 1H), 7.35 (t, J=7.8 Hz, 1H), 7.10 (dd, J=2.4, 8.0 Hz, 1H), 4.39 (t, J=6.4 Hz, 2H), 3.86 (s, 3H), 2.54 (t, J=7.2 Hz, 2H), 2.16-2.08 (m, 2H).

Example 1-8

Intermediate Compound 8': 4-hydroxybutyl 4-methoxybenzoate

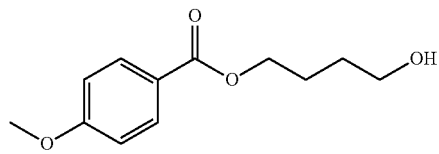 [SMILES: COc1ccc(C(=O)OCCCCO)cc1]

A solution of 4-methoxybenzoyl chloride (680 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (500 mg, 56%) as a colorless oil. $^1$H NMR was performed at 400 MHz with $CDCl_3$ as solvent to characterize the titled compound, results are as follows: δ=7.99 (d, J=9.2 Hz, 2H), 6.91 (d, J=8.8 Hz, 2H), 4.33 (t, J=6.6 Hz, 2H), 3.86 (s, 3H), 3.73 (s, 2H), 1.89-1.82 (m, 2H), 1.76-1.69 (m, 2H), 1.44 (br. s., 1H).

Compound 8: 4-(4-methoxybenzoyloxy)butanoic Acid

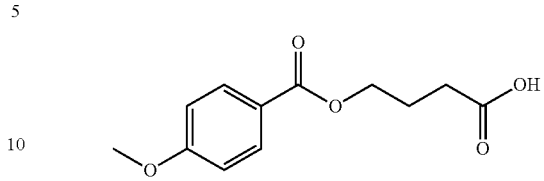

Jones reagent was added in portions to a stirred mixture of 4-hydroxybutyl 4-methoxybenzoate (400 mg, 1.79 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (370 mg, 87%) as a white solid. $^1$H NMR was performed at 400 MHz with $CDCl_3$ as solvent to characterize the titled compound, results are as follows: δ=7.99 (d, J=9.2 Hz, 2H), 6.92 (d, J=8.8 Hz, 2H), 4.35 (t, J=6.2 Hz, 2H), 3.86 (s, 3H), 2.54 (t, J=7.2 Hz, 2H), 2.13-2.08 (m, 2H).

Example 1-9

Intermediate Compound 9': 4-hydroxybutyl 2-chlorobenzoate

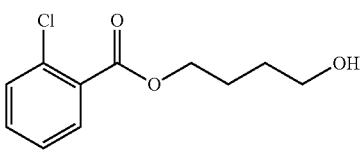 [SMILES: O=C(OCCCCO)c1ccccc1Cl]

A solution of 2-chlorobenzoyl chloride (2 g, 11.43 mmol) in DCM (10 mL) was added dropwise during 10 min to a stirred solution of butane-1,4-diol (3085 mg, 34.28 mmol) and $Et_3N$ (2308 mg, 22.85 mmol) in DCM (50 mL) at 0° C. The reaction was allowed to warm up gradually and stirred at 0-25° C. over 16 h. After that, the reaction mixture was diluted with $H_2O$ (30 mL) and stirred for 5 min. The aqueous phase was separated and extracted with DCM (10 mL). The combined organic phase was washed with brine (20 mL), dried over $Na_2SO_4$ and evaporated. The residue was purified by a silica gel flash column with Hex/EA=8:1 to yield the titled compound (1.8 g, 69%) as colorless oil $^1$H NMR was performed at 400 MHz with $CDCl_3$ as solvent to characterize the titled compound, results are as follows: δ=7.81 (dd, J=1.4, 7.8 Hz, 1H), 7.45-7.38 (m, 2H), 7.34-7.28 (m, 1H), 4.38 (t, J=6.4 Hz, 2H), 3.71 (t, J=6.4 Hz, 2H), 1.91-1.84 (m, 2H), 1.77-1.70 (m, 2H).

Compound 9: 4-(2-chlorobenzoyloxy)butanoic Acid

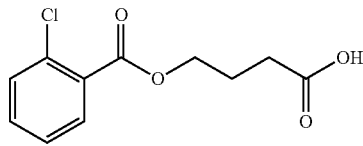 [SMILES: O=C(O)CCCOC(=O)c1ccccc1Cl]

Jones reagent was added in portions to a stirred mixture of 4-hydroxybutyl 2-chlorobenzoate (1.6 g, 7.02 mmol) and Celite® (diatomaceous earth, 2 g) in acetone (10 mL) at 0° C. The reaction proceeded at 0° C. over 1 h and the reaction progress was monitored by TLC. After completion, the reaction was quenched with drops of iPrOH, diluted with EA (20 mL) and then filtered. The filtered cake was washed with EA (5 mL) and the combined filtrate was washed with brine (3 mL×2), dried over $Na_2SO_4$ and concentrated. The residue was purified by a silica gel flash column with Hex/EA=3:1 to yield the titled compound (1 g, 59%) as crystalline solids. $^1H$ NMR was performed at 400 MHz with $CDCl_3$ as solvent to characterize the titled compound, results are as follows: δ=7.82 (dd, J=1.2, 8.0 Hz, 1H), 7.49-7.38 (m, 2H), 7.34-7.29 (m, 1H), 4.41 (t, J=6.2 Hz, 2H), 2.57 (t, J=7.2 Hz, 2H), 2.16-2.09 (m, 2H).

Example 1-10

Intermediate Compound 10': 4-hydroxybutyl 3-chlorobenzoate

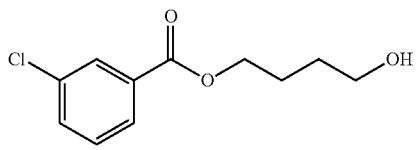 [SMILES: O=C(OCCCCO)c1cccc(Cl)c1]

A solution of 3-chlorobenzoyl chloride (696 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (550 mg, 60%) as a colorless oil. $^1H$ NMR was performed at 400 MHz with $CDCl_3$ as solvent to characterize the titled compound, results are as follows: δ=8.00 (s, 1H), 7.92 (d, J=7.6 Hz, 1H), 7.52 (dd, J=0.8, 8.4 Hz, 1H), 7.38 (t, J=7.8 Hz, 1H), 4.36 (t, J=6.4 Hz, 2H), 3.73 (dd, J=6.2, 10.6 Hz, 2H), 1.91-1.84 (m, 2H), 1.76-1.69 (m, 3H).

Compound 10: 4-(3-chlorobenzoyloxy)butanoic Acid

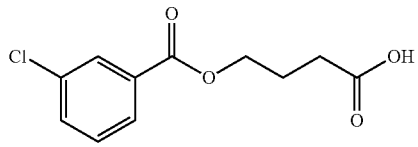 [SMILES: O=C(O)CCCOC(=O)c1cccc(Cl)c1]

Jones reagent was added in portions to a stirred mixture of 4-hydroxybutyl 3-chlorobenzoate (500 mg, 2.19 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (420 mg, 79%) as a colorless oil. $^1H$ NMR was performed at 400 MHz with $CDCl_3$ as solvent to characterize the titled compound, results are as follows: δ=8.00 (s, 1H), 7.92 (d, J=7.6 Hz, 1H), 7.55-7.52 (m, 1H), 7.39 (t, J=7.8 Hz, 1H), 4.39 (t, J=6.2 Hz, 2H), 2.55 (t, J=7.2 Hz, 2H), 2.16-2.09 (m, 2H).

Example 1-11

Intermediate Compound 11': 4-hydroxybutyl 4-chlorobenzoate

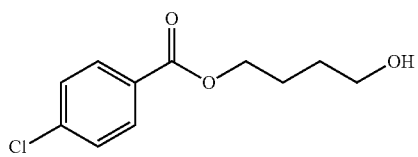 [SMILES: O=C(OCCCCO)c1ccc(Cl)cc1]

A solution of 4-chlorobenzoyl chloride (2 g, 11.43 mmol) in DCM (10 mL) was added dropwise during 10 min to a stirred solution of butane-1,4-diol (3085 mg, 34.28 mmol) and $Et_3N$ (2308 mg, 22.85 mmol) in DCM (50 mL) at 0° C. The reaction was allowed to warm up gradually and stirred at 0-25° C. over 1 h. After that, the reaction mixture was diluted with $H_2O$ (30 mL) and stirred for 5 min. The aqueous phase was separated and extracted with DCM (10 mL). The combined organic phase was washed with brine (20 mL), dried over $Na_2SO_4$ and evaporated. The residue was purified by a silica gel flash column with Hex/EA=7:1 to yield the titled compound (1.6 g, 62%) as crystalline solids $^1H$ NMR was performed at 400 MHz with $CDCl_3$ as solvent to characterize the titled compound, results are as follows: δ=7.97 (d, J=8.4 Hz, 2H), 7.41 (d, J=8.4 Hz, 2H), 4.36 (t, J=6.6 Hz, 2H), 3.73 (t, J=6.4 Hz, 2H), 1.90-1.84 (m, 2H), 1.75-1.69 (m, 2H).

Compound 11: 4-(4-chlorobenzoyloxy)butanoic Acid

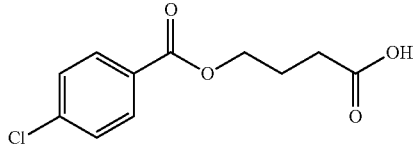 [SMILES: O=C(O)CCCOC(=O)c1ccc(Cl)cc1]

Jones reagent was added in portions to a stirred mixture of 4-hydroxybutyl 4-chlorobenzoate (1.5 g, 6.58 mmol) and Celite® (diatomaceous earth, 2 g) in acetone (10 mL) at 0° C. The reaction proceeded at 0° C. over 16 h and the reaction progress was monitored by TLC. After completion, the reaction was quenched with drops of iPrOH, diluted with EA (20 mL) and then filtered. The filtered cake was washed with EA (5 mL) and the combined filtrate was washed with brine (3 mL×2), dried over $Na_2SO_4$ and concentrated. The residue was purified by a silica gel flash column with Hex/EA=3:1 to afford the title compound (600 mg, 38%) as crystalline solids. $^1$H NMR was performed at 400 MHz with $CDCl_3$ as solvent to characterize the titled compound, results are as follows: δ=7.96 (d, J=8.0 Hz, 2H), 7.41 (d, J=8.0 Hz, 2H), 4.39 (t, J=6.2 Hz, 2H), 2.54 (t, J=7.2 Hz, 2H), 2.15-2.07 (m, 2H).

Compound 12: 4-(3-cyanobenzoyloxy)butanoic Acid

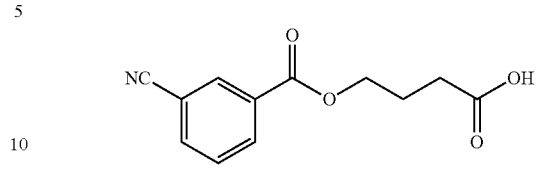

Jones reagent was added in portions to a stirred mixture of 4-hydroxybutyl 3-cyanobenzoate (400 mg, 1.83 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (330 mg, 77%) as a white solid. $^1$H NMR was performed at 400 MHz with $CDCl_3$ as solvent to characterize the titled compound, results are as follows: δ=8.31 (s, 1H), 8.26 (d, J=8.0 Hz, 1H), 7.85 (d, J=7.6 Hz, 1H), 7.59 (t, J=7.8 Hz, 1H), 4.43 (t, J=6.4 Hz, 2H), 2.56 (t, J=7.2 Hz, 2H), 2.18-2.11 (m, 2H).

Example 1-12

Intermediate Compound 12': 4-hydroxybutyl 3-cyanobenzoate

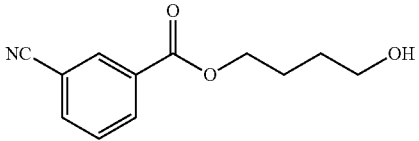 [SMILES: N#Cc1cccc(C(=O)OCCCCO)c1]

A solution of 3-cyanobenzoyl chloride (660 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (450 mg, 51%) as a colorless oil. $^1$H NMR was performed at 400 MHz with $CDCl_3$ as solvent to characterize the titled compound, results are as follows: δ=8.31 (s, 1H), 8.26 (d, J=8.0 Hz, 1H), 7.83 (d, J=7.6 Hz, 1H), 7.58 (t, J=8.0 Hz, 1H), 4.39 (t, J=6.4 Hz, 2H), 3.73 (t, J=6.4 Hz, 2H), 1.92-1.85 (m, 2H), 1.76-1.69 (m, 2H).

Example 1-13

Intermediate Compound 13': 4-hydroxybutyl 4-tert-butylbenzoate

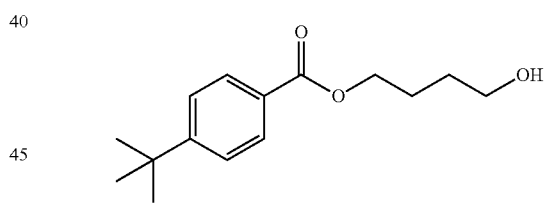

A solution of 4-tert-butylbenzoyl chloride (784 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (530 mg, 53%) as a colorless oil. $^1$H NMR was performed at 400 MHz with $CDCl_3$ as solvent to characterize the titled compound, results are as follows: δ=7.97 (d, J=8.0 Hz, 2H), 7.45 (d, J=8.8 Hz, 2H), 4.35 (t, J=6.4 Hz, 2H), 3.73 (t, J=6.2 Hz, 2H), 1.91-1.83 (m, 2H), 1.76-1.71 (m, 2H), 1.34 (s, 9H).

Compound 13: 4-(4-tert-butylbenzoyloxy)butanoic Acid

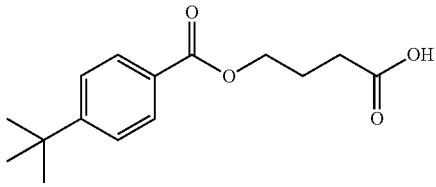 [SMILES: CC(C)(C)c1ccc(C(=O)OCCCC(=O)O)cc1]

Jones reagent was added in portions to a stirred mixture of 4-hydroxybutyl 4-tert-butylbenzoate (450 mg, 1.8 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (370 mg, 79%) as a white solid. $^1$H NMR was performed at 400 MHz with $CDCl_3$ as solvent to characterize the titled compound, results are as follows: δ=7.96 (d, J=8.4 Hz, 2H), 7.45 (d, J=8.8 Hz, 2H), 4.37 (t, J=6.2 Hz, 2H), 2.55 (t, J=7.4 Hz, 2H), 2.15-2.06 (m, 2H), 1.34 (s, 9H).

Example 1-14

Intermediate Compound 14': 4-hydroxybutyl 3-(trifluoromethyl)benzoate

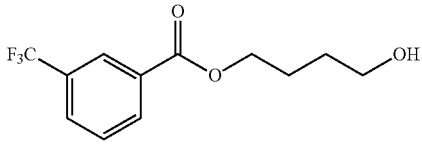 [SMILES: O=C(OCCCCO)c1cccc(C(F)(F)F)c1]

A solution of 3-(trifluoromethyl)benzoyl chloride (832 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. over 12 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-5:1 to yield the titled compound (670 mg, 64%) as a colorless oil. $^1$H NMR was performed at 400 MHz with $CDCl_3$ as solvent to characterize the titled compound, results are as follows: δ=8.29 (s, 1H), 8.23 (d, J=8.0 Hz, 1H), 7.82 (d, J=8.0 Hz, 1H), 7.59 (t, J=7.8 Hz, 1H), 4.40 (t, J=6.4 Hz, 2H), 3.74 (t, J=6.6 Hz, 2H), 1.93-1.86 (m, 2H), 1.77-1.70 (m, 2H), 1.42 (br. s., 1H).

Compound 14: 4-(3-(trifluoromethyl)benzoyloxy)butanoic Acid

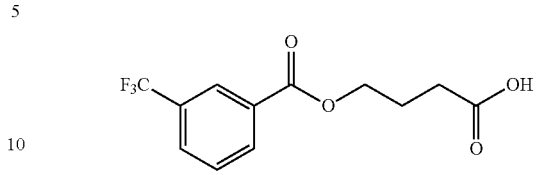

Jones reagent was added in portions to a stirred mixture of 4-hydroxybutyl 3-(trifluoromethyl)benzoate (600 mg, 2.29 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-3:1 to yield the titled compound (400 mg, 63%) as a colorless oil. $^1$H NMR was performed at 400 MHz with $CDCl_3$ as solvent to characterize the titled compound, results are as follows: δ=8.29 (s, 1H), 8.22 (d, J=8.0 Hz, 1H), 7.82 (d, J=7.6 Hz, 1H), 7.59 (t, J=7.6 Hz, 1H), 4.43 (t, J=6.4 Hz, 2H), 2.55 (t, J=7.4 Hz, 2H), 2.18-2.12 (m, 2H).

Example 1-15

Intermediate Compound 15': 4-hydroxybutyl 3,4,5-trimethoxybenzoate

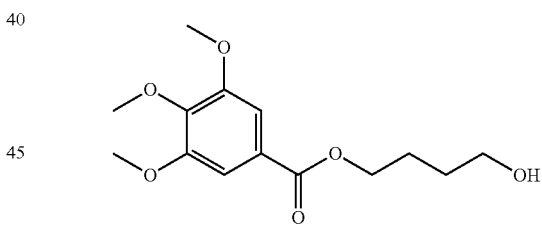

A solution of 3,4,5-trimethoxybenzoyl chloride (920 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. over 12 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-4:1 to yield the titled compound (700 mg, 62%) as a colorless oil. $^1$H NMR was performed at 400 MHz with $CDCl_3$ as solvent to characterize the titled compound, results are as follows: δ=7.29 (s, 2H), 4.35 (t, J=6.6 Hz, 2H), 3.90 (s, 9H), 3.77-3.69 (m, 2H), 1.92-1.84 (m, 2H), 1.75-1.68 (m, 2H), 1.48 (br. s., 1H).

Compound 15:
4-(3,4,5-trimethoxybenzoyloxy)butanoic Acid

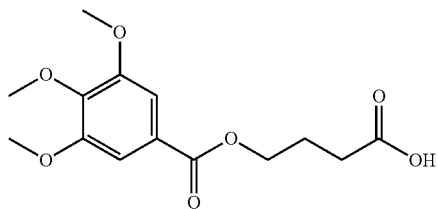 [SMILES: COc1cc(C(=O)OCCCC(=O)O)cc(OC)c1OC]

Jones reagent was added in portions to a stirred mixture of 4-hydroxybutyl 3,4,5-trimethoxybenzoate (600 mg, 2.11 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=8:1-3:1 to yield the titled compound (440 mg, 70%) as crystalline solids. $^1$H NMR was performed at 400 MHz with $CDCl_3$ as solvent to characterize the titled compound, results are as follows: δ=7.28 (s, 2H), 4.37 (t, J=6.4 Hz, 2H), 3.90 (s, 9H), 2.52 (t, J=7.2 Hz, 2H), 2.15-2.08 (m, 2H).

Example 1-16

Intermediate Compound 16': 4-hydroxybutyl 4-ethylbenzoate

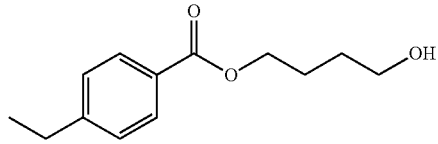 [SMILES: CCc1ccc(C(=O)OCCCCO)cc1]

A solution of 4-ethylbenzoyl chloride (500 mg, 2.98 mmol) in DCM (5 mL) was added dropwise during 10 min to a stirred solution of butane-1,4-diol (534 mg, 5.93 mmol) and $Et_3N$ (599 mg, 5.93 mmol) in DCM (10 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-6:1 to yield the titled compound (450 mg, 68%) as a colorless oil. $^1$H NMR was performed at 400 MHz with $CDCl_3$ as solvent to characterize the titled compound, results are as follows: δ=7.97 (s, 1H), 7.94 (s, 1H), 7.27 (s, 1H), 7.25 (s, 1H), 4.35 (t, J=6.4 Hz, 2H), 3.73 (t, J=6.2 Hz, 2H), 2.70 (q, J=7.6 Hz, 2H), 1.90-1.83 (m, 2H), 1.77-1.70 (m, 2H), 1.34 (br. s., 1H), 1.25 (t, J=7.6 Hz, 3H).

Compound 16: 4-(4-ethylbenzoyloxy)butanoic Acid

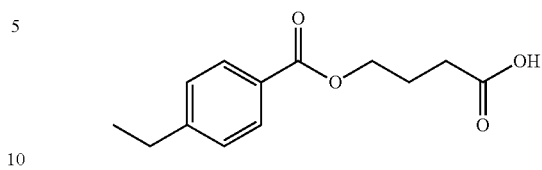

Jones reagent was added in portions to a stirred mixture of 4-hydroxybutyl 4-ethylbenzoate (450 mg, 2.03 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (270 mg, 56%) as a colorless oil. $^1$H NMR was performed at 400 MHz with $CDCl_3$ as solvent to characterize the titled compound, results are as follows: δ=7.96 (s, 1H), 7.94 (s, 1H), 7.27 (s, 1H), 7.25 (s, 1H), 4.37 (t, J=6.2 Hz, 2H), 2.70 (q, J=7.6 Hz, 2H), 2.55 (t, J=7.4 Hz, 2H), 2.15-2.09 (m, 2H), 1.25 (t, J=7.6 Hz, 3H).

Example 1-17

Intermediate Compound 17': 4-hydroxybutyl 2,3-dimethylbenzoate

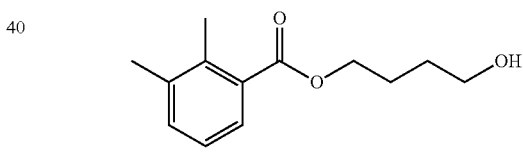

A solution of 2,3-dimethylbenzoyl chloride (500 mg, 2.97 mmol) in DCM (5 mL) was added dropwise during 10 min to a stirred solution of butane-1,4-diol (534 mg, 5.93 mmol) and $Et_3N$ (599 mg, 5.93 mmol) in DCM (10 mL) at 0° C. The reaction was allowed to warm up gradually and stirred at 0-25° C. over 3 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=7:1 to yield the titled compound (390 mg, 59%) as a colorless oil. $^1$H NMR was performed at 400 MHz with $CDCl_3$ as solvent to characterize the titled compound, results are as follows: δ=7.61 (d, J=7.6 Hz, 1H), 7.28 (d, J=7.6 Hz, 1H), 7.13 (t, J=7.8 Hz, 1H), 4.34 (t, J=6.6 Hz, 2H), 3.73 (t, J=6.0 Hz, 2H), 2.45 (s, 3H), 2.32 (s, 3H), 1.90-1.83 (m, 2H), 1.78-1.69 (m, 2H), 1.36 (br. s., 1H).

Compound 17: 4-(2,3-dimethylbenzoyloxy)butanoic Acid

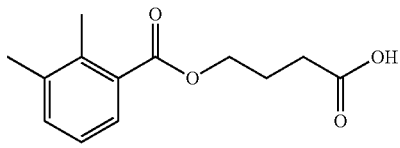 [SMILES: Cc1cccc(C(=O)OCCCC(=O)O)c1C]

Jones reagent was added in portions to a stirred mixture of 4-hydroxybutyl 2,3-dimethylbenzoate (350 mg, 1.58 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-6:1 to yield the titled compound (230 mg, 62%) as a white solid. $^1$H NMR was performed at 400 MHz with $CDCl_3$ as solvent to characterize the titled compound, results are as follows: δ=7.61 (d, J=7.6 Hz, 1H), 7.28 (d, J=7.2 Hz, 1H), 7.13 (t, J=7.6 Hz, 1H), 4.35 (t, J=6.2 Hz, 2H), 2.54 (t, J=7.2 Hz, 2H), 2.45 (s, 3H), 2.32 (s, 3H), 2.15-2.08 (m, 2H).

Example 1-18

Intermediate Compound 18': 4-hydroxybutyl 3,5-dimethoxybenzoate

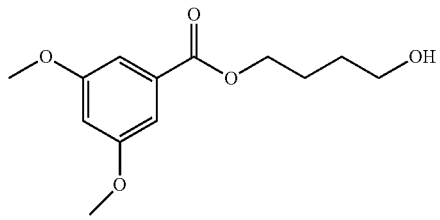 [SMILES: COc1cc(OC)cc(C(=O)OCCCCO)c1]

A solution of 3,5-dimethoxybenzoyl chloride (500 mg, 2.49 mmol) in DCM (5 mL) was added dropwise during 10 min to a stirred solution of butane-1,4-diol (450 mg, 5 mmol) and $Et_3N$ (505 mg, 5 mmol) in DCM (10 mL) at 0° C. The reaction was allowed to warm up gradually and stirred at 0-25° C. over 3 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=7:1 to yield the titled compound (430 mg, 68%) as a colorless oil. $^1$H NMR was performed at 400 MHz with $CDCl_3$ as solvent to characterize the titled compound, results are as follows: δ=7.18 (d, J=2.4 Hz, 2H), 6.65 (t, J=2.0 Hz, 1H), 4.36 (t, J=6.4 Hz, 2H), 3.83 (s, 6H), 3.73 (t, J=6.2 Hz, 2H), 1.90-1.83 (m, 2H), 1.76-1.69 (m, 2H).

Compound 18: 4-(3,5-dimethoxybenzoyloxy)butanoic Acid

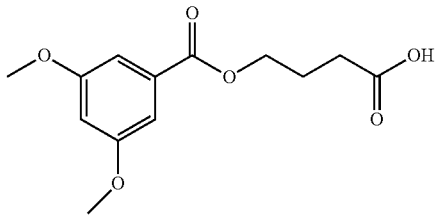 [SMILES: COc1cc(OC)cc(C(=O)OCCCC(=O)O)c1]

Jones reagent was added in portions to a stirred mixture of 4-hydroxybutyl 3,5-dimethoxybenzoate (400 mg, 1.57 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (200 mg, 47%) as a white solid. $^1$H NMR was performed at 400 MHz with $CDCl_3$ as solvent to characterize the titled compound, results are as follows: δ=7.16 (d, J=2.4 Hz, 2H), 6.64 (t, J=2.0 Hz, 1H), 4.37 (t, J=6.2 Hz, 2H), 3.82 (s, 6H), 2.52 (t, J=7.2 Hz, 2H), 2.14-2.07 (m, 2H).

Example 1-19

Intermediate Compound 19': 4-hydroxybutyl 3,5-dimethylbenzoate

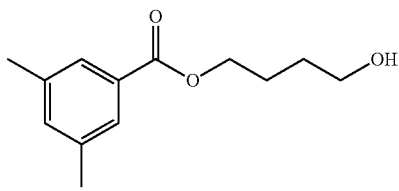 [SMILES: Cc1cc(C)cc(C(=O)OCCCCO)c1]

A solution of 3,5-dimethylbenzoyl chloride (500 mg, 2.96 mmol) in DCM (5 mL) was added dropwise during 10 min to a stirred solution of butane-1,4-diol (534 mg, 5.93 mmol) and $Et_3N$ (599 mg, 5.93 mmol) in DCM (10 mL) at 0° C. The reaction was allowed to warm up gradually and stirred at 0-25° C. over 16 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=7:1 to yield the titled compound (400 mg, 61%) as a colorless oil. $^1$H NMR was performed at 400 MHz with $CDCl_3$ as solvent to characterize the titled compound, results are as follows: =7.65 (s, 2H), 7.19 (s, 1H), 4.35 (t, J=6.4 Hz, 2H), 3.73 (s, 2H), 2.36 (s, 6H), 1.90-1.83 (m, 2H), 1.77-1.70 (m, 2H).

Compound 19: 4-(3,5-dimethylbenzoyloxy)butanoic Acid

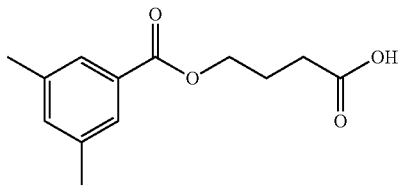 [SMILES: Cc1cc(C)cc(C(=O)OCCCC(=O)O)c1]

Jones reagent was added in portions to a stirred mixture of 4-hydroxybutyl 3,5-dimethylbenzoate (400 mg, 1.8 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (300 mg, 70%) as a white solid. $^1H$ NMR was performed at 400 MHz with $CDCl_3$ as solvent to characterize the titled compound, results are as follows: δ=7.64 (s, 2H), 7.19 (s, 1H), 4.36 (t, J=6.0 Hz, 2H), 2.55 (t, J=7.4 Hz, 2H), 2.36 (s, 6H), 2.15-2.08 (m, 2H).

Compound 20: (E)-4-(cinnamoyloxy)butanoic Acid

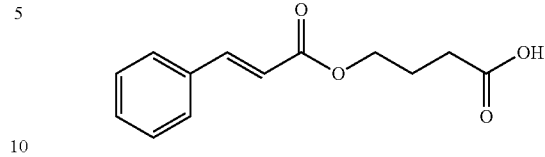

Jones reagent was added in portions to a stirred mixture of 4-hydroxybutyl cinnamate (400 mg, 1.81 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=3:1 to yield the titled compound (370 mg, 87%) as colorless oil. $^1H$ NMR was performed at 400 MHz with $CDCl_3$ as solvent to characterize the titled compound, results are as follows: δ=7.68 (d, J=16.0 Hz, 1H), 7.54-7.52 (m, 2H), 7.40-7.38 (m, 3H), 6.43 (d, J=16.0 Hz, 1H), 4.26 (t, J=6.2 Hz, 2H), 2.48 (t, J=7.2 Hz, 2H), 2.07-2.01 (m, 2H).

Example 1-20

Intermediate Compound 20': 4-hydroxybutyl cinnamate

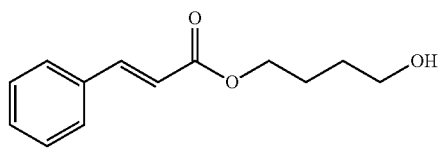 [SMILES: O=C(/C=C/c1ccccc1)OCCCCO]

A solution of cinnamoyl chloride (664 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (455 mg, 52%) as a colorless oil. $^1H$ NMR was performed at 400 MHz with $CDCl_3$ as solvent to characterize the titled compound, results are as follows: δ=7.69 (d, J=16.0 Hz, 1H), 7.54-7.52 (m, 2H), 7.39 (t, J=3.2 Hz, 3H), 6.44 (d, J=16.0 Hz, 1H), 4.25 (t, J=6.4 Hz, 2H), 3.72 (t, J=6.2 Hz, 2H), 1.85-1.78 (m, 2H), 1.73-1.66 (m, 2H), 1.44 (br. s., 1H).

Example 1-21

Intermediate Compound 21': 4-hydroxybutyl 3-phenylpropanoate

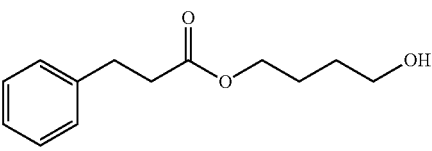 [SMILES: O=C(CCc1ccccc1)OCCCCO]

A solution of 3-phenylpropanoyl chloride (672 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (370 mg, 42%) as a colorless oil. $^1H$ NMR was performed at 400 MHz with $CDCl_3$ as solvent to characterize the titled compound, results are as follows: δ=7.31-7.27 (m, 2H), 7.21-7.19 (m, 3H), 4.10 (t, J=6.6 Hz, 2H), 3.65 (t, J=6.4 Hz, 2H), 2.95 (t, J=7.8 Hz, 2H), 2.63 (t, J=7.6 Hz, 2H), 1.73-1.66 (m, 2H), 1.60-1.54 (m, 2H), 1.33 (br. s., 1H).

Compound 21: 4-(3-phenylpropanoyloxy)butanoic Acid

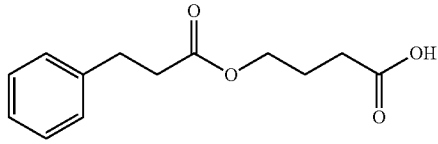 [SMILES: O=C(O)CCCOC(=O)CCc1ccccc1]

Jones reagent was added in portions to a stirred mixture of 4-hydroxybutyl 3-phenylpropanoate (300 mg, 1.35 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=3:1 to yield the titled compound (277 mg, 87%) as colorless oil. $^1H$ NMR was performed at 400 MHz with $CDCl_3$ as solvent to characterize the titled compound, results are as follows: S=7.31-7.27 (m, 2H), 7.22-7.19 (m, 3H), 4.12 (t, J=6.2 Hz, 2H), 2.95 (t, J=7.8 Hz, 2H), 2.63 (t, J=7.6 Hz, 2H), 2.37 (t, J=7.4 Hz, 2H), 1.96-1.90 (m, 2H).

Example 1-22

Intermediate Compound 22': 4-hydroxybutyl pivalate

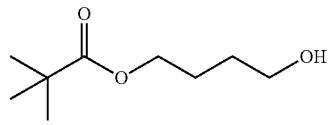

A solution of pivaloyl chloride (1.2 g, 10 mmol) was added dropwise during 10 min to a stirred solution of butane-1,4-diol (2.7 g, 30 mmol) and $Et_3N$ (2.02 g, 20 mmol) in DCM (30 mL) at 0° C. The reaction was allowed to warm up gradually and stirred at 0-25° C. over 1 h. After that, the reaction mixture was diluted with $H_2O$ (10 mL) and stirred for 5 min. The aqueous phase was separated and extracted with DCM (15 mL). The combined organic phase was washed with brine (15 mL), dried over $Na_2SO_4$ and evaporated. The residue was purified by a silica gel flash column with Hex/EA=20:1-5:1 to yield the titled compound (1.5 g, 86%) as a colorless oil. $^1H$ NMR was performed at 400 MHz with $CDCl_3$ as solvent to characterize the titled compound, results are as follows: δ=4.09 (t, J=6.0 Hz, 2H), 3.68 (t, J=6.4 Hz, 2H), 1.74-1.70 (m, 2H), 1.65-1.61 (m, 2H), 1.19 (s, 9H).

Compound 22: 4-(pivaloyloxy)butanoic Acid

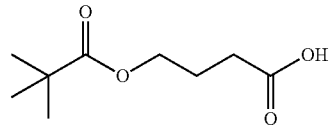

Jones reagent was added in portions to a stirred mixture of 4-hydroxybutyl pivalate (1.0 g, 5.75 mmol) and Celite® (diatomaceous earth, 2 g) in acetone (20 mL) at 0° C. The reaction proceeded at 0° C. over 1 h and the reaction progress was monitored by TLC. After completion, the reaction was quenched with drops of iPrOH, diluted with EA (20 mL) and then filtered. The filtered cake was washed with EA (10 mL) and the combined filtrate was washed with brine (5 mL×2), dried over $Na_2SO_4$ and concentrated. The residue was purified by a silica gel flash column with Hex/EA=5:1 to yield the titled compound (700 mg, 65%) as a colorless oil. $^1H$ NMR was performed at 400 MHz with $CDCl_1$ as solvent to characterize the titled compound, results are as follows: δ=4.11 (t, J=6.4 Hz, 2H), 2.46 (t, J=7.4 Hz, 2H), 2.02-1.95 (m, 2H), 1.19 (s, 9H).

Example 1-23

Intermediate Compound 23': 4-hydroxybutyl 2-ethylbutanoate

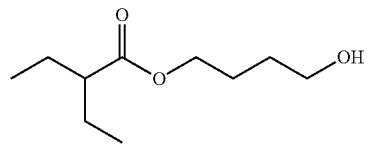

A solution of 2-ethylbutanoyl chloride (500 mg, 3.7 mmol) in DCM (5 mL) was added dropwise during 10 min to a stirred solution of butane-1,4-diol (669 mg, 7.43 mmol) and $Et_3N$ (750 mg, 7.43 mmol) in DCM (10 mL) at 0° C. The reaction was allowed to warm up gradually and stirred at 0-25° C. over 3 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=6:1 to yield the titled compound (450 mg, 65%) as a colorless oil. $^1H$ NMR was performed at 400 MHz with $CDCl_3$ as solvent to characterize the titled compound, results are as follows: δ=4.13 (t, J=6.4 Hz, 2H), 3.73-3.64 (m, 2H), 2.23-2.16 (m, 1H), 1.77-1.70 (m, 2H), 1.68-1.58 (m, 4H), 1.55-1.46 (m, 2H), 0.89 (t, J=7.4 Hz, 6H).

Compound 23: 4-(2-ethylbutanoyloxy)butanoic Acid

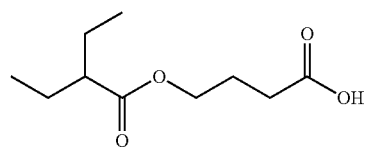

Jones reagent was added in portions to a stirred mixture of 4-hydroxybutyl 2-ethylbutanoate (450 mg, 2.39 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (300 mg, 62%) as a colorless oil. $^1$H NMR was performed at 400 MHz with $CDCl_3$ as solvent to characterize the titled compound, results are as follows: δ=4.14 (t, J=6.2 Hz, 2H), 2.46 (t, J=7.6 Hz, 2H), 2.24-2.17 (m, 1H), 2.02-1.95 (m, 2H), 1.66-1.46 (m, 4H), 0.89 (t, J=7.4 Hz, 6H).

Example 1-24

Intermediate Compound 24': 4-hydroxybutyl 2-propylpentanoate

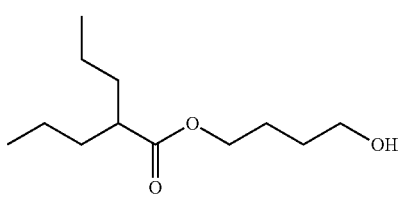

A solution of 2-propylpentanoyl chloride (1 g, 6.13 mmol) in DCM (5 mL) was added dropwise during 10 min to a stirred solution of butane-1,4-diol (1107 mg, 12.3 mmol) and $Et_3N$ (1242 mg, 12.3 mmol) in DCM (10 mL) at 0° C. The reaction was allowed to warm up gradually and stirred at 0-25° C. over 16 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=5:1 to yield the titled compound (700 mg, 53%) as a colorless oil. $^1$H NMR was performed at 400 MHz with $CDCl_3$ as solvent to characterize the titled compound, results are as follows: δ=4.11 (t, J=6.6 Hz, 2H), 3.69 (q, J=5.8 Hz, 2H), 2.39-2.32 (m, 1H), 1.77-1.69 (m, 2H), 1.68-1.60 (m, 3H), 1.58-1.53 (m, 1H), 1.45-1.36 (m, 3H), 1.33-1.24 (m, 4H), 0.89 (t, J=7.2 Hz, 6H).

Compound 24: 4-(2-propylpentanoyloxy)butanoic Acid

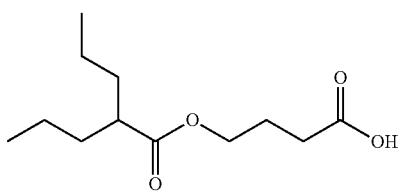 [SMILES: CCCC(CCC)C(=O)OCCCC(=O)O]

Jones reagent was added in portions to a stirred mixture of 4-hydroxybutyl 2-propylpentanoate (500 mg, 2.31 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (160 mg, 30%) as a colorless oil. $^1$H NMR was performed at 400 MHz with $CDCl_3$ as solvent to characterize the titled compound, results are as follows: δ=4.12 (t, J=6.0 Hz, 2H), 2.46 (t, J=7.6 Hz, 2H), 2.41-2.31 (m, 1H), 2.01-1.95 (m, 2H), 1.63-1.54 (m, 2H), 1.45-1.37 (m, 2H), 1.33-1.24 (m, 4H), 0.89 (t, J=7.2 Hz, 6H).

Example 1-25

Intermediate Compound 25': 4-hydroxybutyl cyclopentanecarboxylate

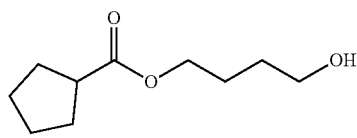 [SMILES: O=C(OCCCCO)C1CCCC1]

A solution of cyclopentanecarbonyl chloride (528 mg, 4 mmol) in DCM (5 mL) was added dropwise during 10 min to a stirred solution of butane-1,4-diol (450 mg, 5 mmol) and $Et_3N$ (505 mg, 5 mmol) in DCM (5 mL) at 0° C. The reaction was allowed to warm up gradually and stirred at 0-25° C. for over 1 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=10:1-3:1 to yield the titled compound (520 mg, 70%) as a colorless oil. $^1$H NMR was performed at 400 MHz with $CDCl_3$ as solvent to characterize the titled compound, results are as follows: δ=4.10 (t, J=6.4 Hz, 2H), 3.68 (t, J=6.0 Hz, 2H), 2.76-2.68 (m, 1H), 1.92-1.62 (m, 10H), 1.60-1.53 (m, 2H), 1.41 (br. s., 1H).

Compound 25: 4-(cyclopentanecarbonyloxy)butanoic Acid

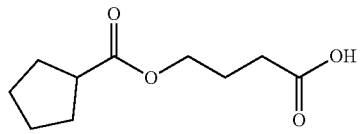 [SMILES: O=C(O)CCCOC(=O)C1CCCC1]

Jones reagent was added in portions to a stirred mixture of 4-hydroxybutyl cyclopentanecarboxylate (450 mg, 2.42 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na₂SO₄ and concentrated. The residue was purified by a silica gel flash column with Hex/EA=3:1 to yield the titled compound (373 mg, 77%) as colorless oil. ¹H NMR was performed at 400 MHz with CDCl₃ as solvent to characterize the titled compound, results are as follows: δ=4 12 (t, J=6.2 Hz, 2H), 2.76-2.68 (m, 1H), 2.45 (t, J=7.2 Hz, 2H), 2.01-1.94 (m, 2H), 1.92-1.84 (m, 2H), 1.82-1.65 (m, 4H), 1.61-1.50 (m, 2H).

Example 1-26

Intermediate Compound 26': 4-hydroxybutyl cyclohexanecarboxylate

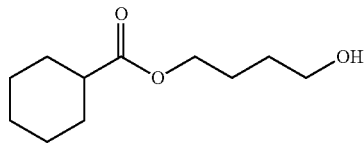 [SMILES: O=C(OCCCCO)C1CCCCC1]

A solution of cyclohexanecarbonyl chloride (584 mg, 4 mmol) in DCM (5 mL) was added dropwise during 10 min to a stirred solution of butane-1,4-diol (450 mg, 5 mmol) and Et₃N (505 mg, 5 mmol) in DCM (5 mL) at 0° C. The reaction was allowed to warm up gradually and stirred at 0-25° C. for over 1 h. After that, the reaction mixture was diluted with H₂O (5 mL) and stirred for 5 min. The aqueous phase was separated and extracted with DCM (5 mL). The combined organic phase was washed with saturated brine (5 mL), dried over anhydrous Na₂SO₄ and evaporated. The residue was purified by a silica gel flash column with Hex/EA=10:1-3:1 to yield the titled compound (440 mg, 55%) as colorless oil. ¹H NMR was performed at 400 MHz with CDCl₃ as solvent to characterize the titled compound, results are as follows: δ=4.08 (t, J=6.2 Hz, 2H), 3.66 (t, J=6.2 Hz, 2H), 2.32-2.24 (m, 1H), 1.88 (d, J=13.2 Hz, 2H), 1.76-1.58 (m, 8H), 1.48-1.37 (m, 2H), 1.31-1.15 (m, 3H).

Compound 26: 4-(cyclohexanecarbonyloxy)butanoic Acid

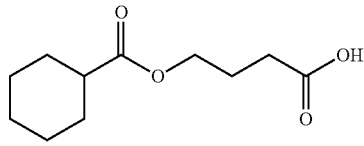 [SMILES: O=C(O)CCCOC(=O)C1CCCCC1]

Jones reagent was added in portions to a stirred mixture of 4-hydroxybutyl cyclohexanecarboxylate (400 mg, 2 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na₂SO₄ and concentrated. The residue was purified by a silica gel flash column with Hex/EA=3:1 to yield the titled compound (350 mg, 82%) as colorless oil. ¹H NMR was performed at 400 MHz with CDCl₃ as solvent to character- ize the titled compound, results are as follows: δ=4.11 (t, J=6.4 Hz, 2H), 2.45 (t, J=7.4 Hz, 2H), 2.29 (tt, J=3.6, 11.3 Hz, 1H), 2.01-1.94 (m, 2H), 1.91-1.87 (m, 2H), 1.76-1.69 (m, 2H), 1.65-1.62 (m, 1H), 1.48-1.38 (m, 2H), 1.33-1.19 (m, 3H).

Example 1-27

Intermediate Compound 27': 4-hydroxybutyl 2-acetoxyacetate

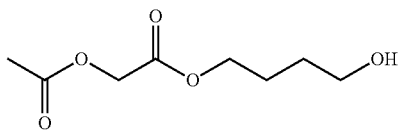

A solution of 2-chloro-2-oxoethyl acetate (544 mg, 4 mmol) in DCM (5 mL) was added dropwise during 10 min to a stirred solution of butane-1,4-diol (450 mg, 5 mmol) and Et₃N (505 mg, 5 mmol) in DCM (5 mL) at 0° C. The reaction was allowed to warm up gradually and stirred at 0-25° C. for over 1 h. After that, the reaction mixture was diluted with H₂O (5 mL) and stirred for 5 min. The aqueous phase was separated and extracted with DCM (5 mL). The combined organic phase was washed with saturated brine (5 mL), dried over anhydrous Na₂SO₄ and evaporated. The residue was purified by a silica gel flash column with Hex/EA=8:1-5:1 to yield the titled compound (500 mg, 66%) as a colorless oil. ¹H NMR was performed at 400 MHz with CDCl₃ as solvent to characterize the titled compound, results are as follows: δ=4.60 (s, 2H), 4.22 (t, J=6.4 Hz, 2H), 3.68 (dd, J=5.8, 10.6 Hz, 2H), 2.16 (s, 3H), 1.81-1.72 (m, 2H), 1.68-1.60 (m, 2H), 1.39 (br. s., 1H).

Compound 27: 4-(2-acetoxyacetoxy)butanoic Acid

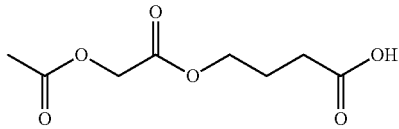

Jones reagent was added in portions to a stirred mixture of 4-hydroxybutyl 2-acetoxyacetate (400 mg, 2.11 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na₂SO₄ and concentrated. The residue was purified by a silica gel flash column with Hex/EA=8:1-3:1 to yield the titled compound (370 mg, 86%) as a colorless oil. ¹H NMR was performed at 400 MHz with CDCl₃ as solvent to characterize the titled compound, results are as follows: δ=4.60 (s, 2H), 4.24 (t, J=6.2 Hz, 2H), 2.46 (t, J=7.4 Hz, 2H), 2.16 (s, 3H), 2.04-1.97 (m, 2H).

Example 1-28

Intermediate Compound 28': ethyl (4-hydroxybutyl) carbonate

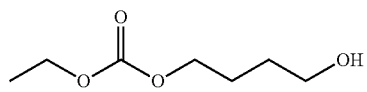

A solution of ethyl carbonochloridate (1 g, 9.17 mmol) in DCM (5 mL) was added dropwise during 10 min to a stirred solution of butane-1,4-diol (1659 mg, 18.43 mmol) and Et$_3$N (1861 mg, 18.43 mmol) in DCM (10 mL) at 0° C. The reaction was allowed to warm up gradually and stirred at 0-25° C. over 16 h. After that, the reaction mixture was diluted with H$_2$O (5 mL) and stirred for 5 min. The aqueous phase was separated and extracted with DCM (5 mL). The combined organic phase was washed with saturated brine (5 mL), dried over anhydrous Na$_2$SO$_4$ and evaporated. The residue was purified by a silica gel flash column with Hex/EA=5:1 to yield the titled compound (700 mg, 47%) as a colorless oil. $^1$H NMR was performed at 400 MHz with CDCl$_3$ as solvent to characterize the titled compound, results are as follows: δ=4.22-4.16 (m, 4H), 3.68 (q, J=5.8 Hz, 2H), 1.81-1.74 (m, 2H), 1.69-1.62 (m, 2H), 1.38 (t, J=5.0 Hz, 1H), 1.31 (t, J=7.0 Hz, 3H).

Compound 28: 4-(ethoxycarbonyloxy)butanoic Acid

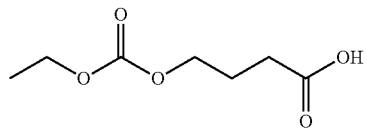

Jones reagent was added in portions to a stirred mixture of ethyl (4-hydroxybutyl) carbonate (500 mg, 3.09 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (70 mg, 13%) as a colorless oil. $^1$H NMR was performed at 400 MHz with CDCl$_3$ as solvent to characterize the titled compound, results are as follows: δ=4.22-4.17 (m, 4H), 2.50 (t, J=7.2 Hz, 2H), 2.05-1.98 (m, 2H), 1.31 (t, J=7.2 Hz, 3H).

Example 1-29

Intermediate Compound 29': 4-hydroxybutyl isopropyl carbonate

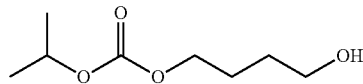

A solution of isopropyl carbonochloridate (10 ml, 1.0 M/L, 10 mmol) in DCM (10 mL) was added dropwise during 10 min to a stirred solution of butane-1,4-diol (1800 mg, 20 mmol) and Et$_3$N (2020 mg, 20 mmol) in DCM (20 mL) at 0° C. The reaction was allowed to warm up gradually and stirred at 0-25° C. over 16 h. After that, the reaction mixture was diluted with H$_2$O (5 mL) and stirred for 5 min. The aqueous phase was separated and extracted with DCM (5 mL). The combined organic phase was washed with saturated brine (5 mL), dried over anhydrous Na$_2$SO$_4$ and evaporated. The residue was purified by a silica gel flash column with Hex/EA=5:1 to yield the titled compound (1.58 g, 90%) as a colorless oil. $^1$H NMR was performed at 400 MHz with CDCl$_3$ as solvent to characterize the titled compound, results are as follows: δ=4.90-4.84 (m, 1H), 4.16 (t, J=6.6 Hz, 2H), 3.68 (t, J=6.2 Hz, 2H), 1.80-1.73 (m, 2H), 1.69-1.62 (m, 2H), 1.29 (d, J=5.6 Hz, 6H).

Compound 29: 4-(isopropoxycarbonyloxy)butanoic Acid

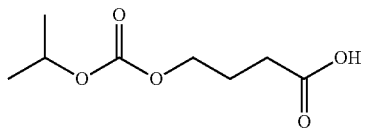

Jones reagent was added in portions to a stirred mixture of 4-hydroxybutyl isopropyl carbonate (800 mg, 4.55 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10.1-5:1 to yield the titled compound (260 mg, 30%) as a colorless oil. $^1$H NMR was performed at 400 MHz with CDCl$_3$ as solvent to characterize the titled compound, results are as follows: δ=4.90-4.84 (m, 1H), 4.18 (t, J=6.2 Hz, 2H), 2.50 (t, J=7.2 Hz, 2H), 2.05-1.97 (m, 2H), 1.30 (d, J=6.0 Hz, 6H).

Example 1-30

Intermediate Compound 30': 4-hydroxybutyl isobutyl carbonate

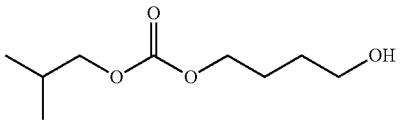

A solution of isobutyl carbonochloridate (544 mg, 4 mmol) in DCM (5 mL) was added dropwise during 10 min to a stirred solution of butane-1,4-diol (450 mg, 5 mmol) and Et$_3$N (505 mg, 5 mmol) in DCM (5 mL) at 0° C. The reaction was allowed to warm up gradually and stirred at 0-25° C. for over 1 h. After that, the reaction mixture was diluted with H$_2$O (5 mL) and stirred for 5 min. The aqueous phase was separated and extracted with DCM (5 mL). The combined organic phase was washed with saturated brine (5 mL), dried over anhydrous Na$_2$SO$_4$ and evaporated. The residue was purified by a silica gel flash column with Hex/EA=10:1-6:1 to yield the titled compound (250 mg, 33%) as a colorless oil. $^1$H NMR was performed at 400 MHz with CDCl$_3$ as solvent to characterize the titled compound, results are as follows: δ=4.18 (t, J=6.4 Hz, 2H), 3.91 (d, J=6.8 Hz, 2H), 3.69 (dd, J=5.4, 11.0 Hz, 2H), 1.81-1.75 (m, 3H), 1.70-1.62 (m, 2H), 0.96 (s, 3H), 0.94 (s, 3H).

Compound 30: 4-(isobutoxycarbonyloxy)butanoic Acid

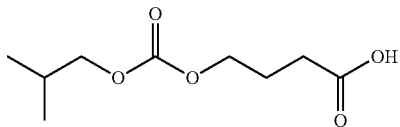

Jones reagent was added in portions to a stirred mixture of 4-hydroxybutyl isobutyl carbonate (200 mg, 1.1 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=8:1-3:1 to yield the titled compound (110 mg, 51%) as a colorless oil. $^1$H NMR was performed at 400 MHz with CDCl$_3$ as solvent to characterize the titled compound, results are as follows: δ=4.20 (t, J=6.4 Hz, 2H), 3.92 (d, J=6.8 Hz, 2H), 2.49 (t, J=7.2 Hz, 2H), 2.06-1.93 (m, 3H), 0.96 (s, 3H), 0.94 (s, 3H).

Example 1-31

Intermediate Compound 31': benzyl (4-hydroxybutyl) carbonate

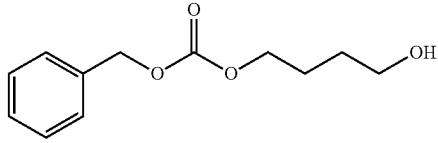

A solution of benzyl carbonochloridate (1 g, 5.86 mmol) in DCM (5 mL) was added dropwise during 10 min to a stirred solution of butane-1,4-diol (1055 mg, 11.72 mmol) and Et$_3$N (1184 mg, 11.72 mmol) in DCM (10 mL) at 0° C. The reaction was allowed to warm up gradually and stirred at 0-25° C. over 3 h. After that, the reaction mixture was diluted with H$_2$O (5 mL) and stirred for 5 min. The aqueous phase was separated and extracted with DCM (5 mL). The combined organic phase was washed with saturated brine (5 mL), dried over anhydrous Na$_2$SO$_4$ and evaporated. The residue was purified by a silica gel flash column with Hex/EA=7:1 to yield the titled compound (292 mg, 22%) as a colorless oil. $^1$H NMR was performed at 400 MHz with CDCl$_3$ as solvent to characterize the titled compound, results are as follows: δ=7.40-7.32 (m, 5H), 5.16 (s, 2H), 4.20 (t, J=6.6 Hz, 2H), 3.68 (q, J=6.0 Hz, 2H), 1.81-1.74 (m, 2H), 1.68-1.62 (m, 2H), 1.29 (t, J=5.4 Hz, 1H).

Compound 31: 4-(benzyloxycarbonyloxy)butanoic Acid

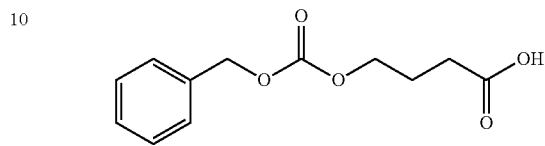

Jones reagent was added in portions to a stirred mixture of benzyl (4-hydroxybutyl) carbonate (290 mg, 1.29 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (188 mg, 61%) as a colorless oil. $^1$H NMR was performed at 400 MHz with CDCl$_3$ as solvent to characterize the titled compound, results are as follows: δ=7.38-7.33 (m, 5H), 5.16 (s, 2H), 4.21 (t, J=6.2 Hz, 2H), 2.47 (t, J=7.2 Hz, 2H), 2.03-1.97 (m, 2H).

Example 1-32

Intermediate Compound 32': 4-hydroxybutyl phenyl carbonate

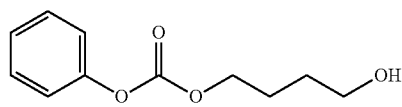 [SMILES: O=C(OCCCCO)Oc1ccccc1]

A solution of phenyl carbonochloridate (624 mg, 4 mmol) in DCM (5 mL) was added dropwise during 10 min to a stirred solution of butane-1,4-diol (450 mg, 5 mmol) and Et$_3$N (505 mg, 5 mmol) in DCM (5 mL) at 0° C. The reaction was allowed to warm up gradually and stirred at 0-25° C. for over 1 h. After that, the reaction mixture was diluted with H$_2$O (5 mL) and stirred for 5 min. The aqueous phase was separated and extracted with DCM (5 mL). The combined organic phase was washed with saturated brine (5 mL), dried over anhydrous Na$_2$SO$_4$ and evaporated. The residue was purified by a silica gel flash column with Hex/EA=10:1-5:1 to yield the titled compound (333 mg, 40%) as a colorless oil. $^1$H NMR was performed at 400 MHz with CDCl$_3$ as solvent to characterize the titled compound, results are as follows: δ=7.39 (t, J=7.8 Hz, 2H), 7.26-7.23 (m, 1H), 7.18 (d, J=8.0 Hz, 2H), 4.30 (t, J=6.6 Hz, 2H), 3.72 (dd, J=6.2, 11.2 Hz, 2H), 1.89-1.82 (m, 2H), 1.75-1.68 (m, 2H), 1.35 (t, J=5.2 Hz, 1H).

Compound 32: 4-(phenoxycarbonyloxy)butanoic Acid

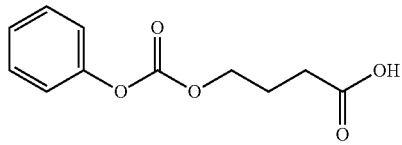 [SMILES: O=C(O)CCCOC(=O)Oc1ccccc1]

Jones reagent was added in portions to a stirred mixture of 4-hydroxybutyl phenyl carbonate (300 mg, 1.55 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-2:1 to yield the titled compound (210 mg, 65%) as a white solid. $^1$H NMR was performed at 400 MHz with $CDCl_3$ as solvent to characterize the titled compound, results are as follows: δ=7.39 (t, J=8.0 Hz, 2H), 7.25 (t, J=7.2 Hz, 1H), 7.18 (d, J=8.0 Hz, 2H), 4.32 (t, J=6.2 Hz, 2H), 2.55 (t, J=7.4 Hz, 2H), 2.13-2.06 (m, 2H).

Compound 33: 4-((4-chlorophenoxy)carbonyloxy)butanoic Acid

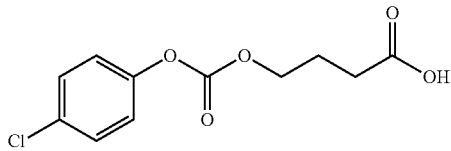

Jones reagent was added in portions to a stirred mixture of 4-chlorophenyl (4-hydroxybutyl) carbonate (400 mg, 1.64 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (220 mg, 52%) as a white solid. $^1$H NMR was performed at 400 MHz with $CDCl_3$ as solvent to characterize the titled compound, results are as follows: δ=7.35 (d, J=9.2 Hz, 2H), 7.13 (d, J=8.8 Hz, 2H), 4.32 (t, J=6.2 Hz, 2H), 2.55 (t, J=7.4 Hz, 2H), 2.13-2.06 (m, 2H).

Example 1-33

Intermediate Compound 33': 4-chlorophenyl (4-hydroxybutyl) carbonate

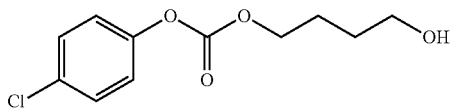 [SMILES: O=C(OCCCCO)Oc1ccc(Cl)cc1]

A solution of 4-chlorophenyl carbonochloridate (500 mg, 2.62 mmol) in DCM (5 mL) was added dropwise during 10 min to a stirred solution of butane-1,4-diol (707 mg, 7.86 mmol) and $Et_3N$ (529 mg, 5.24 mmol) in DCM (10 mL) at 0° C. The reaction was allowed to warm up gradually and stirred at 0-25° C. over 16 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=6:1 to yield the titled compound (420 mg, 66%) as a colorless oil. $^1$H NMR was performed at 400 MHz with $CDCl_3$ as solvent to characterize the titled compound, results are as follows: δ=7.35 (d, J=9.2 Hz, 2H), 7.13 (d, J=9.2 Hz, 2H), 4.30 (t, J=6.4 Hz, 2H), 3.72 (t, J=6.2 Hz, 2H), 1.89-1.82 (m, 2H), 1.74-1.67 (m, 2H).

Example 1-34

Intermediate Compound 34': 4-hydroxybutyl p-tolyl carbonate

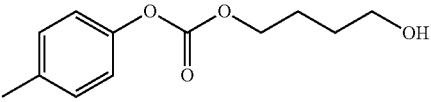 [SMILES: Cc1ccc(OC(=O)OCCCCO)cc1]

A solution of p-tolyl carbonochloridate (500 mg, 2.94 mmol) in DCM (5 mL) was added dropwise during 10 min to a stirred solution of butane-1,4-diol (794 mg, 8.82 mmol) and $Et_3N$ (594 mg, 5.88 mmol) in DCM (10 mL) at 0° C. The reaction was allowed to warm up gradually and stirred at 0-25° C. over 16 h. After that, the reaction mixture was diluted with $H_2O$ (5 mL) and stirred for 5 min. The aqueous phase was separated and extracted with DCM (5 mL). The combined organic phase was washed with saturated brine (5 mL), dried over anhydrous $Na_2SO_4$ and evaporated. The residue was purified by a silica gel flash column with Hex/EA=6:1 to yield the titled compound (600 mg, 91%) as a colorless oil. $^1$H NMR was performed at 400 MHz with $CDCl_3$ as solvent to characterize the titled compound, results are as follows: δ=7.17 (d, J=8.4 Hz, 2H), 7.05 (d, J=8.4 Hz, 2H), 4.29 (t, J=6.8 Hz, 2H), 3.72 (t, J=6.2 Hz, 2H), 2.34 (s, 3H), 1.89-1.82 (m, 2H), 1.74-1.67 (m, 2H).

Compound 34: 4-(p-tolyloxycarbonyloxy)butanoic Acid

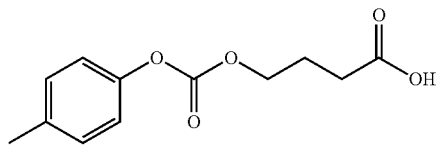 [SMILES: Cc1ccc(OC(=O)OCCCC(=O)O)cc1]

Jones reagent was added in portions to a stirred mixture of 4-hydroxybutyl p-tolyl carbonate (500 mg, 2.23 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=5:1 to yield the titled compound (170 mg, 32%) as a white solid. $^1$H NMR was performed at 400 MHz with $CDCl_3$ as solvent to characterize the titled compound, results are as follows: δ=7.17 (d, J=8.4 Hz, 2H), 7.05 (d, J=8.0 Hz, 2H), 4.31 (t, J=6.2 Hz, 2H), 2.55 (t, J=7.2 Hz, 2H), 2.34 (s, 3H), 2.12-2.07 (m, 2H).

Scheme 2

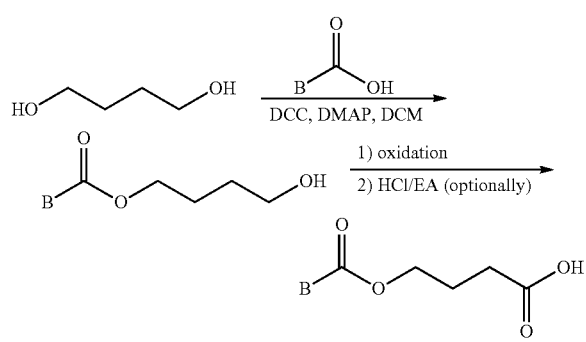

Example 1-35

Intermediate Compound 35': 4-hydroxybutyl 4-butoxybenzoate

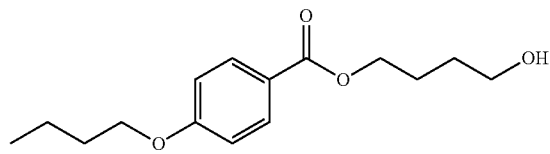 [SMILES: CCCCOc1ccc(C(=O)OCCCCO)cc1]

4-butoxybenzoic acid (882 mg, 4.55 mmol), DCC (1030 mg, 5 mmol) and DMAP (50 mg) was added to a stirred solution of butane-1,4-diol (450 mg, 5 mmol) in DCM (15 mL). The reaction was stirred at 25° C. for 3 h. After that, the reaction mixture was diluted with saturated aqueous $NH_4Cl$ (10 mL) and stirred for 5 min. The aqueous phase was separated and extracted with DCM (5 mL). The combined organic phase was washed with saturated brine (10 mL), dried over anhydrous $Na_2SO_4$ and evaporated. The residue was purified by a silica gel flash column with Hex/EA=5:1 to yield the titled compound (500 mg, 41%) as a colorless oil. $^1$H NMR was performed at 400 MHz with $CDCl_3$ as solvent to characterize the titled compound, results are as follows: δ=7.97 (d, J=8.4 Hz, 2H), 6.90 (d, J=9.2 Hz, 2H), 4.33 (t, J=6.2 Hz, 2H), 4.01 (t, J=6.6 Hz, 2H), 3.73 (t, J=6.4 Hz, 2H), 1.89-1.71 (m, 6H), 1.61 (br. s., 1H), 1.54-1.45 (m, 2H), 0.98 (t, J=7.2 Hz, 3H).

Compound 35: 4-(4-butoxybenzoyloxy)butanoic Acid

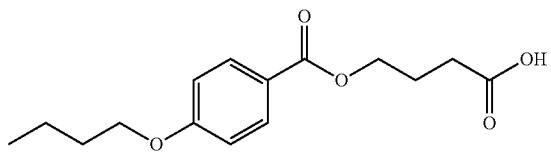 [SMILES: CCCCOc1ccc(C(=O)OCCCC(=O)O)cc1]

Jones reagent was added in portions to a stirred mixture of 4-hydroxybutyl 4-butoxybenzoate (450 mg, 1.69 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=5:1 to yield the titled compound (200 mg, 42%) as crystalline solids. $^1$H NMR was performed at 400 MHz with $CDCl_3$ as solvent to characterize the titled compound, results are as follows: δ=7.97 (d, J=8.8 Hz, 2H), 6.90 (d, J=8.8 Hz, 2H), 4.35 (t, J=6.2 Hz, 2H), 4.01 (t, J=6.4 Hz, 2H), 2.54 (t, J=7.2 Hz, 2H), 2.14-2.07 (m, 2H), 1.82-1.75 (m, 2H), 1.53-1.46 (m, 2H), 0.98 (t, J=7.4 Hz, 3H).

Example 1-36

Intermediate Compound 36': 4-hydroxybutyl 4-isopropylbenzoate

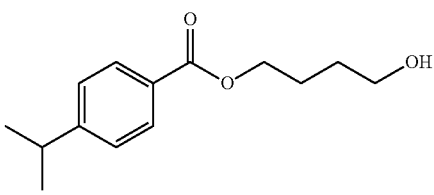 [SMILES: CC(C)c1ccc(C(=O)OCCCCO)cc1]

4-isopropylbenzoic acid (745 mg, 4.54 mmol), DCC (1030 mg, 5 mmol) and DMAP (50 mg) was added to a stirred solution of butane-1,4-diol (450 mg, 5 mmol) in DCM (15 mL). The reaction was stirred at 25° C. for 3 h. After that, the reaction mixture was diluted with saturated aqueous $NH_4Cl$ (10 mL) and stirred for 5 min. The aqueous phase was separated and extracted with DCM (5 mL). The combined organic phase was washed with saturated brine (10 mL), dried over anhydrous $Na_2SO_4$ and evaporated. The residue was purified by a silica gel flash column with Hex/EA=5:1 to yield the titled compound (400 mg, 37%) as a colorless oil. ¹H NMR was performed at 400 MHz with CDCl₃ as solvent to characterize the titled compound, results are as follows: δ=7.96 (d, J=8.0 Hz, 2H), 7.29 (d, J=8.0 Hz, 2H), 4.35 (t, J=6.4 Hz, 2H), 3.76-3.69 (m, 2H), 2.99-2.93 (m, 1H), 1.90-1.83 (m, 2H), 1.76-1.69 (m, 2H), 1.40 (br. s., 1H), 1.27 (s, 3H), 1.26 (s, 3H).

Compound 36: 4-(4-isopropylbenzoyloxy) butanoic Acid

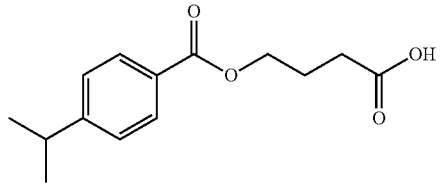 [SMILES: CC(C)c1ccc(C(=O)OCCCC(=O)O)cc1]

Jones reagent was added in portions to a stirred mixture of 4-hydroxybutyl 4-isopropylbenzoate (350 mg, 1.48 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na₂SO₄ and concentrated. The residue was purified by a silica gel flash column with Hex/EA=5:1 to yield the titled compound (200 mg, 54%) as a colorless oil. ¹H NMR was performed at 400 MHz with CDCl₃ as solvent to characterize the titled compound, results are as follows: δ=7.95 (d, J=8.0 Hz, 2H), 7.29 (d, J=8.4 Hz, 2H), 4.37 (t, J=6.2 Hz, 2H), 2.99-2.92 (m, 1H), 2.54 (t, J=7.4 Hz, 2H), 2.15-2.08 (m, 2H), 1.27 (s, 3H), 1.25 (s, 3H).

Example 1-37

Intermediate Compound 37': 4-hydroxybutyl 3-(methylsulfonyl)benzoate

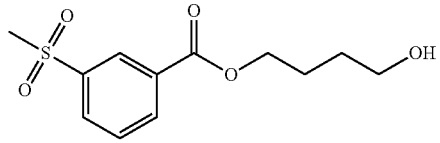 [SMILES: CS(=O)(=O)c1cccc(C(=O)OCCCCO)c1]

3-(methylsulfonyl) benzoic acid (505 mg, 2.53 mmol), DCC (572 mg, 2.78 mmol) and DMAP (50 mg) was added to a stirred solution of butane-1,4-diol (250 mg, 2.78 mmol) in DCM (15 mL). The reaction was stirred at 25° C. for 3 h. After that, the reaction mixture was diluted with saturated aqueous NH₄Cl (10 mL) and stirred for 5 min. The aqueous phase was separated and extracted with DCM (5 mL). The combined organic phase was washed with saturated brine (10 mL), dried over anhydrous Na₂SO₄ and evaporated. The residue was purified by a silica gel flash column with Hex/EA=2:1 to yield the titled compound (150 mg, 22%) as a colorless oil. ¹H NMR was performed at 400 MHz with CDCl₃ as solvent to characterize the titled compound, results are as follows: δ-8.60 (s, 1H), 8.33 (d, J=8.0 Hz, 1H), 8.15 (d, J=8.0 Hz, 1H), 7.69 (t, J=7.8 Hz, 1H), 4.42 (t, J=6.6 Hz, 2H), 3.74 (q, J=6.0 Hz, 2H), 3.10 (s, 3H), 1.94-1.87 (m, 2H), 1.76-1.70 (m, 2H), 1.36 (t, J=5.0 Hz, 1H).

Compound 37: 4-(3-(methylsulfonyl)benzoyloxy)butanoic Acid

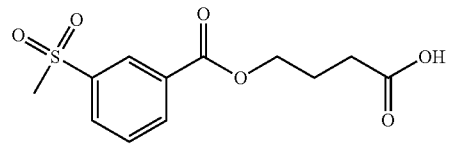 [SMILES: CS(=O)(=O)c1cccc(C(=O)OCCCC(=O)O)c1]

Jones reagent was added in portions to a stirred mixture of 4-hydroxybutyl 3-(methylsulfonyl)benzoate (150 mg, 0.55 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na₂SO₄ and concentrated. The residue was purified by a silica gel flash column with Hex/EA=2:1 to yield the titled compound (70 mg, 44%) as crystalline solids. ¹H NMR was performed at 400 MHz with CDCl₃ as solvent to characterize the titled compound, results are as follows: δ=8.59 (s, 1H), 8.32 (d, J=8.0 Hz, 1H), 8.15 (d, J=8.0 Hz, 1H), 7.69 (t, J=7.8 Hz, 1H), 4.44 (t, J=6.2 Hz, 2H), 3.11 (s, 3H), 2.55 (t, J=7.0 Hz, 2H), 2.20-2.14 (m, 2H).

Example 1-38

Intermediate Compound 38': 4-hydroxybutyl nicotinate

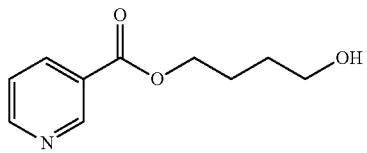 [SMILES: O=C(OCCCCO)c1cccnc1]

Nicotinic acid (615 mg, 5 mmol), DCC (1133 mg, 5.5 mmol) and DMAP (50 mg) was added to a stirred solution of butane-1,4-diol (900 mg, 10 mmol) in DCM (15 mL). The reaction was stirred at 25° C. for 16 h. After that, the reaction mixture was diluted with saturated aqueous NH₄Cl (10 mL) and stirred for 5 min. The aqueous phase was separated and extracted with DCM (5 mL). The combined organic phase was washed with saturated brine (10 mL), dried over anhydrous Na₂SO₄ and evaporated. The residue was purified by a silica gel flash column with Hex/EA=1:1 to yield the titled compound (450 mg, 46%) as a colorless oil. ¹H NMR was performed at 400 MHz with CDCl₃ as solvent to characterize the titled compound, results are as follows: δ=9.22 (d, J=1.6 Hz, 1H), 8.78 (dd, J=1.6, 4.8 Hz, 1H), 8.30 (td, J=1.6, 8.0 Hz, 1H), 7.40 (dd, J=5.0, 7.8 Hz, 1H), 4.41 (t, J=6.6 Hz, 2H), 3.74 (t, J=6.2 Hz, 2H), 1.93-1.86 (m, 2H), 1.77-1.70 (m, 2H), 1.46 (br. s., 1H).

Compound 38: 4-(nicotinoyloxy)butanoic Aid

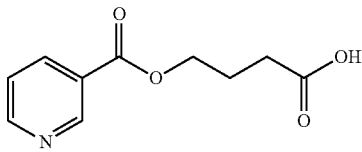 [SMILES: O=C(O)CCCOC(=O)c1cccnc1]

Jones reagent was added in portions to a stirred mixture of 4-hydroxybutyl nicotinate (450 mg, 2.31 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=1:1 to yield the titled compound (50 mg, 10%) as crystalline solids. $^1$H NMR was performed at 400 MHz with $CDCl_3$ as solvent to characterize the titled compound, results are as follows: δ=9.21 (d, J=1.6 Hz, 1H), 8.72 (dd, J=1.2, 4.8 Hz, 1H), 8.33 (td, J=1.6, 7.6 Hz, 1H), 7.40 (dd, J=5.0, 7.8 Hz, 1H), 4.45 (t, J=6.2 Hz, 2H), 2.56 (t, J=7.0 Hz, 2H), 2.21-2.15 (m, 2H).

Example 1-39

Intermediate Compound 39': 4-hydroxybutyl isonicotinate

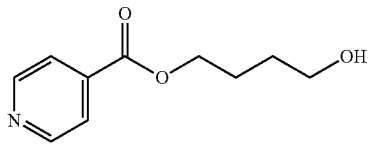 [SMILES: O=C(OCCCCO)c1ccncc1]

Isonicotinic acid (1.23 g, 10 mmol), DCC (2.27 g, 11 mmol) and DMAP (122 mg) was added to a stirred solution of butane-1,4-diol (2.7 g, 30 mmol) in DCM (30 mL). The reaction was stirred at 25° C. for 8 h. After that, the reaction mixture was diluted with saturated aqueous $NH_4Cl$ (10 mL) and stirred for 5 min. The aqueous phase was separated and extracted with DCM (15 mL). The combined organic phase was washed with brine (10 mL), dried over $Na_2SO_4$ and evaporated. The residue was purified by a silica gel flash column with Hex/EA=10:1-2:1 to yield the titled compound (1 g, 51%) as a pale yellow oil. $^1$H NMR was performed at 400 MHz with $CDCl_3$ as solvent to characterize the titled compound, results are as follows: δ=8.76 (d, J=8.4 Hz, 2H), 7.84 (d, J=5.6 Hz, 2H), 4.39 (t, J=6.4 Hz, 2H), 3.72 (t, J=6.2 Hz, 2H), 1.92-1.85 (m, 2H), 1.75-1.70 (m, 2H).

Compound 39: 4-(isonicotinoyloxy)butanoic Acid

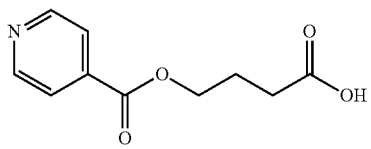 [SMILES: O=C(O)CCCOC(=O)c1ccncc1]

Jones reagent was added in portions to a stirred mixture of 4-hydroxybutyl isonicotinate (900 mg, 4.62 mmol) and Celite® (diatomaceous earth, 2 g) in acetone (30 mL) at 0° C. The reaction proceeded at 0° C. over 1 h and the reaction progress was monitored by TLC. After completion, the reaction was quenched with drops of iPrOH, diluted with EA (50 mL) and then filtered. The filtered cake was washed with EA (50 mL) and the combined filtrate was washed with brine (5 mL×2), dried over $Na_2SO_4$ and concentrated. The residue was purified by a silica gel flash column with Hex/EA=2:1 to yield the titled compound (70 mg, 7%) as a white solid. $^1$H NMR was performed at 400 MHz with $CDCl_3$ as solvent to characterize the titled compound, results are as follows: δ=8.55 (d, J=6.0 Hz, 2H), 7.86 (d, J=6.4 Hz, 2H), 4.49 (t, J=5.8 Hz, 2H), 2.53 (t, J=6.6 Hz, 2H), 2.23-2.17 (m, 2H).

Example 1-40

Intermediate Compound 40': 4-hydroxybutyl 3-methoxy-4-methylbenzoate

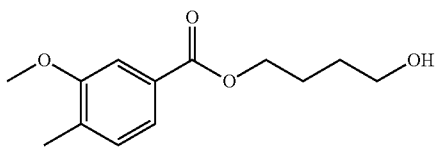 [SMILES: COc1cc(C(=O)OCCCCO)ccc1C]

3-methoxy-4-methylbenzoic acid (500 mg, 3 mmol), DCC (683 mg, 3.32 mmol) and DMAP (50 mg) was added to a stirred solution of butane-1,4-diol (542 mg, 6 mmol) in DCM (15 mL). The reaction was stirred at 25° C. for 3 h. After that, the reaction mixture was diluted with saturated aqueous $NH_4Cl$ (10 mL) and stirred for 5 min. The aqueous phase was separated and extracted with DCM (5 mL). The combined organic phase was washed with saturated brine (10 mL), dried over anhydrous $Na_2SO_4$ and evaporated. The residue was purified by a silica gel flash column with Hex/EA=5:1 to yield the titled compound (450 mg, 63%) as a colorless oil. $^1$H NMR was performed at 400 MHz with $CDCl_3$ as solvent to characterize the titled compound, results are as follows: δ=7.55 (d, J=7.6 Hz, 1H), 7.48 (s, 1H), 7.18 (d, J=8.0 Hz, 1H), 4.36 (t, J=6.4 Hz, 2H), 3.88 (s, 3H), 3.73 (t, J=6.2 Hz, 2H), 2.26 (s, 3H), 1.91-1.84 (m, 2H), 1.76-1.70 (m, 2H).

Compound 40: 4-(3-methoxy-4-methylbenzoyloxy)butanoic Acid

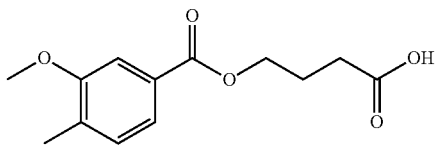 [SMILES: COc1cc(C(=O)OCCCC(=O)O)ccc1C]

Jones reagent was added in portions to a stirred mixture of 4-hydroxybutyl 3-methoxy-4-methylbenzoate (450 mg, 1.89 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=4:1 to yield the titled compound (280 mg, 59%) as crystalline solids. $^1$H NMR was performed at 400 MHz with CDCl$_3$ as solvent to characterize the titled compound, results are as follows: δ=7.54 (d, J=7.6 Hz, 1H), 7.47 (s, 1H), 7.18 (d, J=7.6 Hz, 1H), 4.37 (t, J=6.2 Hz, 2H), 3.88 (s, 3H), 2.54 (t, J=7.4 Hz, 2H), 2.26 (s, 3H), 2.15-2.09 (m, 2H).

Example 1-41

Intermediate Compound 41': 4-hydroxybutyl 2,6-dimethylbenzoate

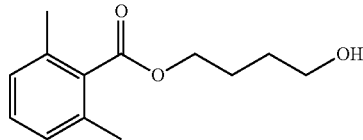 [SMILES: Cc1cccc(C)c1C(=O)OCCCCO]

2,6-dimethylbenzoic acid (500 mg, 3.33 mmol), DCC (755 mg, 3.67 mmol) and DMAP (50 mg) was added to a stirred solution of butane-1,4-diol (600 mg, 6.67 mmol) in DCM (15 mL). The reaction was stirred at 25° C. for 3 h. After that, the reaction mixture was diluted with saturated aqueous NH$_4$Cl (10 mL) and stirred for 5 min. The aqueous phase was separated and extracted with DCM (5 mL). The combined organic phase was washed with saturated brine (10 mL), dried over anhydrous Na$_2$SO$_4$ and evaporated. The residue was purified by a silica gel flash column with Hex/EA=5:1 to yield the titled compound (100 mg, 14%) as a colorless oil. $^1$H NMR was performed at 400 MHz with CDCl$_3$ as solvent to characterize the titled compound, results are as follows: δ=7.18 (t, J=7.6 Hz, 1H), 7.03 (d, J=8.0 Hz, 2H), 4.37 (t, J=6.6 Hz, 2H), 3.71 (t, J=6.4 Hz, 2H), 2.32 (s, 6H), 1.89-1.82 (m, 2H), 1.74-1.67 (m, 2H).

Compound 41: 4-(2,6-dimethylbenzoyloxy)butanoic Acid

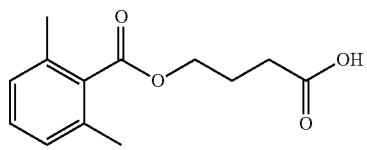 [SMILES: Cc1cccc(C)c1C(=O)OCCCC(=O)O]

Jones reagent was added in portions to a stirred mixture of 4-hydroxybutyl 2,6-dimethylbenzoate (100 mg, 0.45 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (50 mg, 47%) as a colorless oil. $^1$H NMR was performed at 400 MHz with CDCl$_1$ as solvent to characterize the titled compound, results are as follows: δ=7.19 (t, J=7.4 Hz, 1H), 7.03 (d, J=7.6 Hz, 2H), 4.39 (t, J=6.4 Hz, 2H), 2.52 (t, J=7.4 Hz, 2H), 2.32 (s, 6H), 2.13-2.07 (m, 2H).

Example 1-42

Intermediate Compound 42': 4-hydroxybutyl 2-phenoxybenzoate

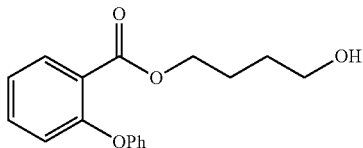 [SMILES: O=C(OCCCCO)c1ccccc1Oc1ccccc1]

2-phenoxybenzoic acid (1070 mg, 5 mmol), DCC (1133 mg, 5.5 mmol) and DMAP (50 mg) was added to a stirred solution of butane-1,4-diol (900 mg, 10 mmol) in DCM (30 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=8:1 to yield the titled compound (700 mg, 49%) as a colorless oil. $^1$H NMR was performed at 400 MHz with CDCl$_3$ as solvent to characterize the titled compound, results are as follows: δ=7.93 (dd, J=1.6, 8.0 Hz, 1H), 7.50-7.45 (m, 1H), 7.32 (t, J=7.8 Hz, 2H), 7.21 (t, J=7.6 Hz, 1H), 7.07 (t, J=7.4 Hz, 1H), 7.00 (d, J=8.0 Hz, 1H), 6.94 (d, J=7.6 Hz, 2H), 4.26 (t, J=6.2 Hz, 2H), 3.58 (s, 2H), 1.72-1.65 (m, 2H), 1.58-1.51 (m, 2H).

Compound 42: 4-(2-phenoxybenzoyloxy)butanoic Acid

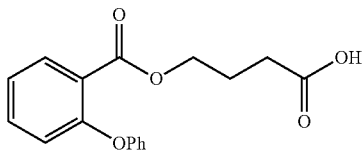 [SMILES: O=C(O)CCCOC(=O)c1ccccc1Oc1ccccc1]

Jones reagent was added in portions to a stirred mixture of 4-hydroxybutyl 2-phenoxybenzoate (700 mg, 2.45 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (400 mg, 54%) as a white solid. $^1$H NMR was performed at 400 MHz with CDCl$_3$ as solvent to characterize the titled compound, results are as follows: δ=7.92 (dd, J=1.6, 7.6 Hz, 1H), 7.50-7.46 (m, 1H), 7.31 (d, J=8.0 Hz, 2H), 7.20 (t, J=7.6 Hz, 1H), 7.07 (t, J=7.4 Hz, 1H), 7.00 (d, J=8.4 Hz, 1H), 6.93 (d, J=8.0 Hz, 2H), 4.27 (t, J=6.2 Hz, 2H), 2.36 (t, J=7.2 Hz, 2H), 1.96-1.90 (m, 2H).

Example 1-43

Intermediate Compound 43': 4-hydroxybutyl 2,4-dimethylbenzoate

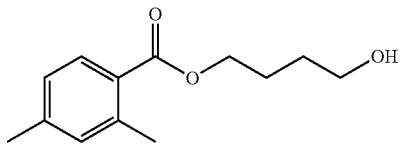 [SMILES: Cc1ccc(C(=O)OCCCCO)c(C)c1]

2,4-dimethylbenzoic acid (750 mg, 5 mmol), DCC (1133 mg, 5.5 mmol) and DMAP (50 mg) was added to a stirred solution of butane-1,4-diol (900 mg, 10 mmol) in DCM (30 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=8:1 to yield the titled compound (700 mg, 63%) as a colorless oil. $^1$H NMR was performed at 400 MHz with CDCl$_3$ as solvent to characterize the titled compound, results are as follows: δ=7.82 (d, J=7.6 Hz, 1H), 7.05-7.03 (m, 2H), 4.32 (t, J=6.6 Hz, 2H), 3.73 (s, 2H), 2.57 (s, 3H), 2.35 (s, 3H), 1.89-1.82 (m, 2H), 1.76-1.69 (m, 2H).

Compound 43: 4-(2,4-dimethylbenzoyloxy)butanoic Acid

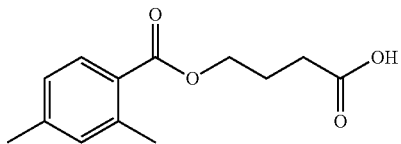 [SMILES: Cc1ccc(C(=O)OCCCC(=O)O)c(C)c1]

Jones reagent was added in portions to a stirred mixture of 4-hydroxybutyl 2,4-dimethylbenzoate (700 mg, 3.15 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (550 mg, 74%) as a white solid. $^1$H NMR was performed at 400 MHz with CDCl$_3$ as solvent to characterize the titled compound, results are as follows: δ=7.82 (d, J=7.6 Hz, 1H), 7.05-7.03 (m, 2H), 4.34 (t, J=6.2 Hz, 2H), 2.57 (s, 3H), 2.54 (t, J=7.4 Hz, 2H), 2.35 (s, 3H), 2.14-2.08 (m, 2H).

Example 1-44

Intermediate Compound 44': 4-hydroxybutyl 2,3-dimethoxybenzoate

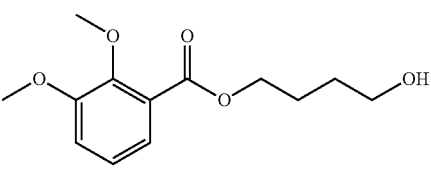 [SMILES: COc1cccc(C(=O)OCCCCO)c1OC]

2,3-dimethoxybenzoic acid (910 mg, 5 mmol), DCC (1133 mg, 5.5 mmol) and DMAP (50 mg) was added to a stirred solution of butane-1,4-diol (900 mg, 10 mmol) in DCM (30 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=8:1 to yield the titled compound (600 mg, 47%) as a colorless oil. $^1$H NMR was performed at 400 MHz with CDCl$_3$ as solvent to characterize the titled compound, results are as follows: δ=7.32 (dd, J=1.6, 7.2 Hz, 1H), 7.11-7.04 (m, 2H), 4.36 (t, J=6.4 Hz, 2H), 3.90 (s, 3H), 3.89 (s, 3H), 3.74-3.70 (m, 2H), 1.90-1.84 (m, 2H), 1.77-1.70 (m, 2H), 1.40 (t, J=4.8 Hz, 1H).

Compound 44: 4-(2,3-dimethoxybenzoyloxy)butanoic Acid

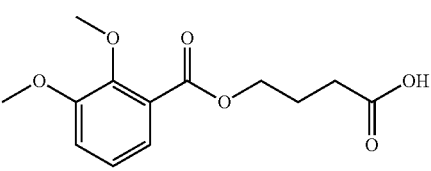 [SMILES: COc1cccc(C(=O)OCCCC(=O)O)c1OC]

Jones reagent was added in portions to a stirred mixture of 4-hydroxybutyl 2,3-dimethoxybenzoate (600 mg, 2.36 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (250 mg, 39%) as a white solid. $^1$H NMR was performed at 400 MHz with CDCl$_3$ as solvent to characterize the titled compound, results are as follows: δ=7.31 (dd, J=2.0, 7.2 Hz, 1H), 7.11-7.05 (m, 2H), 4.38 (t, J=6.2 Hz, 2H), 3.91 (s, 3H), 3.89 (s, 3H), 2.57 (t, J=7.4 Hz, 2H), 2.15-2.08 (m, 2H).

Example 1-45

Intermediate Compound 45': 4-hydroxybutyl 4-isopropoxybenzoate

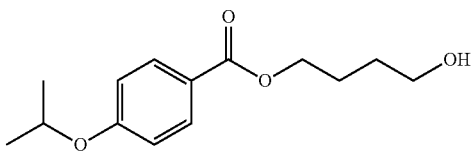 [SMILES: CC(C)Oc1ccc(C(=O)OCCCCO)cc1]

4-isopropoxybenzoic acid (900 mg, 5 mmol), DCC (1133 mg, 5.5 mmol) and DMAP (50 mg) was added to a stirred solution of butane-1,4-diol (900 mg, 10 mmol) in DCM (30 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=6:1 to yield the titled compound (800 mg, 63%) as a colorless oil. $^1$H NMR was performed at 400 MHz with CDCl$_3$ as solvent to characterize the titled compound, results are as follows: δ=7.97 (d, J=8.8 Hz, 2H), 6.88 (d, J=9.2 Hz, 2H), 4.66-4.60 (m, 1H), 4.33 (t, J=6.4 Hz, 2H), 3.73 (q, J=6.0 Hz, 2H), 1.89-1.82 (m, 2H), 1.76-1.69 (m, 2H), 1.37 (s, 3H), 1.35 (s, 3H).

Compound 45: 4-(4-isopropoxybenzoyloxy)butanoic Acid

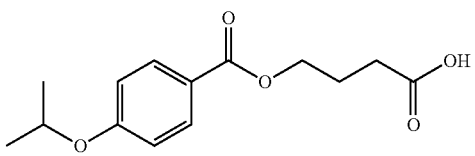 [SMILES: CC(C)Oc1ccc(C(=O)OCCCC(=O)O)cc1]

Jones reagent was added in portions to a stirred mixture of 4-hydroxybutyl 4-isopropoxybenzoate (800 mg, 3.17 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (380 mg, 45%) as a colorless oil. $^1$H NMR was performed at 400 MHz with CDCl$_3$ as solvent to characterize the titled compound, results are as follows: δ=7.96 (d, J=8.8 Hz, 2H), 6.88 (d, J=8.8 Hz, 2H), 4.66-4.60 (m, 1H), 4.35 (t, J=6.2 Hz, 2H), 2.54 (t, J=7.2 Hz, 2H), 2.15-2.08 (m, 2H), 1.37 (s, 3H), 1.35 (s, 3H).

Example 1-46

Intermediate Compound 46': 4-hydroxybutyl 2-ethylbenzoate

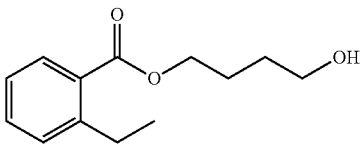 [SMILES: CCc1ccccc1C(=O)OCCCCO]

2,6-dimethylbenzoic acid (500 mg, 3.33 mmol), DCC (755 mg, 3.67 mmol) and DMAP (50 mg) was added to a stirred solution of butane-1,4-diol (600 mg, 6.67 mmol) in DCM (30 mL). The reaction was stirred at 25° C. for 3 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=8:1 to yield the titled compound (480 mg, 65%) as a colorless oil. $^1$H NMR was performed at 400 MHz with CDCl$_3$ as solvent to characterize the titled compound, results are as follows: δ=7.84 (d, J=8.0 Hz, 1H), 7.43 (t, J=7.4 Hz, 1H), 7.28-7.22 (m, 2H), 4.34 (t, J=6.6 Hz, 2H), 3.73 (t, J=6.0 Hz, 2H), 2.98 (q, J=7.6 Hz, 2H), 1.91-1.84 (m, 2H), 1.77-1.70 (m, 2H), 1.24 (t, J=7.4 Hz, 3H).

Compound 46: 4-(2-ethylbenzoyloxy)butanoic Acid

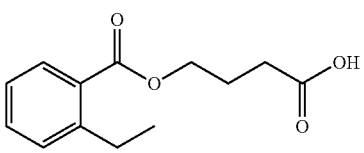 [SMILES: CCc1ccccc1C(=O)OCCCC(=O)O]

Jones reagent was added in portions to a stirred mixture of 4-hydroxybutyl 2-ethylbenzoate (480 mg, 2.16 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=6:1 to yield the titled compound (290 mg, 57%) as a white solid. $^1$H NMR was performed at 400 MHz with CDCl$_3$ as solvent to characterize the titled compound, results are as follows: δ=7.84 (d, J=8.0 Hz, 1H), 7.43 (d, J=7.2 Hz, 1H), 7.29-7.22 (m, 2H), 4.36 (t, J=6.2 Hz, 2H), 2.98 (q, J=7.6 Hz, 2H), 2.55 (t, J=7.2 Hz, 2H), 2.15-2.08 (m, 2H), 1.24 (t, J=7.6 Hz, 3H).

Example 1-47

Intermediate Compound 47': 4-hydroxybutyl 4-benzoylbenzoate

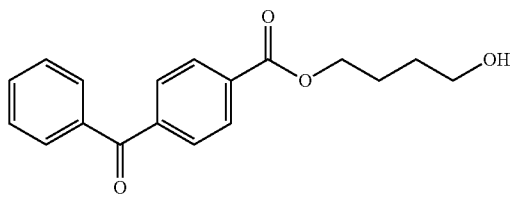 [SMILES: O=C(OCCCCO)c1ccc(C(=O)c2ccccc2)cc1]

4-benzoylbenzoic acid (500 mg, 2.21 mmol), DCC (501 mg, 2.44 mmol) and DMAP (5 mg) was added to a stirred solution of butane-1,4-diol (398 mg, 4.42 mmol) in DCM (30 mL). The reaction was stirred at 25° C. for 3 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=6:1 to yield the titled compound (400 mg, 61%) as a white solid. $^1$H NMR was performed at 400 MHz with CDCl$_3$ as solvent to characterize the titled compound, results are as follows: δ=8.15 (d, J=8.4 Hz, 2H), 7.85-7.80 (m, 4H), 7.62 (t, J=7.6 Hz, 1H), 7.50 (t, J=7.6 Hz, 2H), 4.41 (t, J=6.4 Hz, 2H), 3.75 (t, J=6.4 Hz, 2H), 1.94-1.87 (m, 2H), 1.79-1.72 (m, 2H).

Compound 47: 4-(4-benzoylbenzoyloxy)butanoic Acid

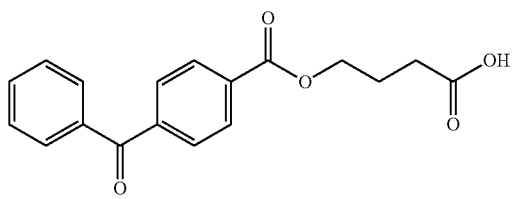 [SMILES: O=C(O)CCCOC(=O)c1ccc(C(=O)c2ccccc2)cc1]

Jones reagent was added in portions to a stirred mixture of 4-hydroxybutyl 4-benzoylbenzoate (400 mg, 1.34 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1 to yield the titled compound (280 mg, 67%) as a white solid. $^1$H NMR was performed at 400 MHz with CDCl$_3$ as solvent to characterize the titled compound, results are as follows: δ=8.14 (d, J=8.4 Hz, 2H), 7.85-7.80 (m, 4H), 7.62 (t, J=7.6 Hz, 1H), 7.50 (t, J=7.6 Hz, 2H), 4.44 (t, J=6.2 Hz, 2H), 2.57 (t, J=7.2 Hz, 2H), 2.19-2.12 (m, 2H).

Example 1-48

Intermediate Compound 48': 4-hydroxybutyl methyl phthalate

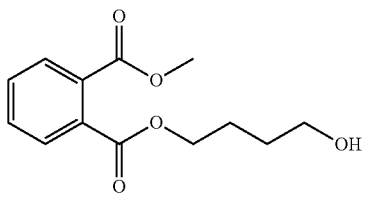 [SMILES: COC(=O)c1ccccc1C(=O)OCCCCO]

2-(methoxycarbonyl)benzoic acid (900 mg, 5 mmol), DCC (1.13 g, 5.5 mmol) and DMAP (60 mg) was added to a stirred solution of butane-1,4-diol (1.35 g, 15 mmol) in DCM (30 mL). The reaction was stirred at 25° C. for 3 h. After that, the reaction mixture was diluted with saturated aqueous NH$_4$Cl (10 mL) and stirred for 5 min. The aqueous phase was separated and extracted with DCM (15 mL). The combined organic phase was washed with brine (10 mL), dried over Na$_2$SO$_4$ and evaporated. The residue was purified by a silica gel flash column with Hex/EA=10:1-2:1 to yield the titled compound (1 g, 79%) as a colorless oil. $^1$H NMR was performed at 400 MHz with CDCl$_3$ as solvent to characterize the titled compound, results are as follows: δ=7.72-7.68 (m, 2H), 7.55-7.51 (m, 2H), 4.34 (t, J=6.6 Hz, 2H), 3.89 (s, 3H), 3.68 (t, J=6.4 Hz, 2H), 1.83-1.77 (m, 3H), 1.70-1.65 (m, 2H).

Compound 48: 4-(2-(methoxycarbonyl)benzoyloxy)butanoic Acid

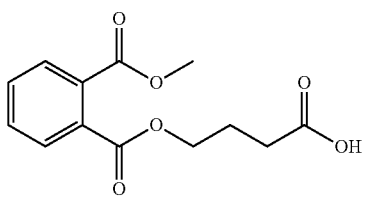 [SMILES: COC(=O)c1ccccc1C(=O)OCCCC(=O)O]

Jones reagent was added in portions to a stirred mixture of 4-hydroxybutyl methyl phthalate (900 mg, 3.57 mmol) and Celite® (diatomaceous earth, 2 g) in acetone (20 mL) at 0° C. The reaction proceeded at 0° C. over 1 h and the reaction progress was monitored by TLC. After completion, the reaction was quenched with drops of iPrOH, diluted with EA (10 mL) and then filtered. The filtered cake was washed with EA (10 mL) and the combined filtrate was washed with brine (3 mL×2), dried over Na$_2$SO$_4$ and concentrated. The residue was purified by a silica gel flash column with Hex/EA=10:1-1:1 to yield the titled compound (800 mg, 84%) as a colorless oil. $^1$H NMR was performed at 400 MHz with CDCl$_3$ as solvent to characterize the titled compound, results are as follows: δ=7.74-7.70 (m, 2H), 7.55-7.53 (m, 2H), 4.37 (t, J=6.2 Hz, 2H), 3.91 (s, 3H), 2.51 (t, J=7.2 Hz, 2H), 2.10-2.03 (m, 2H).

Example 1-49

Intermediate Compound 49': 4-hydroxybutyl methyl terephthalate

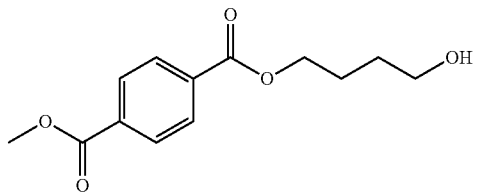 [SMILES: COC(=O)c1ccc(C(=O)OCCCCO)cc1]

4-(methoxycarbonyl)benzoic acid (1 g, 5.56 mmol), DCC (1258 mg, 6.11 mmol) and DMAP (10 mg) was added to a stirred solution of butane-1,4-diol (1.5 g, 16.67 mmol) in DCM (20 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (5 mL). The combined organic phase was washed with brine (10 mL), dried over Na$_2$SO$_4$ and evaporated. The residue was purified by a silica gel flash column with Hex/EA=7:1 to yield the titled compound (750 mg, 54%) as crystalline solids. $^1$H NMR was performed at 400 MHz with CDCl$_3$ as solvent to characterize the titled compound, results are as follows: δ=8.10 (s, 4H), 4.39 (t, J=6.6 Hz, 2H), 3.95 (s, 3H), 3.74 (t, J=6.4 Hz, 2H), 1.92-1.87 (m, 2H), 1.77-1.72 (m, 2H).

Compound 49:
4-(4-(methoxycarbonyl)benzoyloxy)butanoic Acid

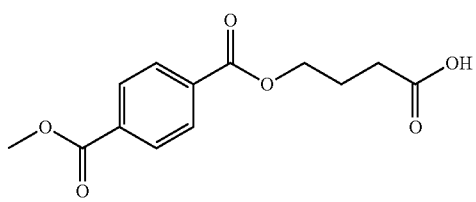 [SMILES: COC(=O)c1ccc(C(=O)OCCCC(=O)O)cc1]

Jones reagent was added in portions to a stirred mixture of 4-hydroxybutyl methyl terephthalate (700 mg, 2.78 mmol) and Celite® (diatomaceous earth, 2 g) in acetone (10 mL) at 0° C. The reaction proceeded at 0° C. over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with brine (2 mL×2), dried over Na$_2$SO$_4$ and concentrated. The residue was purified by a silica gel flash column with Hex/EA=7:1 to yield the titled compound (400 mg, 54%) as crystalline solids. $^1$H NMR was performed at 400 MHz with CDCl$_3$ as solvent to characterize the titled compound, results are as follows: δ=8.09 (s, 4H), 4.41 (t, J=6.2 Hz, 2H), 3.95 (s, 3H), 2.55 (t, J=7.2 Hz, 2H), 2.18-2.11 (m, 2H).

Example 1-50

Intermediate Compound 50': 4-hydroxybutyl ($^2$H$_5$)benzoate

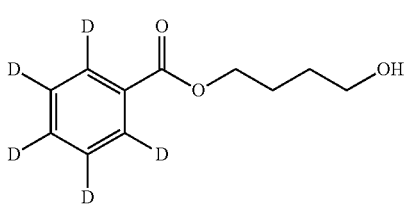 [SMILES: [2H]c1c([2H])c([2H])c(C(=O)OCCCCO)c([2H])c1[2H]]

($^2$H$_5$) benzoic acid (300 mg, 2.36 mmol), DCC (535 mg, 2.6 mmol) and DMAP (10 mg) was added to a stirred solution of butane-1,4-diol (425 mg, 4.72 mmol) in DCM (20 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=5:1 to yield the titled compound (320 mg, 68%) as a colorless oil. $^1$H NMR was performed at 400 MHz with CDCl$_3$ as solvent to characterize the titled compound, results are as follows: δ=4.37 (t, J=6.4 Hz, 2H), 3.74 (t, J=6.4 Hz, 2H), 1.91-1.84 (m, 2H), 1.78-1.71 (m, 2H).

Compound 50: 4-(($^2$H$_5$)phenylcarbonyloxy)butanoic Acid

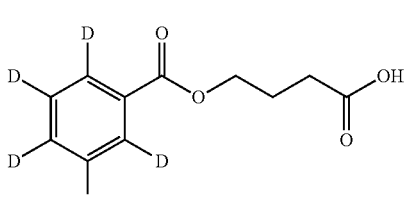

Jones reagent was added in portions to a stirred mixture of 4-hydroxybutyl ($^2$H$_5$)benzoate (300 mg, 1.51 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (220 mg, 69%) as a white solid. $^1$H NMR was performed at 400 MHz with CDCl$_3$ as solvent to characterize the titled compound, results are as follows: δ=4.39 (t, J=6.2 Hz, 2H), 2.56 (t, J=7.4 Hz, 2H), 2.17-2.10 (m, 2H).

Example 1-51

Intermediate Compound 51': 4-hydroxybutyl thiazole-2-carboxylate

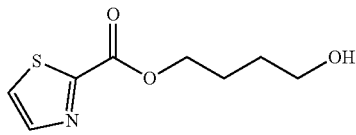 [SMILES: O=C(OCCCCO)c1nccs1]

Thiazole-2-carboxylic acid (500 mg, 3.88 mmol), DCC (879 mg, 4.27 mmol) and DMAP (50 mg) was added to a stirred solution of butane-1,4-diol (1.05 g, 11.66 mmol) in DCM (10 mL). The reaction was stirred at 25° C. for 8 h. After that, the reaction mixture was diluted with saturated aqueous NH$_4$Cl (10 mL) and stirred for 5 min. The aqueous phase was separated and extracted with DCM (5 mL). The combined organic phase was washed with brine (10 mL), dried over Na$_2$SO$_4$ and evaporated. The residue was purified by a silica gel flash column with Hex/EA=10:1-2:1 to yield the titled compound (300 mg, 38%) as a pale yellow oil. $^1$H NMR was performed at 400 MHz with CDCl$_3$ as solvent to characterize the titled compound, results are as follows: δ=8.03 (d, J=2.8 Hz, 1H), 7.64 (d, J=3.2 Hz, 1H), 4.47 (t, J=6.6 Hz, 2H), 3.73 (t, J=6.2 Hz, 2H), 1.97-1.90 (m, 2H), 1.77-1.70 (m, 2H).

Compound 51: 4-(thiazole-2-carbonyloxy)butanoic Acid

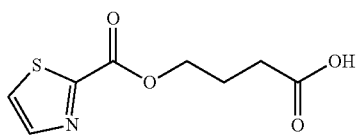 [SMILES: O=C(O)CCCOC(=O)c1nccs1]

Jones reagent was added in portions to a stirred mixture of 4-hydroxybutyl thiazole-2-carboxylate (300 mg, 1.49 mmol) and Celite® (diatomaceous earth, 2 g) in acetone (10 mL) at 0° C. The reaction proceeded at 0° C. over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with brine (2 mL×2), dried over Na$_2$SO$_4$ and concentrated. The residue was purified by a silica gel flash column with Hex/EA=10:1-1:1 to yield the titled compound (200 mg, 62%) as crystalline solids. $^1$H NMR was performed at 400 MHz with CDCl$_3$ as solvent to characterize the titled compound, results are as follows: δ=8.06 (d, J=2.8 Hz, 1H), 7.67 (d, J=3.2 Hz, 1H), 4.49 (t, J=6.2 Hz, 2H), 2.58 (t, J=7.2 Hz, 2H), 2.19-2.12 (m, 2H).

Example 1-52

Intermediate Compound 52': 4-hydroxybutyl furan-3-carboxylate

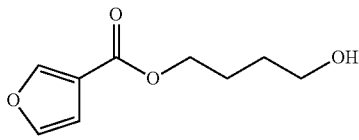 [SMILES: O=C(OCCCCO)c1ccoc1]

Furan-3-carboxylic acid (224 mg, 2 mmol), DCC (453 mg, 2.2 mmol) and DMAP (24 mg) was added to a stirred solution of butane-1,4-diol (540 mg, 6 mmol) in DCM (10 mL). The reaction was stirred at 25° C. for 12 h. After that, the reaction mixture was diluted with saturated aqueous NH$_4$Cl (10 mL) and stirred for 5 min. The aqueous phase was separated and extracted with DCM (5 mL). The combined organic phase was washed with brine (10 mL), dried over Na$_2$SO$_4$ and evaporated. The residue was purified by a silica gel flash column with Hex/EA=10:1-5:1 to yield the titled compound (270 mg, 73%) as a pale yellow oil. $^1$H NMR was performed at 400 MHz with CDCl$_3$ as solvent to characterize the titled compound, results are as follows: δ=8.00 (s, 1H), 7.42 (s, 1H), 6.73 (s, 1H), 4.28 (t, J=6.4 Hz, 2H), 3.70 (t, J=6.4 Hz, 2H), 1.83-1.67 (m, 4H).

Compound 52: 4-(furan-3-carbonyloxy)butanoic Acid

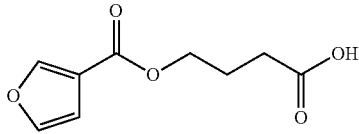 [SMILES: O=C(O)CCCOC(=O)c1ccoc1]

Jones reagent in portions was added to a stirred mixture of 4-hydroxybutyl furan-3-carboxylate (750 mg, 4.09 mmol) and Celite® (diatomaceous earth, 2 g) in acetone (10 mL) at 0° C. The reaction proceeded at 0° C. over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with brine (2 mL×2), dried over Na$_2$SO$_4$ and concentrated. The residue was purified by a silica gel flash column with Hex/EA=3:1 to yield the titled compound (600 mg, 74%) as crystalline solids. $^1$H NMR was performed at 400 MHz with CDCl$_3$ as solvent to characterize the titled compound, results are as follows: δ=8.01 (s, 1H), 7.42 (s, 1H), 6.73 (s, 1H), 4.31 (t, J=6.2 Hz, 2H), 2.51 (t, J=7.4 Hz, 2H), 2.12-2.05 (m, 2H).

Example 1-53

Intermediate Compound 53': 4-hydroxybutyl thiophene-3-carboxylate

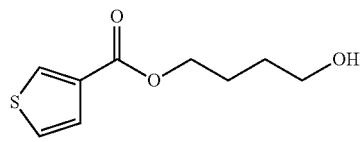 [SMILES: O=C(OCCCCO)c1ccsc1]

Thiophene-3-carboxylic acid (1 g, 7.81 mmol), DCC (1.77 g, 8.59 mmol) and DMAP (10 mg) was added to a stirred solution of butane-1,4-diol (2.1 g, 23.33 mmol) in DCM (50 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (5 mL). The combined organic phase was washed with brine (10 mL), dried over Na$_2$SO$_4$ and evaporated. The residue was purified by a silica gel flash column with Hex/EA=7:1 to afford the crude product, which was further purified by prep-TLC with Hex/EA=1:1 to yield the pure titled compound (600 mg, 38%) as crystalline solids. $^1$H NMR was performed at 400 MHz with CDCl$_3$ as solvent to characterize the titled compound, results are as follows: δ=8.10 (d, J=2.0 Hz, 1H), 7.53 (d, J=5.2 Hz, 1H), 7.31 (dd, J=3.2, 5.2 Hz, 1H), 4.32 (t, J=6.4 Hz, 2H), 3.73 (t, J=6.4 Hz, 2H), 1.90-1.80 (m, 2H), 1.76-1.68 (m, 2H).

Compound 53: 4-(thiophene-3-carbonyloxy)butanoic Acid

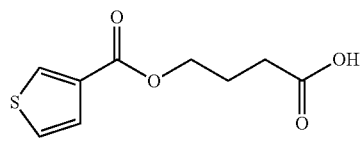 [SMILES: O=C(O)CCCOC(=O)c1ccsc1]

Jones reagent was added in portions to a stirred mixture of 4-hydroxybutyl thiophene-3-carboxylate (400 mg, 2 mmol) and Celite® (diatomaceous earth, 2 g) in acetone (10 mL) at 0° C. The reaction proceeded at 0° C. over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with brine (2 mL×2), dried over Na$_2$SO$_4$ and concentrated. The residue was purified by prep-HPLC to yield the titled compound (100 mg, 23%) as crystalline solids. $^1$H NMR was performed at 400 MHz with CDCl$_3$ as solvent to characterize the titled compound, results are as follows: δ=8.10 (d, J=2.0 Hz, 1H), 7.52 (d, J=5.2 Hz, 1H), 7.31 (dd, J=3.0, 5.0 Hz, 1H), 4.34 (t, J=6.2 Hz, 2H), 2.53 (t, J=7.2 Hz, 2H), 2.13-2.07 (m, 2H).

Example 1-54

Intermediate Compound 54': (S)-1-tert-butyl 2-(4-hydroxybutyl) pyrrolidine-1,2-dicarboxylate

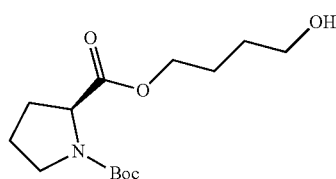 [SMILES: CC(C)(C)OC(=O)N1CCC[C@H]1C(=O)OCCCCO]

(S)-1-(tert-butoxycarbonyl)pyrrolidine-2-carboxylic acid (2 g, 9.3 mmol), DCC (2108 mg, 10.23 mmol) and DMAP (50 mg) was added to a stirred solution of butane-1,4-diol (1674 mg, 18.6 mmol) in DCM (30 mL). The reaction was stirred at 25° C. for 3 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=5:1 to yield the titled compound (1.4 g, 52%) as a colorless oil. $^1$H NMR was performed at 400 MHz with CDCl$_3$ as solvent to characterize the titled compound, results are as follows: δ=4.32-4.12 (m, 3H), 3.71-3.62 (m, 2H), 3.58-3.35 (m, 2H), 2.27-2.16 (m, 1H), 2.02-1.60 (m, 8H), 1.46 (s, 4H), 1.41 (s, 5H).

Compound 54: (S)-4-(1-(tert-butoxycarbonyl)pyrrolidine-2-carbonyloxy)butanoic Acid

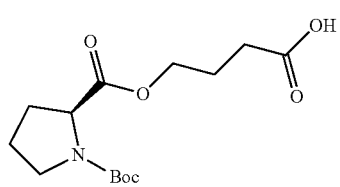 [SMILES: CC(C)(C)OC(=O)N1CCC[C@H]1C(=O)OCCCC(=O)O]

Jones reagent was added in portions to a stirred mixture of (S)-1-tert-butyl 2-(4-hydroxybutyl) pyrrolidine-1,2-dicarboxylate (400 mg, 1.39 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with DCM/MeOH=120:1 to yield the titled compound (200 mg, 48%) as a colorless oil. $^1$H NMR was performed at 400 MHz with CDCl$_3$ as solvent to characterize the titled compound, results are as follows: δ=4.40-4.32 (m, 1H), 4.26-4.07 (m, 2H), 3.58-3.35 (m, 2H), 2.45 (t, J=7.0 Hz, 2H), 2.33-2.12 (m, 2H), 2.01-1.83 (m, 4H), 1.46 (s, 5H), 1.41 (s, 4H).

Example 1-55

Intermediate Compound 55': 4-hydroxybutyl 2-(tert-butoxycarbonylamino)acetate

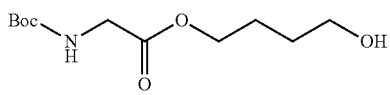 [SMILES: CC(C)(C)OC(=O)NCC(=O)OCCCCO]

2-(tert-butoxycarbonylamino)acetic acid (340 mg, 1.94 mmol), DCC (440 mg, 2.14 mmol) and DMAP (5 mg) was added to a stirred solution of butane-1,4-diol (350 mg, 3.89 mmol) in DCM (30 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=5:1 to yield the titled compound (200 mg 42%) as a white solid. $^1$H NMR was performed at 400 MHz with CDCl$_3$ as solvent to characterize the titled compound, results are as follows: δ=5.00 (br. s., 1H), 4.20 (t, J=6.6 Hz, 2H), 3.90 (d, J=5.2 Hz, 2H), 3.68 (q, J=6.0 Hz, 2H), 1.79-1.72 (m, 2H), 1.67-1.62 (m, 2H), 1.45 (s, 9H), 1.37-1.34 (m, 1H).

Compound 55: 4-(2-(tert-butoxycarbonylamino)acetoxy)butanoic Acid

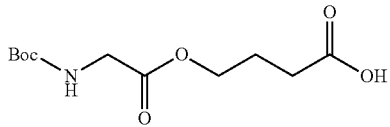 [SMILES: CC(C)(C)OC(=O)NCC(=O)OCCCC(=O)O]

Jones reagent was added in portions to a stirred mixture of 4-hydroxybutyl 2-(tert-butoxycarbonylamino)acetate (200 mg, 0.81 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a flash column (silica gel, DCM/MeOH=100:1 to yield the titled compound (150 mg, 71%) as a colorless oil. $^1$H NMR was performed at 400 MHz with CDCl$_3$ as solvent to characterize the titled compound, results are as follows: δ=5.03 (br. s, 1H), 4.23 (t, J=6.2 Hz, 2H), 3.90 (d, J=5.2 Hz, 2H), 2.45 (t, J=7.2 Hz, 2H), 2.05-1.98 (m, 2H), 1.45 (s, 9H).

Example 1-56

Compound 56: 4-(2-aminoacetoxy)butanoic Acid

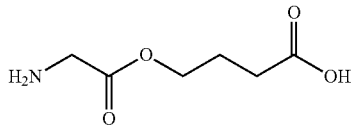 [SMILES: NCC(=O)OCCCC(=O)O]

A solution of 4-(2-(tert-butoxycarbonylamino)acetoxy) butanoic acid (150 mg, 0.57 mmol) in HCl/EA (~2 M, 1.5 mL) was stirred at 25° C. for 24 h. After that, the reaction mixture was filtered and the resulting precipitate was collected, washed with Et$_2$O (0.5 mL), dried in vacuo to yield the titled compound (82 mg, 89%) as a white solid in HCl salt form. $^1$H NMR was performed at 400 MHz with CD$_3$OD as solvent to characterize the titled compound, results are as follows: δ=4.30 (t, J=6.4 Hz, 2H), 3.84 (s, 2H), 2.42 (t, J=7.2 Hz, 2H), 2.03-1.94 (m, 2H).

Example 1-57

Intermediate Compound 57': (S)-4-hydroxybutyl 2-(tert-butoxycarbonylamino)-3-phenylpropanoate

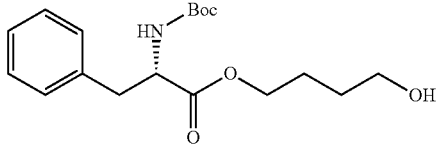 [SMILES: CC(C)(C)OC(=O)N[C@@H](Cc1ccccc1)C(=O)OCCCCO]

(S)-2-(tert-butoxycarbonylamino)-3-phenylpropanoic acid (1 g, 3.37 mmol), DCC (855 mg, 4.15 mmol) and DMAP (10 mg) was added to a stirred solution of butane-1,4-diol (679 mg, 7.54 mmol) in DCM (20 mL). The reaction was stirred at 25° C. for 16 h. After that, the reaction mixture was diluted with saturated aqueous NH$_4$Cl (10 mL) and stirred for 5 min. The aqueous phase was separated and extracted with DCM (10 mL). The combined organic phase was washed with saturated brine (15 mL), dried over anhydrous Na$_2$SO$_4$ and evaporated. The residue was purified by a silica gel flash column with Hex/EA=5:1 to yield the titled compound (700 mg, 55%) as a colorless oil. $^1$H NMR was performed at 400 MHz with CDCl$_3$ as solvent to characterize the titled compound, results are as follows: δ=7.32-7.27 (m, 2H), 7.26-7.21 (m, 1H), 7.14 (d, J=6.8 Hz, 2H), 4.97 (d, J=8.0 Hz, 1H), 4.58-4.53 (m, 1H), 4.19-4.08 (m, 2H), 3.64 (q, J=5.6 Hz, 2H), 3.07 (t, J=4.8 Hz, 2H), 1.72-1.65 (m, 2H), 1.56-1.51 (m, 2H), 1.42 (s, 9H).

Intermediate Compound 57": (S)-4-(2-(tert-butoxycarbonylamino)-3-phenylpropanoyloxy)butanoic Acid

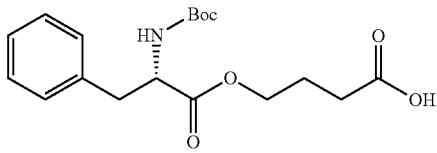 [SMILES: CC(C)(C)OC(=O)N[C@@H](Cc1ccccc1)C(=O)OCCCC(=O)O]

Jones reagent was added in portions to a stirred mixture of (S)-4-hydroxybutyl 2-(tert-butoxycarbonylamino)-3-phenylpropanoate (600 mg, 1.78 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (220 mg, 35%) as a colorless oil. $^1H$ NMR was performed at 400 MHz with $CDCl_3$ as solvent to characterize the titled compound, results are as follows: δ=7.34-7.27 (m, 2H), 7.26-7.20 (m, 1H), 7.14 (d, J=6.8 Hz, 2H), 4.99 (d, J=8.0 Hz, 1H), 4.61-4.51 (m, 1H), 4.22-4.09 (m, 2H), 3.06 (d, J=6.0 Hz, 2H), 2.34 (t, J=7.2 Hz, 2H), 1.97-1.89 (m, 2H), 1.42 (s, 9H).

Compound 57:
(S)-4-(2-amino-3-phenylpropanoyloxy)butanoic Acid

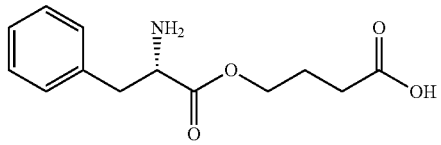 [SMILES: N[C@@H](Cc1ccccc1)C(=O)OCCCC(=O)O]

A solution of (S)-4-(2-(tert-butoxycarbonylamino)-3-phenylpropanoyloxy) butanoic acid (180 mg, 0.51 mmol) in HCl/EA (~2 M, 2 mL) stirred at 25° C. for 24 h. After that, the reaction mixture was filtered and the resulting precipitate was collected, washed with $Et_2O$ (0.5 mL), dried in vacuo to yield the titled compound (100 mg, 78%) as a white solid in HCl salt form. $^1H$ NMR was performed at 400 MHz with $CD_3OD$ as solvent to characterize the titled compound, results are as follows: δ=7.41-7.31 (m, 3H), 7.27-7.25 (m, 2H), 4.30 (t, J=7.0 Hz, 1H), 4.26-4.19 (m, 2H), 3.25-3.15 (m, 2H), 2.28 (t, J=7.2 Hz, 2H), 1.92-1.86 (m, 2H).

Example 1-58

Intermediate Compound 58': (S)-4-hydroxybutyl 2-(tert-butoxycarbonylamino)-3-methylbutanoate

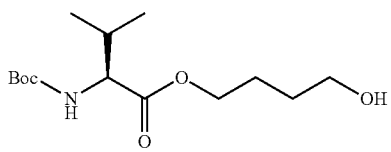 [SMILES: CC(C)[C@H](NC(=O)OC(C)(C)C)C(=O)OCCCCO]

(S)-2-(tert-butoxycarbonylamino)-3-methylbutanoic acid (1 g, 4.61 mmol), DCC (1044 mg, 5.07 mmol) and DMAP (10 mg) was added to a stirred solution of butane-1,4-diol (829 mg, 9.21 mmol) in DCM (20 mL). The reaction was stirred at 25° C. for 16 h. After that, the reaction mixture was diluted with saturated aqueous $NH_4Cl$ (10 mL) and stirred for 5 min. The aqueous phase was separated and extracted with DCM (10 mL). The combined organic phase was washed with saturated brine (15 mL), dried over anhydrous $Na_2SO_4$ and evaporated. The residue was purified by a silica gel flash column with Hex/EA=5:1 to yield the titled compound (700 mg, 53%) as a colorless oil. $^1H$ NMR was performed at 400 MHz with $CDCl_3$ as solvent to characterize the titled compound, results are as follows: δ=5.07 (d, J=8.8 Hz, 1H), 4.16-4.11 (m, 3H), 3.62 (t, J=6.2 Hz, 2H), 2.32 (br. s., 1H), 2.12-2.04 (m, 1H), 1.75-1.68 (m, 2H), 1.62-1.56 (m, 2H), 1.40 (s, 9H), 0.92 (d, J=7.2 Hz, 3H), 0.85 (d, J=7.2 Hz, 3H).

Intermediate Compound 58'': (S)-4-(2-(tert-butoxycarbonylamino)-3-methylbutanoyloxy)butanoic Acid

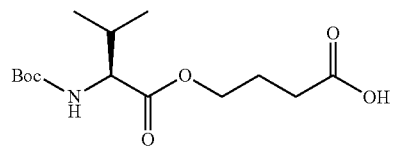 [SMILES: CC(C)[C@H](NC(=O)OC(C)(C)C)C(=O)OCCCC(=O)O]

Jones reagent was added in portions to a stirred mixture of (S)-4-hydroxybutyl 2-(tert-butoxycarbonylamino)-3-methylbutanoate (500 mg, 1.73 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous $Na_2SO_4$ and concentrated. The residue was purified by a silica gel flash column with Hex/EA=10:1-5:1 to yield the titled compound (170 mg, 32%) as a white solid. $^1H$ NMR was performed at 400 MHz with $CDCl_3$ as solvent to characterize the titled compound, results are as follows: δ=5.03 (d, J=9.2 Hz, 1H), 4.30-4.24 (m, 1H), 4.22-4.13 (m, 2H), 2.46 (t, J=7.4 Hz, 2H), 2.16-2.08 (m, 1H), 2.06-1.96 (m, 2H), 1.45 (s, 9H), 0.96 (d, J=6.8 Hz, 3H), 0.89 (d, J=6.4 Hz, 3H).

Compound 58:
(S)-4-(2-amino-3-methylbutanoyloxy)butanoic Acid

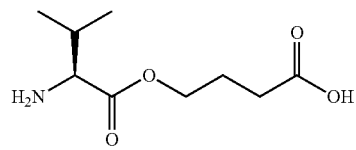

A solution of (S)-4-(2-(tert-butoxycarbonylamino)-3-methylbutanoyloxy)butanoic acid (104 mg, 0.34 mmol) in HCl/EA (~2 M, 1.5 mL) stirred at 25° C. for 24 h. After that, the reaction mixture was filtered and the resulting precipitate was collected, washed with $Et_2O$ (0.5 mL), dried in vacuo to yield the titled compound (50 mg, 71%) as a white solid in HCl salt form. $^1H$ NMR was performed at 400 MHz with $CD_3OD$ as solvent to characterize the titled compound, results are as follows: δ=4.33-4.26 (m, 2H), 3.92 (d, J=4.8 Hz, 1H), 2.42 (t, J=7.2 Hz, 2H), 2.34-2.25 (m, 1H), 2.05-1.94 (m, 2H), 1.06 (d, J=6.8 Hz, 6H).

A suspension of the above white solid (800 mg, 3.3 mmol) in ethanol (4 mL) was stirred at 80° C. for around 30 min and a clear solution was formed. Then the solution was gradually cooled to 25° C., propylene oxide (580 mg, 10 mmol) was added dropwise. The reaction was stirred at 25° C. for 16 h and then the resultant suspension was filtered. The white solid was collected, washed with cold ethanol, dried in vacuo to afford the titled compound (510 mg, 75%) in free salt form. $^1$H NMR was performed at 400 MHz with $d_6$-DMSO as solvent to characterize the titled compound, results are as follows: δ=4.10-3.99 (m, 2H), 3.11 (d, J=5.2 Hz, 1H), 2.29 (t, J=7.4 Hz, 2H), 1.90-1.74 (m, 3H), 0.87 (d, J=6.8 Hz, 3H), 0.82 (d, J=6.4 Hz, 3H).

Example 1-59

Intermediate Compound 59': 4-hydroxybutyl 2-(p-tolyl)acetate

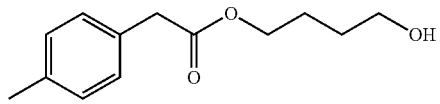 [SMILES: Cc1ccc(CC(=O)OCCCCO)cc1]

2-(p-tolyl)acetic acid (1 g, 6.67 mmol), DCC (1.5 g, 7.33 mmol) and DMAP (10 mg) was added to a stirred solution of butane-1,4-diol (3 g, 33.33 mmol) in DCM (50 mL). The reaction was stirred at 25° C. for 16 h. After that, the reaction mixture was filtered and the filtrate was washed with saturated aqueous NH$_4$Cl (20 mL). The resultant organic phase was washed with brine (20 mL), dried over Na$_2$SO$_4$ and concentrated. The residue was purified by a silica gel flash column with Hex/EA=3:1 to afford the titled compound (1.1 g, 74%) as a colorless oil. $^1$H NMR was performed at 400 MHz with CDCl$_3$ as solvent to characterize the titled compound, results are as follows: δ=7.18-7.12 (m, 4H), 4.12 (t, J=6.6 Hz, 2H), 3.64 (t, J=6.4 Hz, 2H), 3.58 (s, 2H), 2.33 (s, 3H), 1.75-1.68 (m, 2H), 1.62-1.55 (m, 2H).

Compound 59: 4-(2-(p-tolyl)acetoxy)butanoic Acid

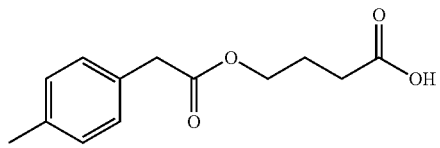 [SMILES: Cc1ccc(CC(=O)OCCCC(=O)O)cc1]

Jones reagent was added dropwise to a stirred mixture of 4-hydroxybutyl 2-(p-tolyl)acetate (800 mg, 3.60 mmol) and Celite® (diatomaceous earth, 1.6 g) in acetone (15 mL) at 0° C. The reaction proceeded at 0° C. over 1 h and the reaction progress was monitored by TLC. After completion, the reaction was quenched with drops of isopropanol, diluted with EA (30 mL), and then filtered. The filtered cake was washed with EA (10 mL) and the combined filtrate was washed with brine (10 mL×2), dried over Na$_2$SO$_4$ and concentrated. The residue was purified by a silica gel flash column with Hex/EA=2:1 to afford the titled compound (500 mg, 59%) as crystalline solids. $^1$H NMR was performed at 400 MHz with CDCl$_3$ as solvent to characterize the titled compound, results are as follows: δ=7.17-7.12 (m, 4H), 4.14 (t, J=6.2 Hz, 2H), 3.57 (s, 2H), 2.41 (t, J=7.2 Hz, 2H), 2.33 (s, 3H), 1.99-1.93 (m, 2H).

Example 1-60

Intermediate Compound 60': (R)-4-hydroxybutyl 2-(tert-butoxycarbonylamino)-3-methylbutanoate

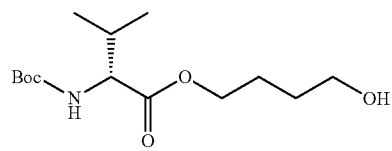 [SMILES: CC(C)[C@@H](NC(=O)OC(C)(C)C)C(=O)OCCCCO]

DCC (3.1 g, 15.21 mmol) and DMAP (17 mg, 0.14 mmol) was added to a stirred suspension of (R)-2-(tert-butoxycarbonylamino)-3-methylbutanoic acid (3.0 g, 13.82 mmol) and butane-1,4-diol (3.7 g, 41.47 mmol) in DCM (40 mL) at 0° C. The reaction was allowed to warm up gradually and stirred at 25° C. for 16 h. After that, the reaction mixture was filtered and the filtered cake was washed with DCM (10 mL). The combined filtrate was washed with saturated aqueous NH$_4$Cl (10 mL×2), dried over Na$_2$SO$_4$ and evaporated. The residue was purified by a silica gel flash column with DCM/EA=20:1 to afford the titled compound (2.5 g, 63%) as a colorless oil. $^1$H NMR was performed at 400 MHz with CDCl$_3$ as solvent to characterize the titled compound, results are as follows: S=5.02 (d, J=8.4 Hz, 1H), 4.20-4.16 (m, 2H), 3.68 (q, J=6.0 Hz, 2H), 2.16-2.08 (m, 1H), 1.79-1.70 (m, 2H), 1.69-1.64 (m, 2H), 1.44 (s, 9H), 0.96 (d, J=6.8 Hz, 3H), 0.89 (d, J=6.8 Hz, 3H).

Intermediate Compound 60": (R)-4-(2-(tert-butoxycarbonylamino)-3-methylbutanoyloxy)butanoic Acid

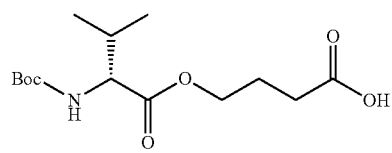 [SMILES: CC(C)[C@@H](NC(=O)OC(C)(C)C)C(=O)OCCCC(=O)O]

Jones reagent was dropwise added to a stirred mixture of (R)-4-hydroxybutyl 2-(tert-butoxycarbonylamino)-3-methylbutanoate (2.5 g, 8.65 mmol) and Celite® (diatomaceous earth, 5.0 g) in acetone (25 mL) at 0° C. The reaction proceeded at 0° C. over 1 h and the reaction progress was monitored by TLC. After completion, the reaction was quenched with drops of isopropanol, diluted with EA (25 mL), and then filtered. The filtered cake was washed with EA (25 mL) and the combined filtrate was washed with brine (20 mL×2), dried over Na$_2$SO$_4$ and concentrated. The residue was purified by a silica gel flash column with DCM/EA=20:1-3:1 to afford the titled compound (1.1 g, 42%) as a white solid. $^1$H NMR was performed at 400 MHz with CDCl$_3$ as solvent to characterize the titled compound, results are as follows: δ=5.03 (d, J=8.8 Hz, 1H), 4.26-4.18 (m, 2H), 2.45 (t, J=7.4 Hz, 2H), 2.14-2.10 (m, 1H), 2.03-2.00 (m, 2H), 1.45 (s, 9H), 0.96 (d, J=6.8 Hz, 3H), 0.89 (d, J=6.8 Hz, 3H).

Compound 60: (R)-4-(2-amino-3-methylbutanoyloxy)butanoic Acid

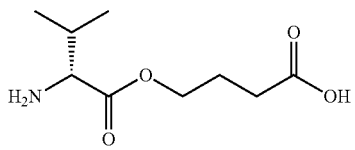

(R)-4-(2-(tert-butoxycarbonylamino)-3-methylbutanoyloxy)butanoic acid (400.0 mg, 1.32 mmol) was added to a stirred solution of HCl/EA (~2 M, 2 mL) at 0° C. The reaction was allowed to warm up gradually and stirred at 25° C. for 16 h. After that, the resulting suspension was filtered. The white precipitate was collected, washed with EA (2 mL) and dried in vacuo to afford the titled compound (184.0 mg, 58%) as a white solid in HCl salt form. $^1$H NMR was performed at 400 MHz with $D_2O$ as solvent to characterize the titled compound, results are as follows: $\delta$=4.32 (t, J=5.6 Hz, 2H), 4.03 (d, J=4.4 Hz, 1H), 2.51 (t, J=7.2 Hz, 2H), 2.39-2.35 (m, 1H), 2.03 (t, J=6.6 Hz, 2H), 1.04 (t, J=7.2 Hz, 6H).

Example 1-61

Intermediate Compound 61': (S)-4-hydroxybutyl 2-(tert-butoxycarbonylamino)propanoate

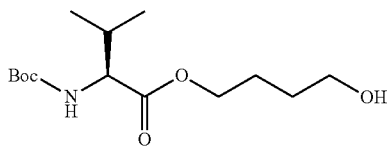 [SMILES: CC(C)[C@H](NC(=O)OC(C)(C)C)C(=O)OCCCCO]

A solution of (Boc)$_2$O (13.5 g, 61.80 mmol) in 1,4-dioxane (56 mL) was added to a stirred solution (S)-2-aminopropanoic acid (5.0 g, 56.18 mmol) in water (56 mL) and aqueous NaOH (56.2 mL, 1 M) at 0° C. The reaction was allowed to warm up gradually and stirred at 25° C. for 16 h. After that, the reaction mixture was cooled to 0° C., then acidified with HCl (2 M) until pH=2-3. The mixture was diluted with EA (56 mL), the aqueous phase was separated and extracted with EA (56 mL×3). The combined organic phase was washed with brine (56 mL), dried over Na$_2$SO$_4$ and evaporated to afford the crude (S)-2-(tert-butoxycarbonylamino)propanoic acid (9.0 g) as a white solid, which was used directly for the next step without further purification.

DCC (4.4 g, 21.16 mmol) and DMAP (25 mg) was added to a stirred suspension of the above crude (S)-2-(tert-butoxycarbonylamino)propanoic acid (4.0 g) and butane-1,4-diol (5.7 g, 63.49 mmol) in DCM (50 mL) at 0° C. The reaction was allowed to warm up gradually and stirred at 25° C. for 16 h. After that, the reaction mixture was filtered, the filtered cake was washed with DCM (10 mL). The combined filtrate was washed with saturated aqueous NH$_4$Cl (15 mL×2), dried over Na$_2$SO$_4$ and evaporated. The residue was purified by a silica gel flash column with PE/EA=4:1-1:1 to afford the titled compound (3.0 g, 55%) as a colorless oil. $^1$H NMR was performed at 400 MHz with CDCl$_3$ as solvent to characterize the titled compound, results are as follows: $\delta$=5.02 (br. s., 1H), 4.29 (t, J=6.8 Hz, 1H), 4.18 (t, J=6.4 Hz, 2H), 3.68 (q, J=6.0 Hz, 2H), 1.79-1.72 (m, 2H), 1.68-1.60 (m, 2H), 1.44 (s, 9H), 1.38 (d, J=7.2 Hz, 3H).

Intermediate Compound 61'': (S)-4-(2-(tert-butoxycarbonylamino)propanoyloxy)butanoic Acid

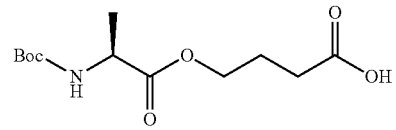 [SMILES: C[C@H](NC(=O)OC(C)(C)C)C(=O)OCCCC(=O)O]

Jones reagent was dropwise added to a stirred mixture of (S)-4-hydroxybutyl 2-(tert-butoxycarbonylamino)propanoate (3.0 g, 11.49 mmol) and Celite® (diatomaceous earth, 6.0 g) in acetone (30 mL) at 0° C. The reaction proceeded at 0° C. over 1 h and the reaction progress was monitored by TLC. After completion, the reaction was quenched with drops of isopropanol, diluted with EA (100 mL), and then filtered. The filtered cake was washed with EA (20 mL) and the combined filtrate was washed with brine (30 mL×2), dried over Na$_2$SO$_4$ and concentrated. The residue was purified by a silica gel flash column with DCM/EA=20:1 to afford the titled compound (1.8 g, 57%) as a colorless oil. $^1$H NMR was performed at 400 MHz with CDCl$_3$ as solvent to characterize the titled compound, results are as follows: $\delta$=5.06 (br. s., 1H), 4.31-4.16 (m, 3H), 2.45 (t, J=7.2 Hz, 2H), 2.02-1.97 (m, 2H), 1.44 (s, 9H), 1.38 (d, J=7.2 Hz, 3H).

Compound 61: (S)-4-(2-aminopropanoyloxy)butanoic Acid

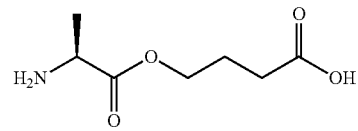

(S)-4-(2-(tert-butoxycarbonylamino)propanoyloxy)butanoic acid (200.0 mg, 0.73 mmol) was added to a stirred solution of HCl/EA (1.0 mL, ~2 M) at 0° C. The reaction was allowed to warm up gradually and stirred at 25° C. for 16 h. After that, the reaction mixture was evaporated, the residue was purified by prep-HPLC to afford the titled compound (80.0 mg, 52%) as a colorless oil in HCl salt form. $^1$H NMR was performed at 400 MHz with CD$_3$OD as solvent to characterize the titled compound, results are as follows: $\delta$=4.31-4.27 (m, 2H), 4.11 (q, J=7.2 Hz, 1H), 2.48-2.41 (m, 2H), 2.04-1.97 (m, 2H), 1.55 (dd, J=1.6, 7.2 Hz, 3H).

Example 1-62

Intermediate Compound 62': (S)-4-hydroxybutyl 2-acetamidopropanoate

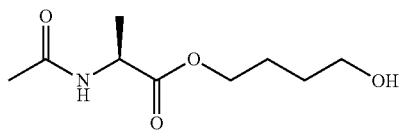

Ac₂O (6.8 g, 66.67 mmol) was added to a stirred suspension of (S)-2-aminopropanoic acid (5.0 g, 56.18 mmol) in HOAc (25 mL). The reaction was stirred at 25° C. for 16 h. After that, the reaction mixture was evaporated to yield the crude (S)-2-acetamidopropanoic acid as a white solid (8.0 g), which was used directly for next step without further purification.

DCC (3.1 g, 15.28 mmol) and DMAP (20 mg) was added to a stirred suspension of the above (S)-2-acetamidopropanoic acid (2.0 g, 15.28 mmol) and butane-1,4-diol (4.1 g, 45.80 mmol) in DCM (50 mL). The reaction was stirred at 25° C. for 16 h. After that, the reaction mixture was filtered and the filtrate was concentrated. The residue was purified by prep-HPLC to afford the titled compound (2.0 g, 67%) as a colorless oil. ¹H NMR was performed at 400 MHz with CDCl₃ as solvent to characterize the titled compound, results are as follows: δ=6.12 (br. s., 1H), 4.59-4.52 (m, 1H), 4.24-4.13 (m, 2H), 3.67 (t, J=6.4 Hz, 2H), 2.01 (s, 3H), 1.77-1.72 (m, 2H), 1.66-1.59 (m, 2H), 1.40 (d, J=7.6 Hz, 3H).

Compound 62:
(S)-4-(2-acetamidopropanoyloxy)butanoic Acid

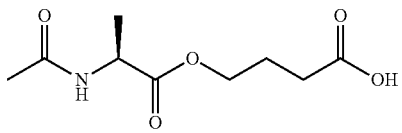

Jones reagent was dropwise added to a stirred mixture of (S)-4-hydroxybutyl 2-acetamidopropanoate (660 mg, 3.25 mmol) and Celite® (diatomaceous earth, 1.2 g) in acetone (10 mL) at 0° C. The reaction proceeded at 0° C. over 1 h and the reaction progress was monitored by TLC. After completion, the reaction was quenched with drops of isopropanol, diluted with EA (10 mL), and then filtered. The filtered cake was washed with EA (10 mL) and the combined filtrate was washed with brine (10 mL×2), dried over Na₂SO₄ and concentrated. The residue was purified by prep-HPLC to afford the titled compound (300 mg, 42%) as a colorless oil. ¹H NMR was performed at 400 MHz with CDCl₃ as solvent to characterize the titled compound, results are as follows: δ=6.25 (d, J=6.4 Hz, 1H), 4.61-4.54 (m, 1H), 4.28-4.15 (m, 2H), 2.44 (t, J=7.0 Hz, 2H), 2.03 (s, 3H), 2.07-1.97 (m, 2H), 1.40 (d, J=7.2 Hz, 3H).

Scheme 3:

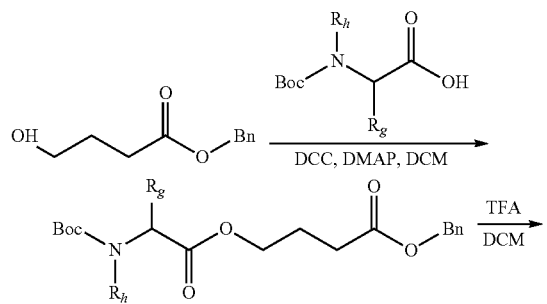

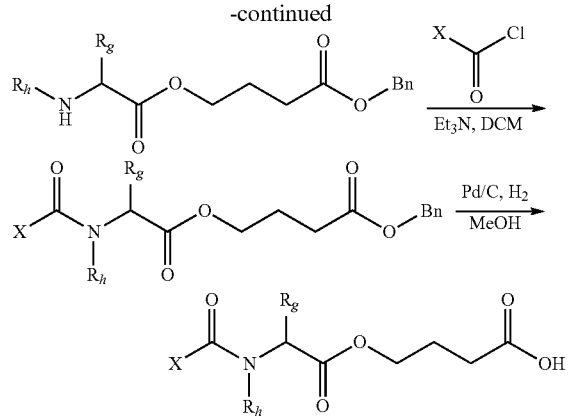

Example 1-63

Intermediate Compound 63': benzyl 4-(2-(tert-butoxycarbonyl)aminoacetoxy)butanoate

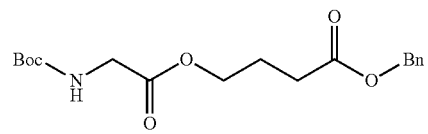 [SMILES: CC(C)(C)OC(=O)NCC(=O)OCCCC(=O)OCc1ccccc1]

A mixture of N-Boc glycine (2.0 g, 11.4 mmol), benzyl 4-hydroxybutanoate (2.7 g 13.7 mmol), DCC (3.1 g, 14.8 mmol) and DMAP (5 mg) in DCM (20 mL) was stirred at 25° C. for 16 h. The reaction mixture was filtered and the filtrate was washed with aqueous saturated NH₄Cl (2×20 mL). The organic layer was dried over Na₂SO₄, filtered and concentrated. The residue was purified by a silica gel flash column with PE/EA=10:1-1:1 to afford the titled compound (2.0 g, 50%) as a colorless oil. ¹H NMR was performed at 400 MHz with CDCl₃ as solvent to characterize the titled compound, results are as follows: δ=7.45-7.27 (m, 5H), 5.13 (s, 2H), 4.99 (br. s., 1H), 4.20 (t, J=6.2 Hz, 2H), 3.88 (d, J 4.4 Hz, 2H), 246 (t, J=7.4 Hz, 2H), 2.04-1.97 (m, 2H), 1.45 (s, 9H).

Intermediate Compound 63": benzyl 4-(2-aminoacetoxy)butanoate

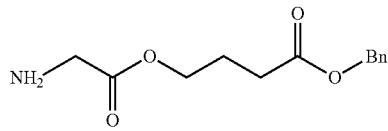 [SMILES: NCC(=O)OCCCC(=O)OCc1ccccc1]

TFA (3.0 mL) was added to a solution of benzyl 4-(2-(tert-butoxycarbonyl)aminoacetoxy)butanoate (1.60 g, 4.56 mmol) in DCM (15 mL) at 0° C., and the reaction was stirred at the same temperature for 2 h. After that, solvent was evaporated to afford the titled compound (1.2 g), which was used directly for the next step without further purification.

Intermediate Compound 63''': benzyl 4-(2-propionamidoacetoxy)butanoate

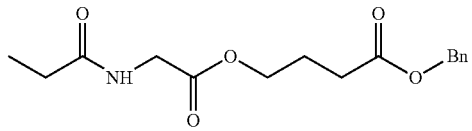 [SMILES: CCC(=O)NCC(=O)OCCCC(=O)OCc1ccccc1]

Propionyl chloride (162 mg, 1.75 mmol) was dropwise added to a solution of benzyl 4-(2-aminoacetoxy)butanoate (400 mg, 1.59 mmol) and Et₃N (0.66 mL, 4.78 mmol) in DCM (10 mL) at 0° C. The reaction was allowed to warm up and stirred at 25° C. for 16 h. After that, the reaction was quenched by water (10 mL) with stirring for 5 min. The aqueous phase was extracted with DCM (10 mL×3), the combined organic phase was washed with brine (20 mL), dried over Na₂SO₄ and concentrated. The residue was purified by silica gel flash column with PE/EA=1:1 to afford the titled compound (440 mg, 90%) as colorless oil.

Compound 63: 4-(2-propionamidoacetoxy)butanoic Acid

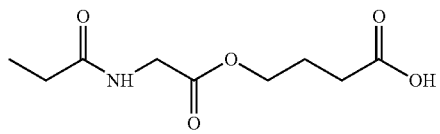

Pd/C (50 mg) was added to a solution of benzyl 4-(2-propionamidoacetoxy)butanoate (400 mg, 1.3 mmol) in MeOH (10 mL), and the mixture was stirred at 25° C. for 16 h under H₂ atmosphere. After that, the reaction mixture was filtered and the filtrate was concentrated. The residue was purified by a silica gel flash column with PE/EA=1:50 to afford the titled compound (170 mg, 60%) as a white solid. $^1$H NMR was performed at 400 MHz with CD₃OD as solvent to characterize the titled compound, results are as follows: δ=4.18 (t, J=6.2 Hz, 2H), 3.92 (s, 2H), 2.39 (t, J=7.4 Hz, 2H), 2.27 (q, J=7.6 Hz, 2H), 1.98-1.91 (m, 2H), 1.14 (t, J=7.6 Hz, 3H).

Example 1-64

Intermediate Compound 64': benzyl 4-(2-isobutyramidoacetoxy)butanoate

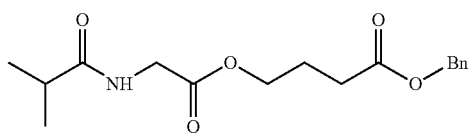 [SMILES: CC(C)C(=O)NCC(=O)OCCCC(=O)OCc1ccccc1]

Isobutyryl chloride (0.8 g, 7.5 mmol) was added dropwise to a solution of benzyl 4-(2-aminoacetoxy)butanoate (1.57 g, 6.26 mmol) and Et₃N (1.58 mL, 15.7 mmol) in DCM (20 mL) at 0° C. The reaction was stirred at 25° C. for 16 h and then washed with brine (2×10 mL). The organic layer was dried over Na₂SO₄, filtered and concentrated. The residue was purified by prep-HPLC to afford the titled compound (0.8 g, 40%) as a colorless oil. $^1$H NMR was performed at 600 MHz with CDCl₃ as solvent to characterize the titled compound, results are as follows: S=7.45-7.27 (m, 5H), 5.93 (br. s., 1H), 5.12 (s, 2H), 4.20 (t, J=6.3 Hz, 2H), 4.00 (d, J=4.8 Hz, 2H), 2.50-2.37 (m, 3H), 2.04-1.99 (m, 2H), 1.18 (d, J=7.2 Hz, 6H).

Compound 64: 4-(2-isobutyramidoacetoxy)butanoic Acid

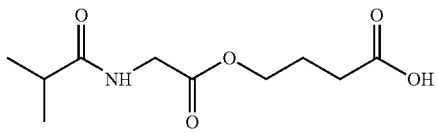 [SMILES: CC(C)C(=O)NCC(=O)OCCCC(=O)O]

Pd/C (75 mg) was added to a solution of benzyl 4-(2-isobutyramidoacetoxy)butanoate (0.75 g, 2.3 mmol) in EA (10 mL). The reaction was stirred under H₂ atmosphere for 16 h at 25° C. The reaction was filtered and the filtrate was concentrated. The residue was purified by a silica gel flash column with PE/EA=5:1-3:1 to afford the titled compound (270 mg, 50%) as a white solid. $^1$H NMR was performed at 400 MHz with CDCl₃ as solvent to characterize the titled compound, results are as follows: S=6.04 (br. s., 1H), 4.24 (t, J=6.2 Hz, 2H), 4.03 (d, J=5.2 Hz, 2H), 2.57-2.36 (m, 3H), 2.06-1.99 (m, 2H), 1.18 (d, J=7.2 Hz, 6H).

Example 1-65

Intermediate Compound 65': benzyl 4-(2-(tert-butoxycarbonyl)methylaminoacetoxy)butanoate

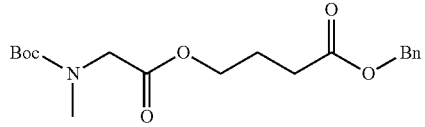 [SMILES: CN(CC(=O)OCCCC(=O)OCc1ccccc1)C(=O)OC(C)(C)C]

A mixture of 2-((tert-butoxycarbonyl)methylamino)acetic acid (5.0 g, 26.45 mmol), benzyl 4-hydroxybutanoate (4.6 g, 23.71 mmol), DCC (6.0 g, 29.07 mmol) and DMAP (cat.) in DCM (100 mL) was stirred at 25° C. for 16 h. After that, the reaction mixture was filtered and the filtrate was concentrated. The residue was purified by a silica gel flash column with PE/EA=10:1 to afford the titled compound (8.0 g, 83%) as a colorless oil. $^1$H NMR was performed at 400 MHz with CDCl₃ as solvent to characterize the titled compound, results are as follows: δ=7.35-7.26 (m, 5H), 5.12 (s, 2H), 4.17 (q, J=5.6 Hz, 2H), 3.94 (s, 1H), 3.86 (s, 1H), 2.90 (d, J=6.8 Hz, 3H), 2.45 (t, J=7.4 Hz, 2H), 2.02-1.97 (m, 2H), 1.43 (d, J=19.6 Hz, 9H).

Intermediate Compound 65'': benzyl 4-(2-(N-methylacetamido)acetoxy)butanoate

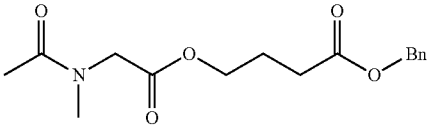 [SMILES: CC(=O)N(C)CC(=O)OCCCC(=O)OCc1ccccc1]

TFA (8.0 mL) was added to a solution of benzyl 4-(2-(tert-butoxycarbonyl)methylaminoacetoxy)butanoate (8.0 g, 21.89 mmol) in DCM (80 mL) at 0° C., the reaction was stirred at the same temperature for 2 h. After that, solvent was evaporated, the residue (5.8 g) was used directly for next step.

The above residue (5.8 g) was dissolved in DCM (60 mL), to which Et₃N (9.2 mL, 65.58 mmol) was added, followed by addition of acetyl chloride (3.4 g, 43.72 mmol) at 0° C. The reaction was allowed to warm up and stirred at 25° C. for 16 h. After that, solvent was evaporated, and the residue was purified by prep-HPLC to afford the titled compound (4.0 g, 59%) as a colorless oil. $^1$H NMR was performed at 400 MHz with CDCl₃ as solvent to characterize the titled compound, results are as follows: δ-7.35-7.31 (m, 5H), 5.10 (s, 2H), 4.14 (t, J=6.2 Hz, 2H), 4.06 (s, 2H), 3.03 (s, 3H), 2.43 (t, J=7.4 Hz, 2H), 2.10 (s, 2H), 2.11-1.96 (m, 3H).

Compound 65:
4-(2-(N-methylacetamido)acetoxy)butanoic Acid

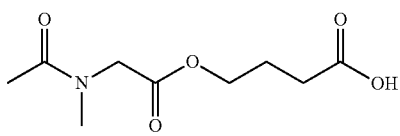

Pd/C (400 mg) was added to a solution of benzyl 4-(2-(N-methylacetamido)acetoxy)butanoate (4.0 g, 13.01 mmol) in MeOH (40 mL), and the reaction was stirred at 25° C. for 16 h under H₂ atmosphere. After that, the reaction mixture was filtered. The filtrate was concentrated and the residue was purified by a silica gel flash column with PE/EA=1:10 to afford the titled compound (1.2 g, 42%) as a colorless oil. $^1$H NMR was performed at 400 MHz with CDCl₃ as solvent to characterize the titled compound, results are as follows: δ=5.92 (br. s., 1H), 4.20 (t, J=6.2 Hz, 2H), 4.11 (s, 2H), 3.09 (s, 3H), 2.42 (t, J=7.2 Hz, 2H), 2.16 (s, 3H), 2.02-1.95 (m, 2H).

Scheme 4:

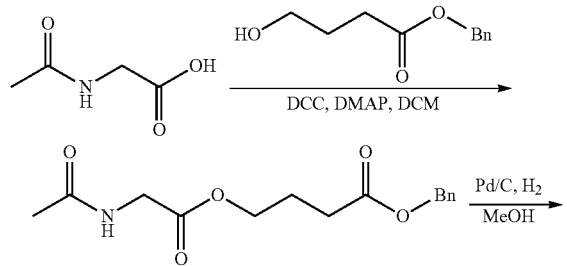

Example 1-66

Intermediate Compound 66': benzyl 4-(2-acetamidoacetoxy)butanoate

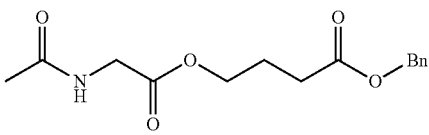 [SMILES: CC(=O)NCC(=O)OCCCC(=O)OCc1ccccc1]

2-acetamidoacetic acid (362 mg, 3.09 mmol), DCC (584 mg, 2.83 mmol) and DMAP (5 mg) was added to a stirred solution of benzyl 4-hydroxybutanoate (500 mg, 2.58 mmol) in DCM (20 mL). The reaction was stirred at 25° C. for 16 h. After that, the reaction mixture was filtered. The filtrate was washed with saturated aqueous NH₄Cl (15 mL), the organic phase was separated, washed with brine (10 mL), dried over Na₂SO₄ and concentrated. The residue was purified by prep-HPLC to afford the titled compound (320 mg, 42%) as crystalline solids. $^1$H NMR was performed at 400 MHz with CD₃OD as solvent to characterize the titled compound, results are as follows: δ=7.36-7.31 (m, 5H), 5.13 (s, 2H), 4.17 (t, J=6.2 Hz, 2H), 3.88 (s, 2H), 2.48 (t, J=7.4H, 2H), 2.01-1.94 (m, 5H).

Compound 66: 4-(2-acetamidoacetoxy)butanoic Acid

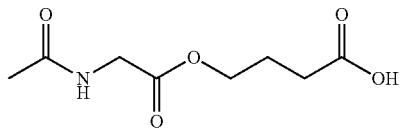

Pd/C (30 mg) was added to a solution of benzyl 4-(2-acetamidoacetoxy)butanoate (280 mg, 0.96 mmol) in methanol (10 mL), the reaction was stirred at 25° C. under H₂ atmosphere for 16 h. After completion, the reaction mixture was filtered through Celite® (diatomaceous earth) and the filtrate was concentrated. The residue was purified by prep-HPLC to afford the titled compound (110 mg, 57%) as crystalline solids. $^1$H NMR was performed at 400 MHz with CD₃OD as solvent to characterize the titled compound, results are as follows: δ=4.18 (t, J=6.4 Hz, 2H), 3.92 (s, 2H), 2.39 (t, J=7.4 Hz, 2H), 2.00 (s, 3H), 1.98-1.91 (m, 2H).

Example 1-67

Scheme 5:

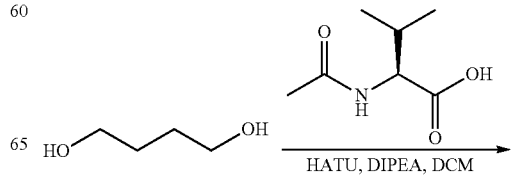

-continued

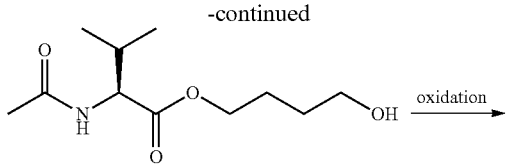

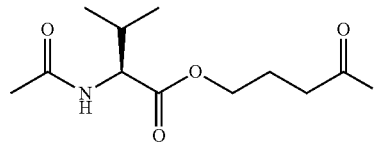

Intermediate Compound 67': (S)-4-hydroxybutyl 2-acetamido-3-methylbutanoate

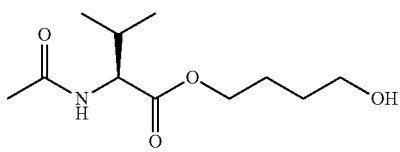 [SMILES: CC(=O)N[C@H](C(=O)OCCCCO)C(C)C]

HATU (5258 mg, 13.84 mmol) and DIPEA (3245 mg, 25.16 mmol) was added to a stirred solution of (S)-2-acetamido-3-methylbutanoic acid (2 g, 12.58 mmol) and butane-1,4-diol (3396 mg, 37.74 mmol) in DCM (50 mL). The reaction was stirred at 25° C. for 16 h. After that, the mixture was concentrated and the residue was purified by prep-HPLC to afford the titled compound (600 mg, 21%) as a colorless oil. $^1$H NMR was performed at 400 MHz with $CDCl_3$ as solvent to characterize the titled compound, results are as follows: δ=5.96 (d, J=8.0 Hz, 1H), 4.54 (dd, J=5.0, 8.6 Hz, 1H), 4.26-4.11 (m, 2H), 3.69 (t, J=6.4 Hz, 2H), 2.18-2.11 (m, 1H), 2.05 (s, 3H), 1.79-1.72 (m, 2H), 1.69-1.65 (m, 2H), 0.95 (d, J=6.8 Hz, 3H), 0.91 (d, J=6.8 Hz, 3H).

Compound 67:
(S)-4-(2-acetamido-3-methylbutanoyloxy)butanoic Acid

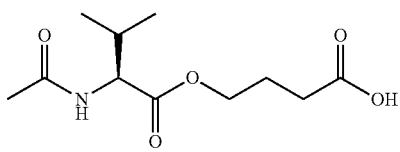 [SMILES: CC(=O)N[C@H](C(=O)OCCCC(=O)O)C(C)C]

Jones reagent was added dropwise to a stirred mixture of (S)-4-hydroxybutyl 2-acetamido-3-methylbutanoate (500 mg, 2.16 mmol) and Celite® (diatomaceous earth, 1 g) in acetone (10 mL) at 0° C. The reaction proceeded at 0° C. over 1 h and the reaction progress was monitored by TLC. After completion, the reaction mixture was quenched by drops of isopropanol, diluted with EA (10 mL) and then filtered. The filtered cake was washed with EA (10 mL), the combined filtrate was washed with brine (5 mL×2), dried over $Na_2SO_4$ and concentrated. The residue was purified by prep-HPLC to afford the titled compound (190 mg, 36%) as crystalline solids. $^1$H NMR was performed at 400 MHz with $CDCl_3$ as solvent to characterize the titled compound, results are as follows: δ=6.18 (d, J=7.2 Hz, 1H), 4.55 (dd, J=4.8, 8.4 Hz, 1H), 4.30-4.24 (m, 1H), 4.20-4.14 (m, 1H), 2.47 (t, J=7.0 Hz, 2H), 2.20-2.12 (m, 1H), 2.09 (s, 3H), 2.06-1.98 (m, 2H), 0.95 (d, J=6.8 Hz, 3H), 0.91 (d, J=6.8 Hz, 3H).

Scheme 6:

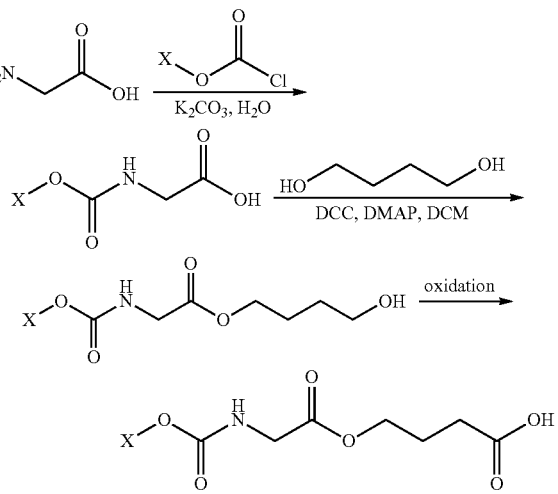

Example 1-68

Intermediate Compound 68':
2-(ethoxycarbonylamino)acetic Acid

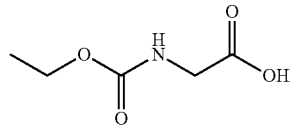

Ethyl carbonochloridate (3.8 g, 34.6 mmol) was dropwise added to solution of glycine (2.0 g, 26.6 mmol) and $K_2CO_3$ (9.6 g, 96.3 mmol) in water (40 mL) at 0° C. The reaction was warmed up to 25° C. and stirred for 16 h. After that, the reaction mixture was extracted with EA (2×20 mL). The aqueous phase was separated and acidified with cold conc. HCl until pH=2, which was extracted with EA (2×40 mL). The combined organic layer was dried over $Na_2SO_4$, filtered and concentrated to afford the titled compound (3.5 g, 89%) as a white solid. $^1$H NMR was performed at 400 MHz with $CDCl_3$ as solvent to characterize the titled compound, results are as follows: δ=5.16 (br. s., 1H), 4.24-4.08 (m, 2H), 4.07-3.93 (m, 2H), 1.41-1.14 (m, 3H).

Intermediate Compound 68": 4-hydroxybutyl 2-(ethoxycarbonylamino)acetate

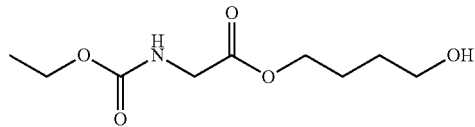

A mixture of 2-(ethoxycarbonylamino)acetic acid (1.0 g, 6.8 mmol), butane-1,4-diol (3.1 g, 34.0 mmol), DCC (1.7 g, 8.2 mmol) and DMAP (10 mg) in DCM (30 mL) was stirred at 25° C. for 16 h. After that, the reaction mixture was filtered and the filtrate was washed with water (2×20 mL). The combined organic layer was dried over $Na_2SO_4$, filtered and concentrated. The residue was purified by a silica gel flash column with PE/EA=5:1-2:1 to afford the titled compound (630 mg, 42%) as a colorless oil. $^1$H NMR was performed at 400 MHz with $CDCl_3$ as solvent to characterize the titled compound, results are as follows: δ=5.16 (br. s., 1H), 4.20 (t, J=6.6 Hz, 2H), 4.14 (t, J=7.2 Hz, 2H), 3.95 (d, J=5.2 Hz, 2H), 3.68 (t, J=6.2 Hz, 2H), 1.83-1.69 (m, 2H), 1.69-1.52 (m, 2H), 1.25 (t, J=7.2 Hz, 3H).

Compound 68:
4-(2-(ethoxycarbonyl)aminoacetoxy)butanoic Acid

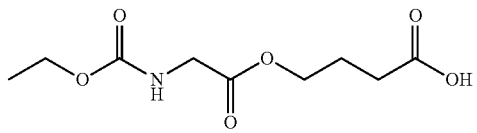 [SMILES: CCOC(=O)NCC(=O)OCCCC(=O)O]

Jones reagent was added in portions to a mixture of 4-hydroxybutyl 2-(ethoxycarbonylamino)acetate (500 mg, 2.3 mmol) and Celite® (diatomaceous earth, 1.5 g) in acetone (10 mL) at 0° C. The reaction proceeded at 0° C. over 30 min and the reaction progress was monitored by TLC. After completion, the reaction mixture was quenched by drops of isopropanol, diluted with EA (20 mL) and filtered. The filtered cake was washed with EA (10 mL), the combined filtrate was washed with brine (5 mL×2), dried over $Na_2SO_4$ and concentrated. The residue was purified by a silica gel flash column with DCM/EA=20:1-5:1 to afford the titled compound (190 mg, 36%) as a white solid. $^1$H NMR was performed at 400 MHz with $CDCl_3$ as solvent to characterize the titled compound, results are as follows: δ=5.20 (br. s., 1H), 4.23 (t, J=6.4 Hz, 2H), 4.14 (q, J=7.2 Hz, 2H), 3.96 (d, J=5.6 Hz, 2H), 2.46 (t, J=7.2 Hz, 2H), 2.04-1.97 (m, 2H), 1.25 (t, J=7.0 Hz, 3H).

Example 1-69

Intermediate Compound 69':
2-(isopropoxycarbonylamino)acetic Acid

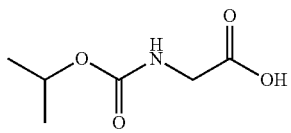

Isopropyl carbonochloridate (2.1 g, 17.3 mmol) was dropwise added to solution of glycine (1.0 g, 13.3 mmol) and $K_2CO_3$ (4.8 g, 34.6 mmol) in water (30 mL) at 0° C. The reaction was warmed up to 25° C. and stirred for 16 h. After that, the reaction mixture was extracted with EA (2×20 mL). The aqueous phase was separated and acidified with cold conc. HCl until pH=2, which was extracted with EA (2×30 mL). The combined organic layer was dried over $Na_2SO_4$, filtered and concentrated to afford the titled compound (2.0 g, 93%) as a white solid. $^1$H NMR was performed at 400 MHz with $CDCl_3$ as solvent to characterize the titled compound, results are as follows: δ=5.21 (br. s., 1H), 4.98-4.89 (m, 1H), 4.02-3.96 (m, 2H), 1.26-1.23 (m, 6H).

Intermediate Compound 69": 4-hydroxybutyl 2-(isopropoxycarbonylamino)acetate

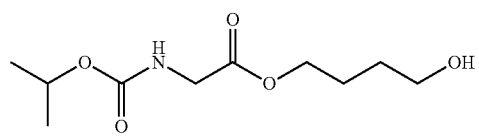 [SMILES: CC(C)OC(=O)NCC(=O)OCCCCO]

A mixture of 2-(isopropoxycarbonylamino)acetic acid (500 mg, 3.1 mmol), butane-1,4-diol (839 mg, 9.3 mmol), DCC (768 mg, 3.7 mmol) and DMAP (10 mg) in DCM (10 mL) was stirred at 25° C. for 16 h. After that, the reaction mixture was filtered and the filtrate was washed with water (2×20 mL). The combined organic layer was dried over $Na_2SO_4$, filtered and concentrated. The residue was purified by a silica gel flash column with PE/EA=10:1-1:1 to afford the titled compound (500 mg, 69%) as a colorless oil. $^1$H NMR was performed at 400 MHz with $CDCl_3$ as solvent to characterize the titled compound, results are as follows: δ=5.10 (br. s., 1H), 4.95-4.88 (m, 1H), 4.20 (t, J=6.4 Hz, 2H), 3.95 (d, J=5.6 Hz, 2H), 3.68 (t, J=6.2 Hz, 2H), 1.79-1.72 (m, 2H), 1.67-1.57 (m, 2H), 1.24 (d, J=6.4 Hz, 6H).

Compound 69:
4-(2-(isopropoxycarbonyl)aminoacetoxy)butanoic Acid

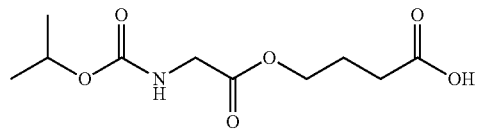 [SMILES: CC(C)OC(=O)NCC(=O)OCCCC(=O)O]

Jones reagent was added in portions to a mixture of 4-hydroxybutyl 2-(isopropoxycarbonylamino)acetate (500 mg, 2.1 mmol) and Celite® (diatomaceous earth, 1.5 g) in acetone (10 mL) at 0° C. The reaction proceeded at 0° C. over 30 min and the reaction progress was monitored by TLC. After completion, the reaction mixture was quenched by drops of isopropanol, diluted with EA (20 mL) and filtered. The filtered cake was washed with EA (10 mL), the combined filtrate was washed with brine (5 mL×2), dried over $Na_2SO_4$ and concentrated. The residue was purified by prep-HPLC to afford the titled compound (220 mg, 42%) as a white solid. $^1$H NMR was performed at 400 MHz with $CDCl_3$ as solvent to characterize the titled compound, results are as follows: δ=5.13 (br. s., 1H), 4.95-4.89 (m, 1H), 4.22 (t, J=6.2 Hz, 2H), 3.95 (d, J=5.6 Hz, 2H), 2.46 (t, J=7.2 Hz, 2H), 2.04-1.97 (m, 2H), 1.24 (d, J=6.4 Hz, 6H).

Scheme 7:

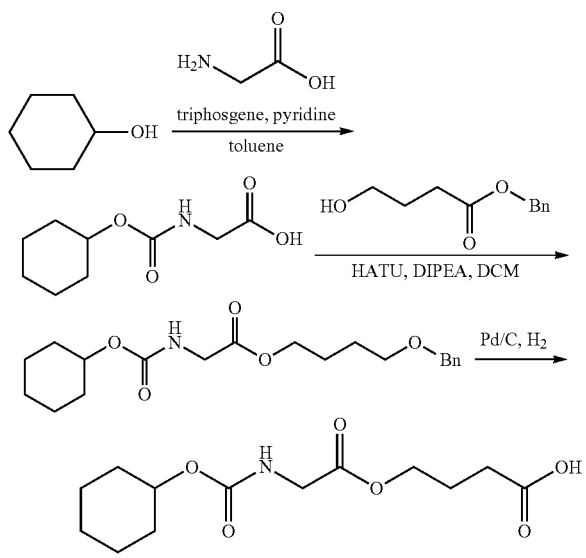

Example 1-70

Intermediate Compound 70':
2-((cyclohexyloxy)carbonylamino)acetic Acid

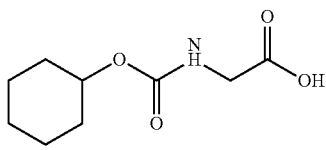 [SMILES: O=C(O)CNC(=O)OC1CCCCC1]

Pyridine (1.2 g, 15.0 mmol) was added dropwise to a solution of triphosgene (3.6 g, 12.0 mmol) in toluene (20 mL) at 0° C., and the formed yellow slurry was stirred for 0.5 h. After that, a solution of cyclohexanol (1.0 g, 10.0 mmol) in toluene (10 mL) was added dropwise at 0° C. The reaction was allowed to warm up and stirred at 25° C. for additional 1 h, then was quenched by the addition of water (30 mL). The resulting aqueous phase was extracted with EA (2×20 mL). The combined organic layer was dried over MgSO$_4$, filtered and concentrated. The residue was used directly for the next step without purification.

The above crude cyclohexyl carbonochloridate was added dropwise to solution of glycine (675 mg, 9.0 mmol) and K$_2$CO$_3$ (3.5 g, 25.0 mmol) in water (20 mL) at 0° C. The reaction was allowed to warm up and stirred at 25° C. for 16 h. After that, the reaction mixture was extracted with EA (2×30 mL). The aqueous phase was separated and acidified with cold conc. HCl until pH=2, which was extracted with EA (2×30 mL). The combined organic layer was dried over Na$_2$SO$_4$, filtered and concentrated to afford the titled compound (0.9 g, 45%) as a white solid. $^1$H NMR was performed at 400 MHz with CDCl$_3$ as solvent to characterize the titled compound, results are as follows: δ=5.14 (br. s., 1H), 4.79-4.59 (m, 1H), 4.07-3.92 (m, 2H), 1.95-1.80 (m, 2H), 1.73-1.70 (m, 2H), 1.61-1.14 (m, 6H).

Intermediate Compound 70": benzyl 4-(2-((cyclohexyloxy)carbonylamino)acetoxy)butanoate

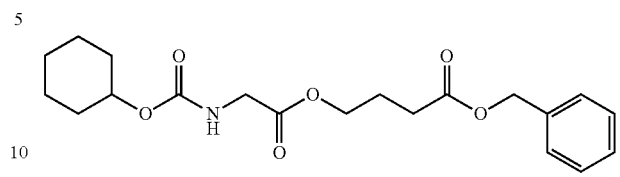

A solution of 2-((cyclohexyloxy)carbonylamino)acetic acid (850 mg, 4.2 mmol), benzyl 4-hydroxybutanoate (985 mg, 6.3 mmol), HATU (1.9 g, 5.1 mmol) and DIPEA (819 mg, 6.3 mmol) in DCM (20 mL) was stirred at 25° C. for 16 h. After that, the reaction mixture was diluted with DCM (10 mL) and washed with water (2×20 mL). The combined organic layer was dried over Na$_2$SO$_4$, filtered and concentrated. The residue was purified by a silica gel column with PE/EA=100:1-5:1 to afford the titled compound (0.9 g, 56%) as a colorless oil. $^1$H NMR was performed at 400 MHz with CDCl$_3$ as solvent to characterize the titled compound, results are as follows: S=7.42-7.29 (m, 5H), 5.12 (s, 2H), 5.08 (br. s., 1H), 4.77-4.55 (m, 1H), 4.20 (t, J=6.4 Hz, 2H), 3.93 (d, J=5.6 Hz, 2H), 2.45 (t, J=7.6 Hz, 2H), 2.04-1.97 (m, 2H), 1.87-1.85 (m, 2H), 1.78-1.64 (m, 2H), 1.58-1.46 (m, 1H), 1.46-1.14 (m, 5H).

Compound 70:
4-(2-(cyclohexyloxy)carbonylaminoacetoxy)butanoic Acid

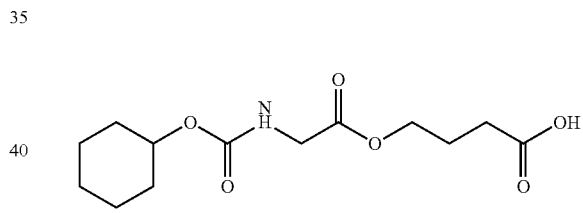

Pd/C (90 mg) was added to a solution of benzyl 4-(2-((cyclohexyloxy)carbonylamino)acetoxy)butanoate (900 mg, 2.4 mmol) in EA (10 mL). The reaction was stirred under H$_2$ atmosphere at 25° C. for 16 h. After that, the reaction mixture was filtered and the filtrate was concentrated. The residue was purified by a silica gel flash column with PE/EA=10:1-1:1 to afford the titled compound (220 mg, 32%) as a white solid. $^1$H NMR was performed at 400 MHz with CDCl$_3$ as solvent to characterize the titled compound, results are as follows: δ=5.13 (br. s., 1H), 4.67-4.62 (m, 1H), 4.23 (t, J=6.2 Hz, 2H), 3.95 (d, J=6.0 Hz, 2H), 2.46 (t, J=7.2 Hz, 2H), 2.05-1.98 (m, 2H), 1.88-1.86 (m, 2H), 1.72-1.70 (m, 2H), 1.59-1.47 (m, 1H), 1.46-1.12 (m, 5H).

Scheme 8:

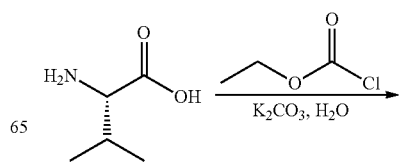

-continued

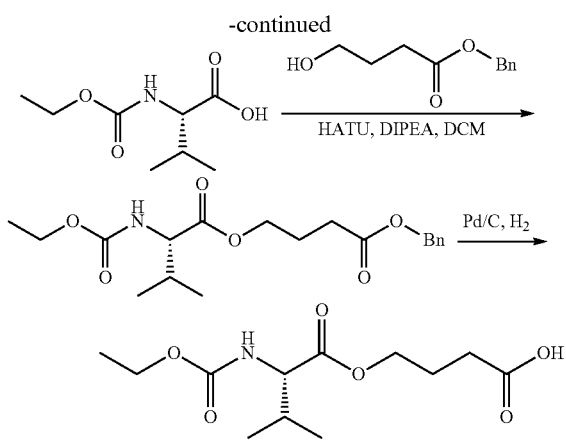

Example 1-71

Intermediate Compound 71':
(S)-2-(ethoxycarbonylamino)-3-methylbutanoic Acid

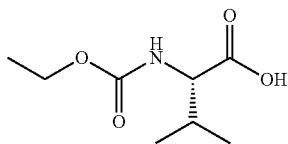

Ethyl carbonochloridate (1.9 g, 17.3 mmol) was added dropwise to a solution of L-valine (1.0 g, 8.5 mmol) and $K_2CO_3$ (4.8 g, 34.6 mmol) in water (30 mL) at 0° C. The reaction was allowed to warm up and stirred at 25° C. for 16 h. After that, the reaction mixture was extracted with EA (2×20 mL). The aqueous phase was separated and acidified with cold conc. HCl until pH=2, which was extracted with EA (2×30 mL). The combined organic layer was dried over $Na_2SO_4$, filtered and concentrated to afford the titled compound (1.5 g, 60%) as a colorless oil. $^1$H NMR was performed at 400 MHz with $CDCl_3$ as solvent to characterize the titled compound, results are as follows: δ=5.12 (d, J=9.2 Hz, 1H), 4.33 (dd, J=4.6, 9.0 Hz, 1H), 4.14 (q, J=7.2 Hz, 2H), 2.32-2.11 (m, 1H), 1.26 (t, J=7.2 Hz, 3H), 1.01 (d, J=6.4 Hz, 3H), 0.94 (d, J=7.2 Hz, 3H).

Intermediate Compound 71'': (S)-4-(benzyloxy)-4-oxobutyl 2-(ethoxycarbonylamino)-3-methylbutanoate

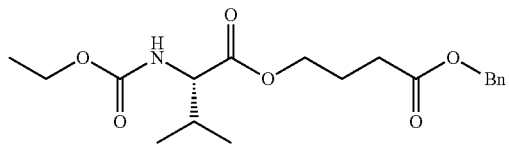 [SMILES: CCOC(=O)N[C@H](C(=O)OCCCC(=O)OCc1ccccc1)C(C)C]

A solution of (S)-2-(ethoxycarbonylamino)-3-methylbutanoic acid (536 mg, 2.8 mmol), benzyl 4-hydroxybutanoate (500 mg, 2.6 mmol), HATU (1.2 g, 3.1 mmol) and DIPEA (499 mg, 3.9 mmol) in DCM (20 mL) was stirred at 25° C. for 16 h. After that, the reaction mixture was diluted with DCM (10 mL) and washed with water (2×20 mL). The organic layer was dried over $Na_2SO_4$, filtered and concentrated. The residue was purified by silica gel flash column with PE/EA=20:1-5:1 to afford the titled compound (370 mg, 39%) as a colorless oil. $^1$H NMR was performed at 400 MHz with $CDCl_3$ as solvent to characterize the titled compound, results are as follows: δ=7.45-7.46 (m, 5H), 5.13 (s, 2H), 4.26 (dd, J=4.8, 8.8 Hz, 1H), 4.17 (t, J=6.4 Hz, 2H), 4.11 (q, J=7.2 Hz, 2H), 2.46 (t, J=7.6 Hz, 2H), 2.21-2.07 (m, 1H), 204-1.97 (m, 2H), 1.24 (t, J=7.0 Hz, 3H), 096 (d, J=6.8 Hz, 3H), 0.87 (d, J=6.8 Hz, 3H).

Compound 71: (S)-4-(2-((ethoxycarbonyl)amino)-3-methylbutanoyloxy)butanoic Acid

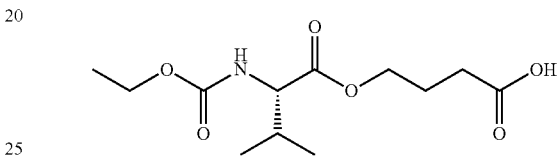

Pd/C (40 mg) was added to a solution of (S)-4-(benzyloxy)-4-oxobutyl 2-(ethoxycarbonylamino)-3-methylbutanoate (350 mg, 1.0 mmol) in EA (10 mL). The reaction was stirred under $H_2$ atmosphere at 25° C. for 16 h. The reaction was filtered and the filtrate was concentrated to afford the titled compound (240 mg, 91%) as a colorless oil. $^1$H NMR was performed at 400 MHz with $CDCl_3$ as solvent to characterize the titled compound, results are as follows: δ=5.16 (d, J=8.8 Hz, 1H), 4.28-4.10 (m, 5H), 2.46 (t, J=7.2 Hz, 2H), 2.25-2.08 (m, 1H), 2.05-1.96 (m, 2H), 1.25 (t, J=7.0 Hz, 3H), 0.93 (dd, J=7.0, 31.4 Hz, 6H).

Scheme 9:

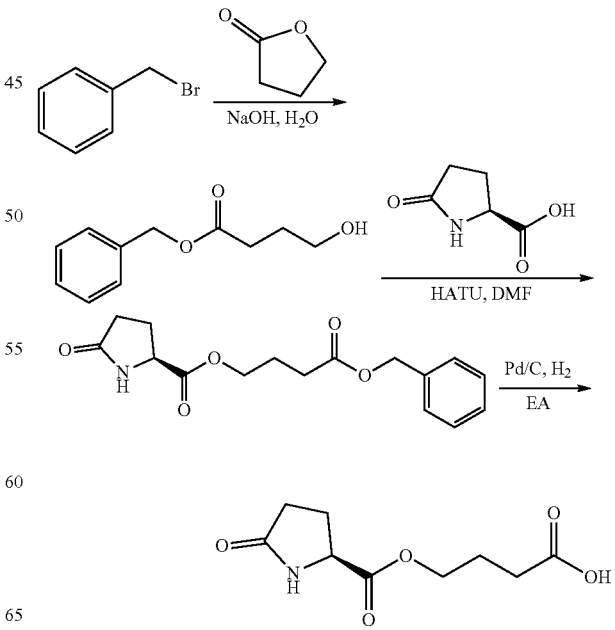

Example 1-72

Intermediate Compound 72': benzyl 4-hydroxybutanoate

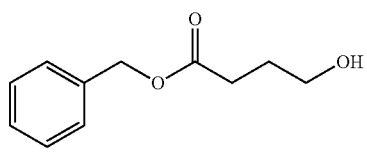 [SMILES: O=C(CCCO)OCc1ccccc1]

A mixture of dihydrofuran-2(3H)-one (5.1 g, 59.2 mmol) and NaOH (2.37 g, 59.2 mmol) in H$_2$O (60 mL) was heated under 100° C. for 1 h. The clear solution was then cooled and concentrated. The resultant solid was suspended in toluene and concentrated to remove H$_2$O. The resultant solid was suspended in acetone (60 mL), to which TBAF (772 mg, 2.96 mmol) and (bromomethyl)benzene (12.2 g, 71.1 mmol) was added. The reaction was heated under reflux for 3 h. After that, the reaction mixture was partitioned between EA (150 mL) and H$_2$O (100 mL). The organic layer was separated, dried over Na$_2$SO$_4$ and concentrated. The residue was purified by a silica gel flash column with Hex/EA=2:1-1:2 to afford the titled compound (8.5 g, 74%) as a colorless oil. $^1$H NMR was performed at 400 MHz with CDCl$_3$ as solvent to characterize the titled compound, results are as follows: δ=7.37-7.34 (m, 5H), 5.13 (s, 2H), 3.68 (t, J=6.2 Hz, 2H), 2.50 (t, J=7.2 Hz, 2H), 1.94-1.87 (m, 2H).

Intermediate Compound 72": (S)-4-(benzyloxy)-4-oxobutyl 5-oxopyrrolidine-2-carboxylate

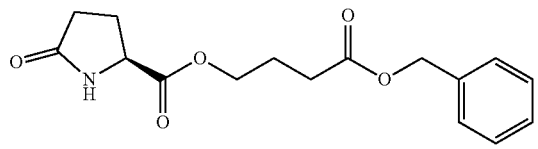 [SMILES: O=C1CC[C@@H](C(=O)OCCCC(=O)OCc2ccccc2)N1]

HATU (2.9 g, 7.7 mmol) and DIPEA (998 mg, 7.7 mmol) was added to a solution of L-pyroglutamic acid (731 mg, 5.7 mmol) and benzyl 4-hydroxybutanoate (1.0 g, 5.1 mmol) in DMF (20 mL). The mixture was stirred at 25° C. for 16 h. The reaction was concentrated and the residue was purified by prep-HPLC to afford the titled compound (0.9 g, 57%) as a colorless oil. $^1$H NMR was performed at 400 MHz with CDCl$_3$ as solvent to characterize the titled compound, results are as follows: δ=7.39-7.33 (m, 5H), 6.34 (br. s., 1H), 5.13 (s, 2H), 4.21 (t, J=6.0 Hz, 3H), 2.53-2.28 (m, 5H), 2.27-2.13 (m, 1H), 2.09-1.96 (m, 2H).

Compound 72: (S)-4-(5-oxopyrrolidine-2-carbonyloxy)butanoic Acid

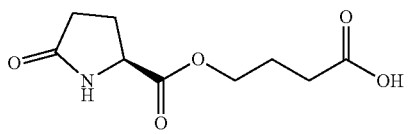 [SMILES: O=C(O)CCCOC(=O)[C@@H]1CCC(=O)N1]

Pd/C (90 mg) was added to a solution of (S)-4-(benzyloxy)-4-oxobutyl 5-oxopyrrolidine-2-carboxylate (900 mg, 3.0 mmol) in EA (20 mL). The reaction was stirred under H$_2$ atmosphere at 25° C. for 16 h. After that, the reaction mixture was filtered and the filtrate was concentrated to afford the titled compound (580 mg, 91%) as a white solid. $^1$H NMR was performed at 400 MHz with CDCl$_3$ as solvent to characterize the titled compound, results are as follows: δ=7.98 (br. s., 1H), 4.31-4.16 (m, 3H), 2.52-2.39 (m, 5H), 2.35-2.19 (m, 1H), 2.06-1.94 (m, 2H).

Scheme 10:

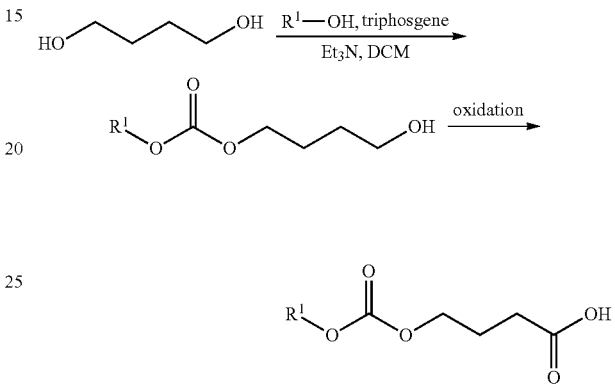

Example 1-73

Intermediate Compound 73': 4-hydroxybutyl (2-methoxyphenyl)carbonate

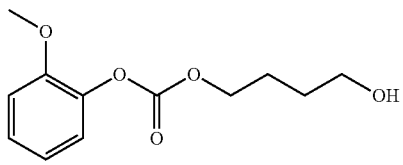 [SMILES: COc1ccccc1OC(=O)OCCCCO]

A solution of 2-methoxyphenol (1 g, 8.06 mmol) and Et$_3$N (977 mg, 9.68 mmol) in DCM (10 mL) was added dropwise to a stirred solution of triphosgene (788 mg, 2.66 mmol) in DCM (10 mL) at 0° C. during 10 min. After that, the reaction was allowed to warm up gradually and stirred at 25° C. for 2 h. The above reaction solution was added dropwise to a stirred solution of butane-1,4-diol (2.18 g, 24.19 mmol) in DCM (10 mL) at 0° C. during 10 min, and then the reaction mixture was stirred at 25° C. for 14 h. After that, the reaction mixture was diluted with water (10 mL), separated and the organic phase was washed with brine (10 mL), dried over Na$_2$SO$_4$ and concentrated. The residue was purified by a silica gel flash column with DCM/EA=10:1 to afford the titled compound (350 mg, 27%) as a colorless oil. $^1$H NMR was performed at 400 MHz with CDCl$_3$ as solvent to characterize the titled compound, results are as follows: δ=7.22 (t, J=8.0 Hz, 1H), 7.13 (d, J=6.8 Hz, 1H), 6.99-6.93 (m, 2H), 4.30 (t, J=6.4 Hz, 2H), 3.86 (s, 3H), 3.72 (t, J=6.2 Hz, 2H), 1.89-1.82 (m, 2H), 1.75-1.68 (m, 2H).

Compound 73:
4-((2-methoxyphenoxy)carbonyloxy)butanoic Acid

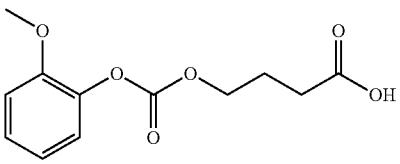 [SMILES: COc1ccccc1OC(=O)OCCCC(=O)O]

Jones reagent was added dropwise to a stirred mixture of 4-hydroxybutyl (2-methoxyphenyl) carbonate (350 mg, 1.46 mmol) and Celite® (diatomaceous earth, 700 mg) in acetone (5 mL) at 0° C. The reaction proceeded at 0° C. over 1 h and the reaction progress was monitored by TLC. After completion, the reaction was quenched with drops of isopropanol, diluted with EA (15 mL), and then filtered. The filtered cake was washed with EA (5 mL) and the combined filtrate was washed with brine (5 mL×2), dried over $Na_2SO_4$ and concentrated. The residue was purified by a silica gel flash column with DCM/EA=10:1 to afford the titled compound (180 mg, 49%) as crystalline solids. $^1$H NMR was performed at 400 MHz with $CDCl_3$ as solvent to characterize the titled compound, results are as follows: δ=7.22 (t, J=8.0 Hz, 1H), 7.13 (d, J=6.8 Hz, 1H), 6.99-6.93 (m, 2H), 4.33 (t, J=6.2 Hz, 2H), 3.86 (s, 3H), 2.55 (t, J=7.4 Hz, 2H), 2.12-2.05 (m, 2H).

Example 1-74

Intermediate Compound 74': 4-hydroxybutyl (2-isopropyl-5-methylphenyl) carbonate

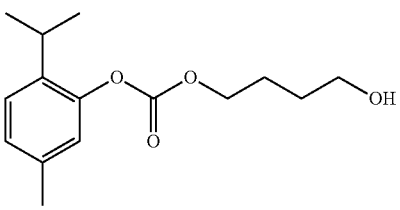 [SMILES: Cc1ccc(C(C)C)c(OC(=O)OCCCCO)c1]

A solution of 2-isopropyl-5-methylphenol (1 g, 6.67 mmol) and $Et_3N$ (741 mg, 7.33 mmol) in DCM (10 mL) was added dropwise to a stirred solution of triphosgene (651 mg, 2.20 mmol) in DCM (10 mL) at 0° C. during 10 min. After that, the reaction was allowed to warm up gradually and stirred at 0-25° C. for 2 h. The above reaction solution was dropwise added to a stirred solution of butane-1,4-diol (1.8 g, 20 mmol) in DCM (10 mL) at 0° C. during 10 min, and then the reaction mixture was stirred at 0-25° C. for 14 h. After that, the reaction mixture was diluted with water (10 mL), separated and the organic phase was washed with brine (10 mL), dried over $Na_2SO_4$ and concentrated. The residue was purified by a silica gel flash column with Hex/EA=3:1 to afford the titled compound (900 mg, 51%) as a colorless oil. $^1$H NMR was performed at 400 MHz with $CDCl_3$ as solvent to characterize the titled compound, results are as follows: δ=7.19 (d, J=8.0 Hz, 1H), 7.04 (d, J=7.8 Hz, 1H), 6.90 (s, 1H), 4.30 (t, J=6.4 Hz, 2H), 3.72 (t, J=6.2 Hz, 2H), 3.10-3.03 (m, 1H), 2.32 (s, 3H), 1.89-1.82 (m, 2H), 1.75-1.68 (m, 2H), 1.20 (d, J=7.2 Hz, 6H).

Compound 74: 4-((2-isopropyl-1-methylphenoxy)carbonyloxy)butanoic Acid

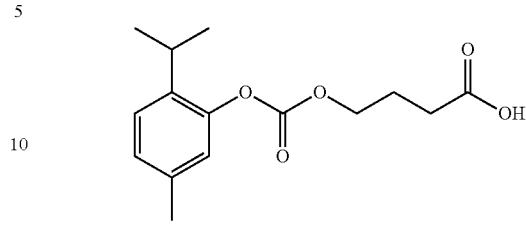

Jones reagent was added dropwise to a stirred mixture of 4-hydroxybutyl (2-isopropyl-5-methylphenyl) carbonate (900 mg, 3.38 mmol) and Celite® (diatomaceous earth, 1.8 g) in acetone (10 mL) at 0° C. The reaction proceeded at 0° C. over 1 h and the reaction progress was monitored by TLC. After completion, the reaction was quenched with drops of isopropanol, diluted with EA (30 mL), and then filtered. The filtered cake was washed with EA (10 mL) and the combined filtrate was washed with brine (10 mL×2), dried over $Na_2SO_4$ and concentrated. The residue was purified by a silica gel flash column with DCM/EA=8:1 to afford the titled compound (500 mg, 53%) as a colorless oil. $^1$H NMR was performed at 400 MHz with $CDCl_3$ as solvent to characterize the titled compound, results are as follows: δ=7.19 (d, J=8.0 Hz, 1H), 7.04 (d, J=7.8 Hz, 1H), 6.90 (s, 1H), 4.32 (t, J=6.2 Hz, 2H), 3.09-3.02 (m, 1H), 2.55 (t, J=7.2 Hz, 2H), 2.32 (s, 3H), 2.13-2.06 (m, 2H), 1.20 (d, J=6.8 Hz, 6H).

Example 1-75

Intermediate Compound 75': benzo[d][1,3]dioxol-5-yl (4-hydroxybutyl) carbonate

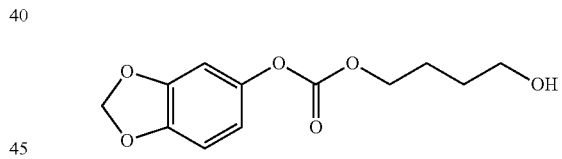

A solution of benzo[d][1,3]dioxol-5-ol (1 g, 7.25 mmol) and $Et_3N$ (878 mg, 8.70 mmol) in DCM (10 mL) was added dropwise to a stirred solution of triphosgene (708 mg, 2.39 mmol) in DCM (10 mL) at 0° C. during 10 min. After that, the reaction was allowed to warm up gradually and stirred at 0-25° C. for 2 h. The above reaction solution was dropwise added to a stirred solution of butane-1,4-diol (1.96 g, 21.74 mmol) in DCM (10 mL) at 0° C. during 10 min, and then the reaction mixture was stirred at 0-25° C. for 14 h. After that, the reaction mixture was diluted with water (10 mL), separated and the organic phase was washed with brine (10 mL), dried over $Na_2SO_4$ and concentrated, the residue was purified by a silica gel flash column with DCM/EA=10:1 to afford the titled compound (500 mg, 27%) as a yellow oil. $^1$H NMR was performed at 400 MHz with $CDCl_3$ as solvent to characterize the titled compound, results are as follows: δ=6.75 (d, J=8.4 Hz, 1H), 6.67 (d, J=2.0 Hz, 1H), 6.60 (dd, J=2.0, 8.4 Hz, 1H), 5.97 (s, 2H), 4.26 (t, J=6.6 Hz, 2H), 3.68 (t, J=6.2 Hz, 2H), 1.85-1.78 (m, 2H), 1.71-1.64 (m, 2H).

Compound 75: 4-((benzo[d][1,3]dioxol-5-yloxy)carbonyloxy)butanoic Acid

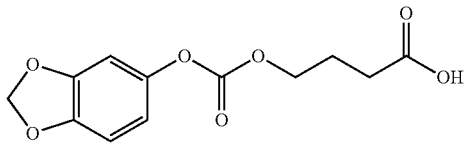 [SMILES: O=C(O)CCCOC(=O)Oc1ccc2c(c1)OCO2]

Jones reagent was added dropwise to a stirred mixture of benzo[d][1,3]dioxol-5-yl (4-hydroxybutyl) carbonate (500 mg, 1.97 mmol) and Celite® (diatomaceous earth, 1 g) in acetone (10 mL) at 0° C. The reaction proceeded at 0° C. over 1 h and the reaction progress was monitored by TLC. After completion, the reaction was quenched with drops of isopropanol, diluted with EA (30 mL), and then filtered. The filtered cake was washed with EA (10 mL) and the combined filtrate was washed with brine (10 mL×2), dried over $Na_2SO_4$ and concentrated. The residue was purified by a silica gel flash column with DCM/EA=8:1 to afford the titled compound (300 mg, 57%) as brown solid. $^1H$ NMR was performed at 400 MHz with $CDCl_3$ as solvent to characterize the titled compound, results are as follows: δ=6.77 (d, J=8.4 Hz, 1H), 6.69 (d, J=1.6 Hz, 1H), 6.62 (dd, J=2.0, 8.4 Hz, 1H), 5.99 (s, 2H), 4.30 (t, J=6.2 Hz, 2H), 2.54 (t, J=7.2 Hz, 2H), 2.11-2.05 (m, 2H).

Example 1-76

Intermediate Compound 76': 4-methylbenzyl carbonochloridate

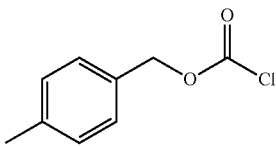

Pyridine (4.86 g, 61.48 mmol) was added to a stirred solution of triphosgene (14.5 g, 49.18 mmol) in toluene (100 mL) at 0° C. and the mixture was stirred for 30 min. After that, a solution of p-tolylmethanol (5 g, 40.98 mmol) in toluene (50 mL) was dropwise added during 30 min, and then the reaction proceeded at 0° C. for additional 1 h. The reaction mixture was partitioned between water (50 mL) and EA (100 mL), the organic phase was separated and dried over $MgSO_4$, filtered and concentrated. The residue was purified by a silica gel flash column with PE/EA=10:1 to afford the titled compound (6 g, 79%) as a colorless oil.

Intermediate Compound 76": 4-hydroxybutyl 4-methylbenzyl carbonate

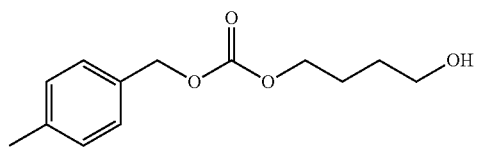 [SMILES: Cc1ccc(COC(=O)OCCCCO)cc1]

4-methylbenzyl carbonochloridate (3 g, 16.30 mmol) in DCM (20 mL) was dropwise added to a stirred solution of $Et_3N$ (5 g, 49.50 mmol) and butane-1,4-diol (4.4 g, 48.89 mmol) in DCM (40 mL) at 0° C. during 15 min. The reaction was stirred at 25° C. for 16 h. After that, the reaction mixture was diluted with water (30 mL) and the aqueous phase was separated. The resulting organic phase was washed with brine (15 mL), dried over $Na_2SO_4$ and concentrated, the residue was purified by a silica gel flash column with PE/EA=3:1 to afford the titled compound (700 mg, 18%) as a colorless oil. $^1H$ NMR was performed at 400 MHz with $CDCl_3$ as solvent to characterize the titled compound, results are as follows: δ=7.28 (d, J=8.0 Hz, 2H), 7.17 (d, J=7.6 Hz, 2H), 5.11 (s, 2H), 4.18 (t, J=6.4 Hz, 2H), 3.67 (t, J=6.4 Hz, 2H), 2.35 (s, 3H), 1.80-1.73 (m, 2H), 1.68-1.61 (m, 2H).

Compound 76: 4-((4-methylbenzyl)oxycarbonyloxy)butanoic Acid

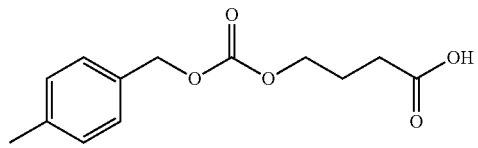 [SMILES: Cc1ccc(COC(=O)OCCCC(=O)O)cc1]

Jones reagent was added dropwise to a stirred mixture of 4-hydroxybutyl 4-methylbenzyl carbonate (700 mg, 2.94 mmol) and Celite® (diatomaceous earth, 1.4 g) in acetone (10 mL) at 0° C. The reaction proceeded at 0° C. over 1 h and the reaction progress was monitored by TLC. After completion, the reaction was quenched with drops of isopropanol, diluted with EA (20 mL), and then filtered. The filtered cake was washed with EA (10 mL) and the combined filtrate was washed with brine (10 mL×2), dried over $Na_2SO_4$ and concentrated. The residue was purified by a silica gel flash column with PE/EA=2:1 to afford the titled compound (400 mg, 54%) as crystalline solids. $^1H$ NMR was performed at 400 MHz with $CDCl_3$ as solvent to characterize the titled compound, results are as follows: δ=7.28 (d, J=8.0 Hz, 2H), 7.17 (d, J=8.0 Hz, 2H), 5.11 (s, 2H), 4.20 (t, J=6.4 Hz, 2H), 2.47 (t, J=7.2 Hz, 2H), 2.35 (s, 3H), 2.03-1.96 (m, 2H).

Example 1-77

Intermediate Compound 77': 4-hydroxybutyl (tetrahydro-2H-pyran-4-yl) carbonate

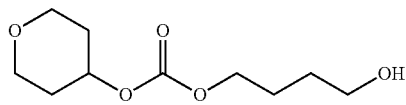 [SMILES: O=C(OCCCCO)OC1CCOCC1]

A solution of tetrahydro-2H-pyran-4-ol (1.0 g, 9.8 mmol) and $Et_3N$ (1.2 g, 11.8 mmol) in DCM (10 mL) was added dropwise to solution of triphosgene (1.0 g, 3.2 mmol) in DCM (10 mL) at 0° C. After the addition is complete, the reaction was stirred at 0° C. for 1 h. After that, the above slurry was added dropwise to the suspension of butane-1,4-diol (2.7 g, 29.4 mmol) in DCM (10 mL) at 0° C. The resulting mixture was warmed up gradually to 25° C. and stirred for 16 h. The reaction was quenched by water (10 mL) and separated. The organic phase was dried over Na$_2$SO$_4$, filtered and concentrated. The residue was purified by a silica gel flash column with PE/EA=10:1-1:1 to afford the titled compound (380 mg, 18%) as a colorless oil. $^1$H NMR was performed at 400 MHz with CDCl$_3$ as solvent to characterize the titled compound, results are as follows: δ=4.82-4.78 (m, 1H), 4.18 (t, J=6.4 Hz, 2H), 3.97-3.92 (m, 2H), 3.69 (t, J=6.2 Hz, 2H), 3.70-3.53 (m, 2H), 2.06-1.93 (m, 2H), 1.87-1.59 (m, 6H).

Compound 77: 4-((tetrahydro-2H-pyran-4-yl)oxy-carbonyloxy)butanoic Acid

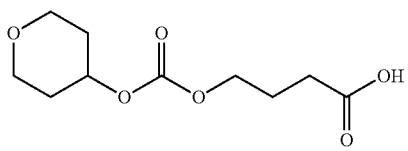 [SMILES: O=C(O)CCCOC(=O)OC1CCOCC1]

Jones reagent was added dropwise to a stirred mixture of 4-hydroxybutyl (tetrahydro-2H-pyran-4-yl) carbonate (300 mg, 1.4 mmol) and Celite® (diatomaceous earth, 0.6 g) in acetone (6 mL). The reaction proceeded at 0° C. over 1 h and the reaction progress was monitored by TLC. After completion, the reaction was quenched with drops of isopropanol, diluted with EA (20 mL), and then filtered. The filtered cake was washed with EA (20 mL) and the combined filtrate was washed with brine (10 mL×2), dried over Na$_2$SO$_4$ and concentrated. The residue was purified by a silica gel flash column with PE/EA=50:1-5:1 to afford the titled compound (110 mg, 34%) as crystalline solids. $^1$H NMR was performed at 400 MHz with CDCl$_1$ as solvent to characterize the titled compound, results are as follows: δ=4.84-4.77 (m, 1H), 4.20 (t, J=6.4 Hz, 2H), 4.03-3.86 (m, 2H), 3.64-3.44 (m, 2H), 2.50 (t, J=7.6 Hz, 2H), 2.05-1.88 (m, 4H), 1.79-1.70 (m, 2H).

Scheme 11:

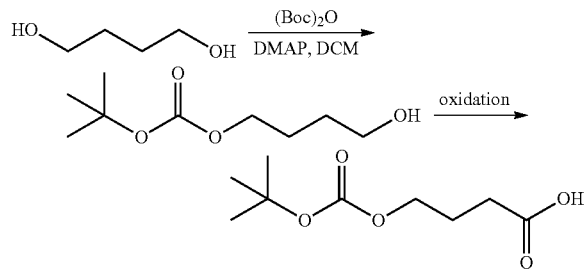

Example 1-78

Intermediate Compound 78': tert-butyl (4-hydroxybutyl) carbonate

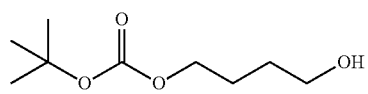

(Boc)$_2$O (2.05 g, 9.4 mmol) and DMAP (100 mg) was added to a stirred solution of butane-1,4-diol (10 g, 111.11 mmol) in DCM (100 mL). The reaction was stirred at 25° C. for 16 h. After that, the reaction mixture was diluted with saturated aqueous NH$_4$Cl (20 mL) and stirred for 5 min. The aqueous phase was separated and extracted with DCM (20 mL). The combined organic phase was washed with saturated brine (30 mL), dried over anhydrous Na$_2$SO$_4$ and evaporated. The residue was purified by a silica gel flash column with Hex/EA=10:1 to yield the titled compound (1 g, 56%) as a colorless oil. $^1$H NMR was performed at 400 MHz with CDCl$_3$ as solvent to characterize the titled compound, results are as follows: δ=4.10 (t, J=6.6 Hz, 2H), 3.68 (q, J=6.0 Hz, 2H), 1.79-1.72 (m, 2H), 1.69-1.62 (m, 2H), 1.48 (s, 9H), 1.34 (t, J=5.2 Hz, 1H).

Compound 78: 4-(tert-butoxycarbonyloxy)butanoic Acid

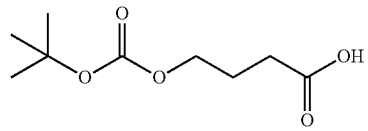

Jones reagent was added in portions to a stirred mixture of tert-butyl (4-hydroxybutyl) carbonate (800 mg, 4.21 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-6:1 to yield the titled compound (500 mg, 58%) as a colorless oil. $^1$H NMR was performed at 400 MHz with CDCl$_3$ as solvent to characterize the titled compound, results are as follows: δ=4.12 (t, J=6.2 Hz, 2H), 2.49 (t, J=7.4 Hz, 2H), 2.03-1.96 (m, 2H), 1.48 (s, 9H).

Scheme 12:

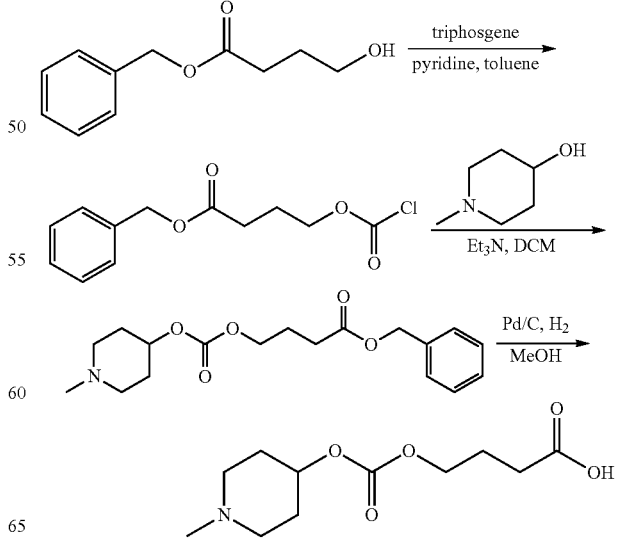

Example 1-79

Intermediate Compound 79': benzyl 4-(chlorocarbonyloxy)butanoate

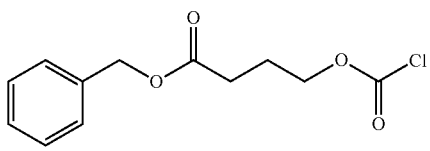 [SMILES: O=C(Cl)OCCCC(=O)OCc1ccccc1]

Pyridine (305 mg, 3.9 mmol) was slowly added to a solution of triphosgene (976 mg, 3.4 mmol) in toluene (10 mL) at 0° C. and stirred for 0.5 h. A solution of benzyl 4-hydroxybutanoate (500 mg, 2.6 mmol) in toluene (5 mL) was added to the above formed slurry at 0° C. The reaction was allowed to warm up and stirred at 25° C. for 1.5 h. After that, the reaction mixture was partitioned between water (15 mL) and EA (15 mL). The organic layer was separated, washed with brine (10 mL), dried over $Na_2SO_4$ and filtered. The filtrated was concentrated to yield a light yellow oil, which was purified by a silica gel flash column with PE/EA=20:1-5:1 to afford the titled compound (490 mg, 74%) as colorless oil. $^1$H NMR was performed at 400 MHz with $CDCl_3$ as solvent to characterize the titled compound, results are as follows: δ=7.43-7.27 (m, 5H), 5.14 (s, 2H), 4.37 (t, J=6.2 Hz, 2H), 2.50 (t, J=7.2 Hz, 2H), 2.12-2.05 (m, 2H).

Intermediate Compound 79'': benzyl 4-((1-methylpiperidin-4-yl)oxycarbonyl oxy)butanoate

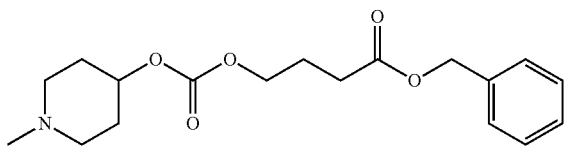 [SMILES: CN1CCC(OC(=O)OCCCC(=O)OCc2ccccc2)CC1]

A solution of benzyl 4-(chlorocarbonyloxy)butanoate (500 mg, 1.95 mmol) and $Et_3N$ (395 mg, 3.91 mmol) in DCM (5 mL) was added dropwise to a stirred solution of 1-methylpiperidin-4-ol (225 mg, 1.96 mmol) in DCM (5 mL) at 0° C. during 10 min. After that, the reaction mixture was diluted with water (5 mL), the resulting aqueous phase was separated and extracted with DCM (5 mL). The combined organic phase was washed with brine (5 mL), dried over $Na_2SO_4$, filtered and concentrated. The residue was purified by prep-HPLC to afford the titled compound (240 mg, 37%) as a colorless oil. $^1$H NMR was performed at 400 MHz with $CDCl_3$ as solvent to characterize the titled compound, results are as follows: S=7.43-7.29 (m, 5H), 5.12 (s, 2H), 4.77 (br. s., 1H), 4.18 (t, J=6.2 Hz, 2H), 2.84-2.65 (m, 4H), 2.51-2.47 (m, 5H), 2.18-1.99 (m, 4H), 1.98-1.83 (m, 2H).

Compound 79: 4-((1-methylpiperidin-4-yl)oxycarbonyloxy)butanoic Acid

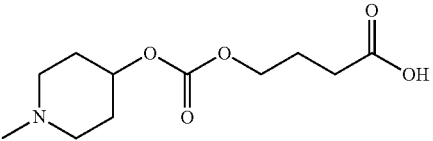 [SMILES: CN1CCC(OC(=O)OCCCC(=O)O)CC1]

Pd/C (40 mg) was added to a solution of benzyl 4-((1-methylpiperidin-4-yl)oxycarbonyloxy)butanoate (200 mg, 0.6 mmol) in methanol (3 mL). The mixture was stirred at 25° C. under $H_2$ atmosphere for 16 h. After that, the mixture was filtered through Celite® (diatomaceous earth) and the filtered cake was washed with methanol (3 mL). The combined filtrate was concentrated, the residue was purified by prep-HPLC to afford the titled compound (15 mg, 10%) as crystalline solids. $^1$H NMR was performed at 400 MHz with $CDCl_3$ as solvent to characterize the titled compound, results are as follows: δ=4.92 (br. s., 1H), 4.22 (t, J=6.4 Hz, 2H), 3.19 (br. s., 4H), 2.77 (s, 3H), 2.44 (t, J=7.2 Hz, 2H), 2.35-2.20 (m, 2H), 2.13-2.08 (m, 2H), 2.05-1.98 (m, 2H).

Scheme 13:

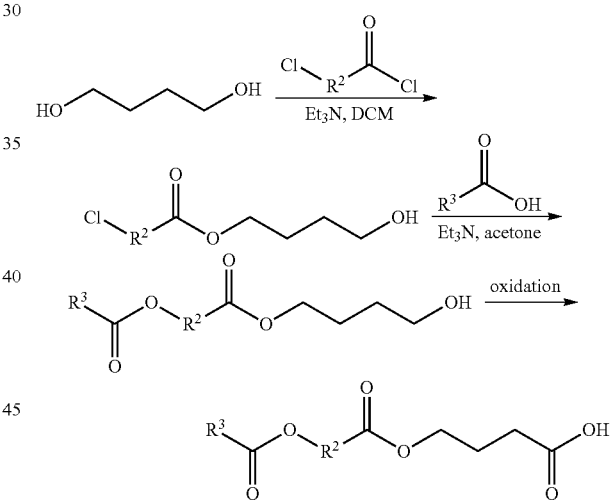

Example 1-80

Intermediate Compound 80': 4-hydroxybutyl 2-chloroacetate

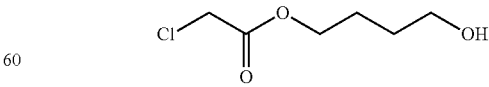

A solution of 2-chloroacetyl chloride (5 g, 44.25 mmol) in DCM (10 mL) dropwise during 10 min was added to a stirred solution of butane-1,4-diol (19.9 g, 221.11 mmol) and $Et_3N$ (8.9 g, 88.5 mmol) in DCM (40 mL) at 0° C. The reaction was allowed to warm up gradually and stirred at 0-25° C. over 16 h. After that, the reaction mixture was diluted with H$_2$O (20 mL) and stirred for 5 min. The aqueous phase was separated and extracted with DCM (20 mL). The combined organic phase was washed with saturated brine (30 mL), dried over anhydrous Na$_2$SO$_4$ and evaporated. The residue was purified by a silica gel flash column with Hex/EA=5:1 to yield the titled compound (3.2 g, 44%) as a colorless oil. $^1$H NMR was performed at 400 MHz with CDCl$_3$ as solvent to characterize the titled compound, results are as follows: δ=4.24 (t, J=6.6 Hz, 2H), 4.07 (s, 2H), 3.69 (t, J=6.4 Hz, 2H), 1.82-1.75 (m, 2H), 1.68-1.61 (m, 2H).

Intermediate Compound 80":
2-(4-hydroxybutoxy)-2-oxoethyl 2-ethylbenzoate

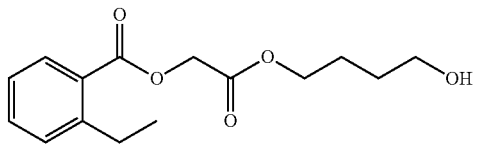 [SMILES: CCc1ccccc1C(=O)OCC(=O)OCCCCO]

Et$_3$N (365 mg, 3.61 mmol) and 4-hydroxybutyl 2-chloroacetate (300 mg, 1.81 mmol) was added to a stirred solution of 2-ethylbenzoic acid (542 mg, 3.61 mmol) in acetone (10 mL). The reaction was stirred at 50° C. for 5 h. After that, the reaction mixture was partitioned between DCM (20 mL) and H$_2$O (10 mL). The aqueous phase was separated and extracted with DCM (10 mL). The combined organic phase was washed with saturated brine (20 mL), dried over anhydrous Na$_2$SO$_4$ and evaporated. The residue was purified by a silica gel flash column with Hex/EA=6:1 to yield the titled compound (175 mg, 35%) as a colorless oil. $^1$H NMR was performed at 400 MHz with CDCl$_3$ as solvent to characterize the titled compound, results are as follows: δ=8.02-7.95 (m, 1H), 7.49-7.44 (m, 1H), 7.32-7.24 (m, 2H), 4.83 (s, 2H), 4.25 (t, J=6.4 Hz, 2H), 3.67 (t, J=6.4 Hz, 2H), 3.08-2.97 (m, 2H), 1.81-1.74 (m, 2H), 1.67-1.60 (m, 2H), 1.28-1.22 (m, 3H).

Compound 80:
4-(2-(2-ethylbenzoyloxy)acetoxy)butanoic Acid

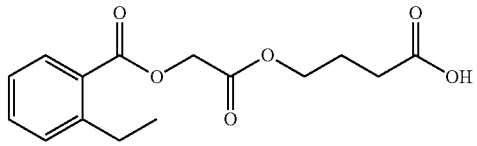 [SMILES: CCc1ccccc1C(=O)OCC(=O)OCCCC(=O)O]

Jones reagent was added in portions to a stirred mixture of 2-(4-hydroxybutoxy)-2-oxoethyl 2-ethylbenzoate (170 mg, 0.61 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (90 mg, 51%) as a colorless oil. $^1$H NMR was performed at 400 MHz with CDCl$_3$ as solvent to characterize the titled compound, results are as follows: δ=7.96 (d, J=7.6 Hz, 1H), 7.46 (t, J=7.0 Hz, 1H), 7.31-7.25 (m, 2H), 4.83 (s, 2H), 4.28 (t, J=6.2 Hz, 2H), 3.00 (q, J=7.6 Hz, 2H), 2.47 (t, J=7.4 Hz, 2H), 2.06-1.99 (m, 2H), 1.24 (t, J=7.4 Hz, 3H).

Example 1-81

Intermediate Compound 81':
2-(4-hydroxybutoxy)-2-oxoethyl 2,4-dimethylbenzoate

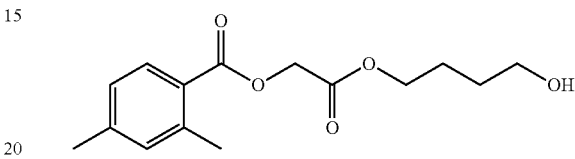

Et$_3$N (364 mg, 3.6 mmol) and 4-hydroxybutyl 2-chloroacetate (300 mg, 1.81 mmol) to a stirred solution of 2,4-dimethylbenzoic acid (405 mg, 2.7 mmol) in acetone (10 mL). The reaction was stirred at 50° C. for 5 h. After that, the reaction mixture was partitioned between DCM (20 mL) and H$_2$O (10 mL). The aqueous phase was separated and extracted with DCM (10 mL). The combined organic phase was washed with saturated brine (20 mL), dried over anhydrous Na$_2$SO$_4$ and evaporated. The residue was purified by a silica gel flash column with Hex/EA=6:1 to yield the titled compound (350 mg, 69%) as a colorless oil. $^1$H NMR was performed at 400 MHz with CDCl$_3$ as solvent to characterize the titled compound, results are as follows: δ=7.92 (d, J=8.0 Hz, 1H), 7.08-7.06 (m, 2H), 4.81 (s, 2H), 4.24 (t, J=6.6 Hz, 2H), 3.67 (t, J=6.2 Hz, 2H), 2.59 (s, 3H), 2.36 (s, 3H), 1.80-1.73 (m, 2H), 1.66-1.60 (m, 2H), 1.44 (br. s., 1H).

Compound 81:
4-(2-(2,4-dimethylbenzoyloxy)acetoxy)butanoic Acid

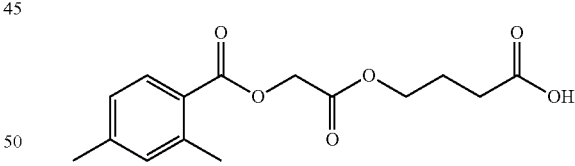

Jones reagent was added in portions to a stirred mixture of 2-(4-hydroxybutoxy)-2-oxoethyl 2,4-dimethylbenzoate (300 mg, 1.07 mmol) and Celite® (diatomaceous earth, 2 g) in acetone (10 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (150 mg, 48%) as a colorless oil. $^1$H NMR was performed at 400 MHz with CDCl$_3$ as solvent to characterize the titled compound, results are as follows: δ=7.92 (d, J=8.4 Hz, 1H), 7.18-7.06 (m, 2H), 4.81 (s, 2H), 4.27 (t, J=6.2 Hz, 2H), 2.58 (s, 3H), 2.47 (t, J=7.4 Hz, 2H), 2.36 (s, 3H), 2.06-2.00 (m, 2H).

Example 1-82

Intermediate Compound 82':
2-(4-hydroxybutoxy)-2-oxoethyl
2,3-dimethoxybenzoate

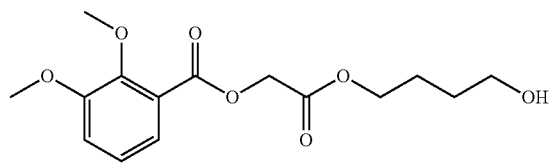 [SMILES: COc1cccc(C(=O)OCC(=O)OCCCCO)c1OC]

Et$_3$N (364 mg, 3.6 mmol) and 4-hydroxybutyl 2-chloroacetate (300 mg, 1.81 mmol) was added to a stirred solution of 2,3-dimethoxybenzoic acid (655 mg, 3.6 mmol) in acetone (10 mL). The reaction was stirred at 50° C. for 5 h. After that, the reaction mixture was partitioned between DCM (20 mL) and H$_2$O (10 mL). The aqueous phase was separated and extracted with DCM (10 mL). The combined organic phase was washed with saturated brine (20 mL), dried over anhydrous Na$_2$SO$_4$ and evaporated. The residue was purified by a silica gel flash column with Hex/EA=2:1 to yield the titled compound (200 mg, 35%) as a colorless oil. $^1$H NMR was performed at 400 MHz with CDCl$_3$ as solvent to characterize the titled compound, results are as follows: δ=7.43 (dd, J=2.4, 6.8 Hz, 1H), 7.14-7.08 (m, 2H), 4.84 (s, 2H), 4.25 (t, J=6.5 Hz, 2H), 3.93 (s, 3H), 3.89 (s, 3H), 3.67 (t, J=6.2 Hz, 2H), 1.81-1.74 (m, 2H), 1.67-1.60 (m, 2H).

Compound 82:
4-(2-(2,3-dimethoxybenzoyloxy)acetoxy)butanoic Acid

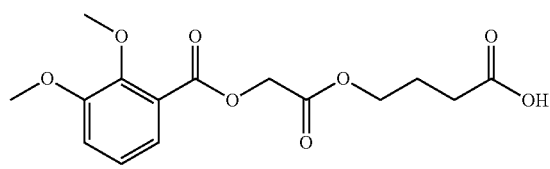 [SMILES: COc1cccc(C(=O)OCC(=O)OCCCC(=O)O)c1OC]

Jones reagent was added in portions to a stirred mixture of 2-(4-hydroxybutoxy)-2-oxoethyl 2,3-dimethoxybenzoate (200 mg, 0.64 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=5:1-2:1 to yield the titled compound (100 mg, 48%) as a colorless oil. $^1$H NMR was performed at 400 MHz with CDCl$_3$ as solvent to characterize the titled compound, results are as follows: δ=7.43 (dd, J=2.6, 7.0 Hz, 1H), 7.14-7.09 (m, 2H), 4.84 (s, 2H), 4.27 (t, J=6.0 Hz, 2H), 3.93 (s, 3H), 3.89 (s, 3H), 2.47 (t, J=7.2 Hz, 2H), 2.06-1.99 (m, 2H).

Example 1-83

Intermediate Compound 83':
2-(4-hydroxybutoxy)-2-oxoethyl benzoate

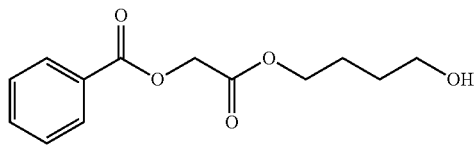 [SMILES: O=C(COC(=O)c1ccccc1)OCCCCO]

Et$_3$N (364 mg, 3.6 mmol) and 4-hydroxybutyl 2-chloroacetate (300 mg, 1.81 mmol) was added to a stirred solution of benzoic acid (439 mg, 3.6 mmol) in acetone (10 mL). The reaction was stirred at 50° C. for 5 h. After that, the reaction mixture was partitioned between DCM (20 mL) and H$_2$O (10 mL). The aqueous phase was separated and extracted with DCM (10 mL). The combined organic phase was washed with saturated brine (20 mL), dried over anhydrous Na$_2$SO$_4$ and evaporated. The residue was purified by a silica gel flash column with Hex/EA=6:1 to yield the titled compound (260 mg, 57%) as a colorless oil. $^1$H NMR was performed at 400 MHz with CDCl$_3$ as solvent to characterize the titled compound, results are as follows: δ=8.10 (d, J=7.2 Hz, 2H), 7.60 (t, J=7.4 Hz, 1H), 7.47 (t, J=7.8 Hz, 2H), 4.85 (s, 2H), 4.25 (t, J=6.6 Hz, 2H), 3.67 (t, J=6.2 Hz, 2H), 1.80-1.73 (m, 2H), 1.66-1.59 (m, 2H).

Compound 83: 4-(2-(benzoyloxy)acetoxy)butanoic Acid

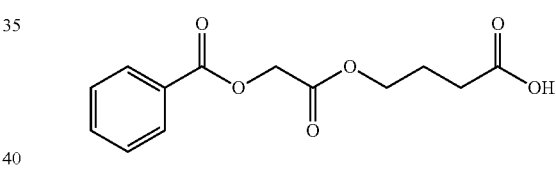

Jones reagent was added in portions to a stirred mixture of 2-(4-hydroxybutoxy)-2-oxoethyl benzoate (250 mg, 0.99 mmol) and Celite® (diatomaceous earth, 2 g) in acetone (5 mL) at 0° C. The reaction proceeded at 0° C. for over 1 h and the reaction progress was monitored by TLC. After completion, the reaction was quenched with drops of iPrOH, diluted with EA (10 mL) and then filtered. The filtered cake was washed with EA (5 mL) and the combined filtrate was washed with saturated brine (2 mL×2), dried over anhydrous Na$_2$SO$_4$ and concentrated. The residue was purified by a silica gel flash column with Hex/EA=10:1-5:1 to yield the titled compound (140 mg, 53%) as a white solid. $^1$H NMR was performed at 400 MHz with CDCl$_3$ as solvent to characterize the titled compound, results are as follows: δ=8 10 (d, J=7.2 Hz, 2H), 7.60 (t, J=7.4 Hz, 1H), 7.47 (t, J=7.8 Hz, 2H), 4.85 (s, 2H), 4.27 (t, J=6.2 Hz, 2H), 2.46 (t, J=7.4 Hz, 2H), 2.05-1.98 (m, 2H).

Scheme 14:

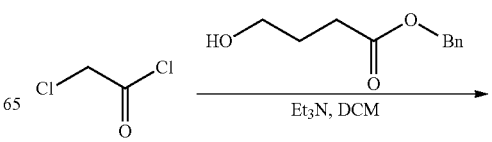

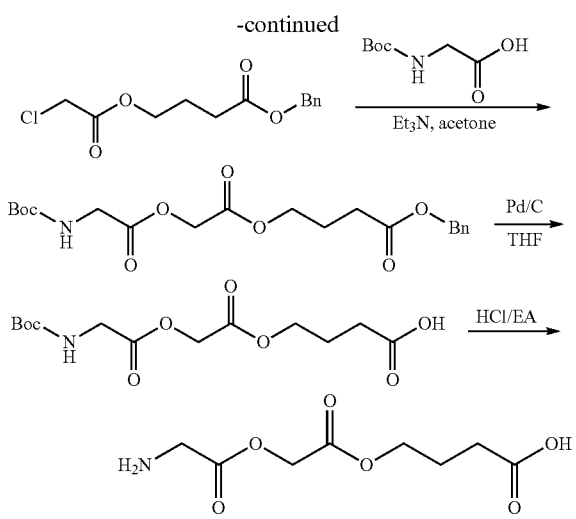

Example 1-84

Intermediate Compound 84': benzyl 4-(2-chloroacetoxy)butanoate

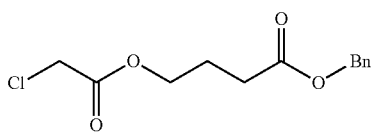 [SMILES: O=C(CCl)OCCCC(=O)OCc1ccccc1]

A solution of 2-chloroacetyl chloride (865 mg, 7.65 mmol) in DCM (10 mL) was added to a stirred solution of benzyl 4-hydroxybutanoate (1350 mg, 6.96 mmol) and Et$_3$N (1406 mg, 13.92 mmol) in DCM (10 mL) at 0° C. during 10 min. The reaction was stirred at 25° C. for 16 h. After completion, the reaction mixture was diluted with water (10 mL). The organic phase was collected, washed with brine (5 mL), dried over Na$_2$SO$_4$ and concentrated. The residue was purified by a silica gel flash column with PE/EA=8:1 to afford the titled compound (977 mg, 52%) as a colorless oil. $^1$H NMR was performed at 400 MHz with CDCl$_3$ as solvent to characterize the titled compound, results are as follows: δ=7.41-7.30 (m, 5H), 5.13 (s, 2H), 4.24 (t, J=6.4 Hz, 2H), 4.02 (s, 2H), 2.47 (t, J=7.4 Hz, 2H), 2.07-2.00 (m, 2H).

Intermediate Compound 84': benzyl 4-(2-2-(tert-butoxycarbonyl)aminoacetoxy)butanoate

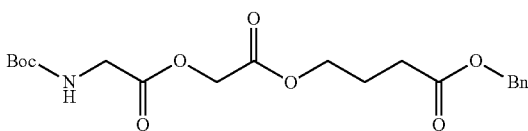 [SMILES: CC(C)(C)OC(=O)NCC(=O)OCC(=O)OCCCC(=O)OCc1ccccc1]

A solution of 2-(tert-butoxycarbonylamino)acetic acid (654 mg, 3.74 mmol), Et$_3$N (686 mg, 6.79 mmol) and benzyl 4-(2-chloroacetoxy)butanoate (917 mg, 3.40 mmol) in acetone (10 mL) was stirred at 50° C. for 16 h. After that, the mixture was diluted with EA (30 mL) and water (10 mL), the aqueous phase was separated and the organic phase was washed with brine (10 mL), dried over Na$_2$SO$_4$ and concentrated. The residue was purified by a silica gel flash column with PE/EA=5:1 to afford the titled compound (1.16 g, 84%) as a colorless oil. $^1$H NMR was performed at 400 MHz with CDCl$_3$ as solvent to characterize the titled compound, results are as follows: δ=7.41-7.32 (m, 5H), 5.13 (s, 2H), 5.01 (br. s., 1H), 4.64 (s, 2H), 4.22 (t, J=6.4 Hz, 2H), 4.04 (d, J=5.6 Hz, 2H), 2.45 (t, J=7.2 Hz, 2H), 2.05-1.98 (t, J=6.8 Hz, 2H), 1.45 (s, 9H).

Intermediate Compound 84''': 2,2-dimethyl-4,7,10-trioxo-3,8,11-trioxa-5-azapentadecan-15-oic Acid

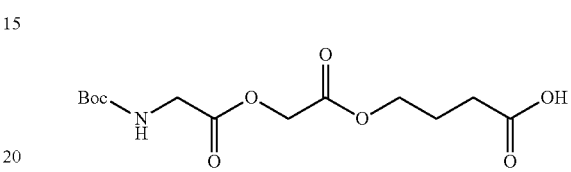

Pd/C (100 mg) was added to a stirred solution of benzyl 4-(2-2-(tert-butoxycarbonyl)aminoacetoxyacetoxy)butanoate (1 g, 2.44 mmol) in THF (10 mL), the mixture was stirred at 25° C. under H$_2$ atmosphere for 16 h. After that, the reaction mixture was filtered through Celite® (diatomaceous earth). The filtered cake was washed with EA (5 mL), the combined filtrate was concentrated. The residue was purified by prep-HPLC to afford the titled compound (600 mg, 77%) as a colorless oil. $^1$H NMR was performed at 400 MHz with CDCl$_3$ as solvent to characterize the titled compound, results are as follows: δ=5.11 (br. s., 1H), 4.70 (s, 2H), 4.24 (t, J=5.8 Hz, 2H), 4.11 (d, J=6.0 Hz, 2H), 2.46 (t, J=6.8 Hz, 2H), 2.10-2.02 (m, 2H), 1.46 (s, 9H).

Compound 84: 4-(2-2-aminoacetoxy)acetoxy)butanoic Acid

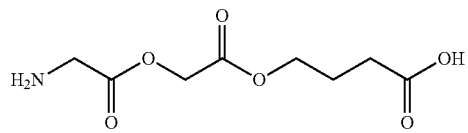 [SMILES: NCC(=O)OCC(=O)OCCCC(=O)O]

2,2-dimethyl-4,7,10-trioxo-3,8,11-trioxa-5-azapentadecan-15-oic acid (600 mg, 1.88 mmol) was dissolved in HCl/EA (6 mL, ~2 M) and the solution was stirred at 25° C. for 16 h. After that, the reaction mixture was filtered, the collected solid was washed with Et$_2$O (5 mL) to afford the titled compound (450 mg, 94%) as crystalline solids in HCl salt form. $^1$H NMR was performed at 400 MHz with D$_2$O as solvent to characterize the titled compound, results are as follows: δ=4.84 (s, 2H), 4.23 (t, J=6.0 Hz, 2H), 4.03 (s, 2H), 2.43 (t, J=7.2 Hz, 2H), 1.98-1.91 (m, 2H).

Scheme 15:

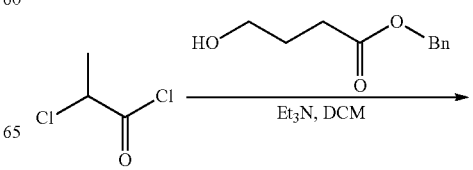

-continued

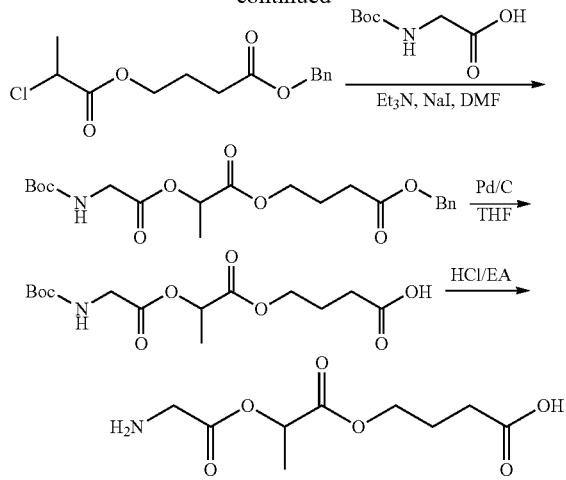

Example 1-85

Intermediate Compound 85': benzyl 4-(2-chloropropanoyloxy)butanoate

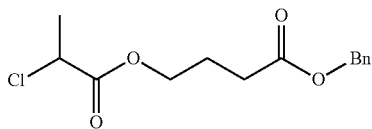 [SMILES: CC(Cl)C(=O)OCCCC(=O)OCc1ccccc1]

A solution of 2-chloropropanoyl chloride (1080 mg, 8.50 mmol) in DCM (10 mL) was dropwise added to a stirred solution of benzyl 4-hydroxybutanoate (1.5 g, 7.73 mmol) Et$_3$N (1562 mg, 15.47 mmol) in DCM (10 mL) at 0° C., the reaction was stirred at 25° C. for 16 h. After that, the reaction mixture was diluted with water (10 mL), the aqueous phase was separated and the organic phase was washed with brine (10 mL), dried over Na$_2$SO$_4$ and concentrated. The residue was purified by a silica gel flash column with PE/EA=8:1 to afford the titled compound (1.38 g, 63%) as a colorless oil. $^1$H NMR was performed at 400 MHz with CDCl$_3$ as solvent to characterize the titled compound, results are as follows: δ=7.41-7.30 (m, 5H), 5.13 (s, 2H), 4.36 (q, J=7.0 Hz, 1H), 4.22 (t, J=6.0 Hz, 2H), 2.48 (t, J=7.4 Hz, 2H), 2.07-2.00 (m, 2H), 1.67 (d, J=6.8 Hz, 3H).

Intermediate Compound 85'': benzyl 4-(2-(2-(tert-butoxycarbonyl)aminoacetoxy)propanoyloxy)butanoate

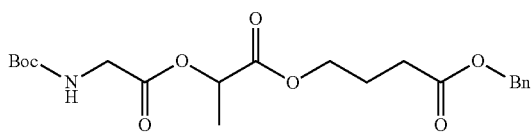 [SMILES: CC(OC(=O)CNC(=O)OC(C)(C)C)C(=O)OCCCC(=O)OCc1ccccc1]

Et$_3$N (782 mg, 7.75 mmol) and NaI (20 mg) was added to a stirred solution of 2-(tert-butoxycarbonylamino)acetic acid (746 mg, 4.26 mmol) and benzyl 4-(2-chloropropanoyloxy) butanoate (1.1 g, 3.87 mmol) in DMF (15 mL), the reaction mixture was stirred at 70° C. for 16 h. After that, the mixture was concentrated, the residue was partitioned between EA (20 mL) and water (10 mL). The aqueous phase was separated, the organic phase was washed with brine (10 mL), dried over Na$_2$SO$_4$ and concentrated. The residue was purified by a silica gel flash column with PE/EA=5:1 to afford the titled compound (1.1 g, 69%) as a colorless oil. $^1$H NMR was performed at 400 MHz with CDCl$_3$ as solvent to characterize the titled compound, results are as follows: δ=7.43-7.29 (m, 5H), 5.15-5.09 (m, 3H), 5.00 (br. s., 1H), 4.19 (t, J=6.2 Hz, 2H), 4.06 (dd, J=6.0, 18.4 Hz, 1H), 3.93 (dd, J=5.0, 14.2 Hz, 1H), 2.44 (t, J=7.2 Hz, 2H), 2.03-1.97 (m, 2H), 1.49 (d, J=6.8 Hz, 3H), 1.45 (s, 9H).

Intermediate Compound 85''': 2,2,9-trimethyl-4,7,10-trioxo-3,8,11-trioxa-5-azapentadecan-15-oic Acid

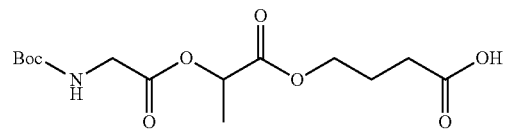 [SMILES: CC(OC(=O)CNC(=O)OC(C)(C)C)C(=O)OCCCC(=O)O]

Pd/C (100 mg) was added to a stirred solution of benzyl 4-(2-(2-(tert-butoxycarbonyl)aminoacetoxy)propanoyloxy) butanoate (1.1 g, 2.60 mmol) in THF (10 mL), the reaction mixture was stirred at 25° C. under H$_2$ atmosphere for 16 h. After that, the reaction mixture was filtered through Celite® (diatomaceous earth) and the filtered cake was washed with EA (5 mL). The combined filtrate was concentrated, the residue was purified by prep-HPLC to afford the titled compound (800 mg, 92%) as a colorless oil. $^1$H NMR was performed at 400 MHz with CDCl$_3$ as solvent to characterize the titled compound, results are as follows: δ=5.21 (q, J=6.8 Hz, 1H), 5.12 (br. s., 1H), 4.29-4.09 (m, 3H), 3.94 (dd, J=4.6, 18.8 Hz, 1H), 2.45 (t, J=6.8 Hz, 2H), 2.09-1.98 (m, 2H), 1.50 (d, J=7.2 Hz, 3H), 1.46 (s, 9H).

Compound 85: 4-(2-(2-aminoacetoxy)propanoyloxy)butanoic Acid

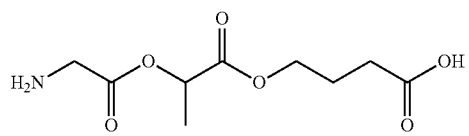 [SMILES: CC(OC(=O)CN)C(=O)OCCCC(=O)O]

2,2,9-trimethyl-4,7,10-trioxo-3,8,11-trioxa-5-azapentadecan-15-oic acid (770 mg, 2.31 mmol) was dissolved in HCl/EA (10 mL, ~2 M) at 0° C. and the solution was stirred at 25° C. for 16 h. After that, the reaction mixture was concentrated, the residue was purified by prep-HPLC to afford the titled compound (48 mg, 9%) as a colorless oil in HCl salt form. $^1$H NMR was performed at 400 MHz with D$_2$O as solvent to characterize the titled compound, results are as follows: δ=5.26 (d, J=7.2 Hz, 1H), 4.23 (dt, J=2.8, 6.0 Hz, 2H), 4.00 (d, J=1.6 Hz, 2H), 2.45 (t, J=7.0 Hz, 2H), 2.01-1.91 (m, 2H), 1.50 (d, J=7.2 Hz, 3H).

Scheme 16:

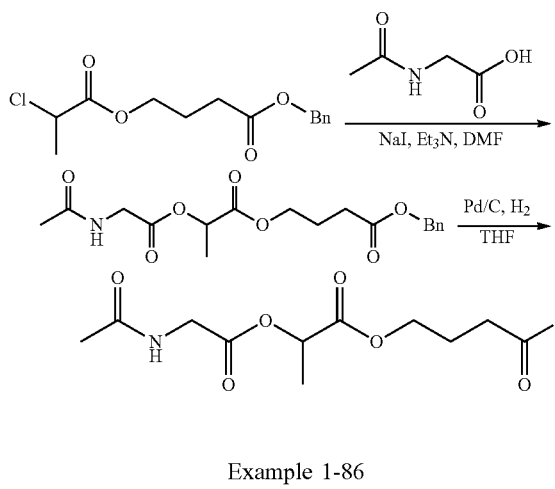

Example 1-86

Intermediate Compound 86': benzyl 4-(2-(2-acetamidoacetoxy)propanoyloxy)butanoate

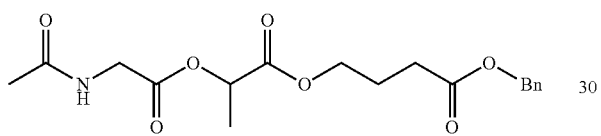

A mixture of benzyl 4-(2-chloropropanoyloxy)butanoate (500 mg, 1.76 mmol), 2-acetamidoacetic acid (260 mg, 2.22 mmol), NaI (138 mg, 0.92 mmol) and Et$_3$N (0.52 mL, 3.69 mmol) in DMF (5 mL) was stirred at 80° C. for 16 h. The reaction mixture was filtered and the filtrate was concentrated. The residue was purified by silica gel flash column with PE/EA=5:1 to afford the titled compound (500 mg, 78%) as a colorless oil. $^1$H NMR was performed at 400 MHz with CDCl$_3$ as solvent to characterize the titled compound, results are as follows: δ=7.39-7.31 (m, 5H), 6.01 (br. s., 1H), 5.13 (s, 2H), 5.10 (t, J=3.2 Hz, 1H), 4.25-4.18 (m, 3H), 4.03 (dd, J=4.8, 18.8 Hz, 1H), 2.44 (t, J=7.4 Hz, 2H), 2.04-1.97 (m, 5H), 1.50 (d, J=7.2 Hz, 3H).

Compound 86: 4-(2-(2-acetamidoacetoxy)propanoyloxy)butanoic Acid

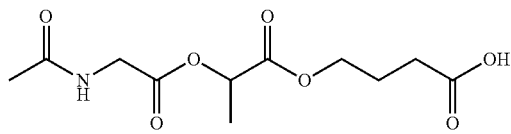 [SMILES: CC(=O)NCC(=O)OC(C)C(=O)OCCCC(=O)O]

Pd/C (150 mg) was added to a stirred solution of benzyl 4-(2-(2-acetamidoacetoxy)propanoyloxy)butanoate (500 mg, 1.37 mmol) in THF (10 mL), the reaction was stirred at 25° C. for 16 h under H$_2$ atmosphere. After that, the reaction mixture was filtered and the filtrate was concentrated. The residue was purified by a silica gel flash column with PE/EA=1:50 to afford the titled compound (280 mg, 74%) as a white solid. $^1$H NMR was performed at 400 MHz with d$_6$-DMSO as solvent to characterize the titled compound, results are as follows: δ=12.15 (s, 1H), 8.34 (t, J=5.6 Hz, 1H), 5.02 (q, J=6.8 Hz, 1H), 4.12-4.06 (m, 2H), 3.93 (dd, J=6.2, 17.8 Hz, 1H), 3.84 (dd, J=6.0, 17.6 Hz, 1H), 2.28 (t, J=7.2 Hz, 2H), 1.85 (s, 3H), 1.84-1.77 (m, 2H), 1.41 (d, J=7.2 Hz, 3H).

Scheme 17:

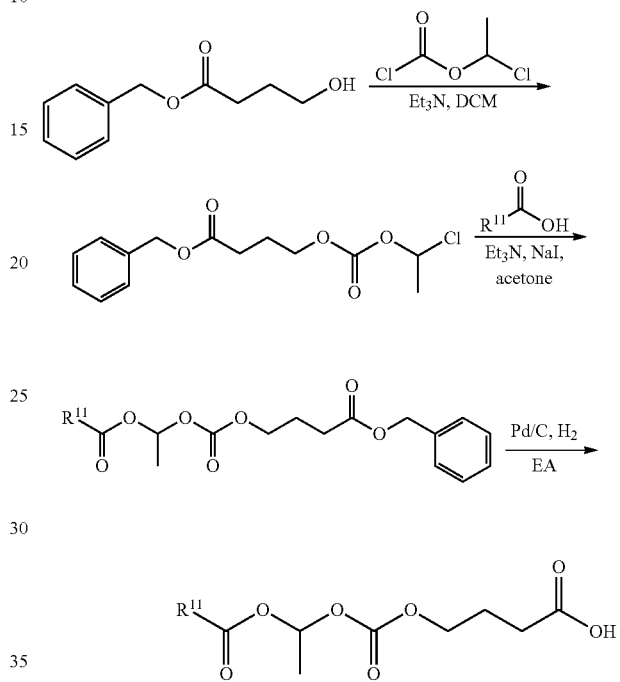

Example 1-87

Intermediate Compound 87': benzyl 4-((1-chloroethoxy)carbonyloxy)butanoate

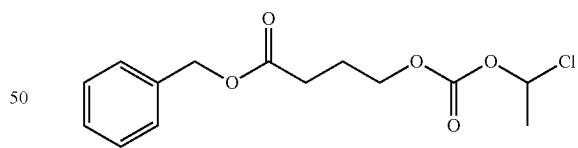

1-chloroethyl carbonochloridate (1.0 g, 7.2 mmol) was added dropwise to a solution of benzyl 4-hydroxybutanoate (1.0 g, 5.2 mmol) and Et$_3$N (1.1 mL, 1.7 mmol) in DCM (10 mL) over 5 min at −5-0° C. After that, the reaction was quenched by water (5 mL). The organic layer was separated, dried over Na$_2$SO$_4$ and filtered. The filtrate was concentrated and the residue was purified by silica gel flash column with PE/EA=20:1-5:1 to afford titled compound (680 mg, 44%) as a colorless oil. $^1$H NMR was performed at 400 MHz with CDCl$_3$ as solvent to characterize the titled compound, results are as follows: δ=7.39-7.33 (m, 5H), 6.41 (q, J=5.6 Hz, 1H), 5.13 (s, 2H), 4.26 (t, J=6.4 Hz, 2H), 2.49 (t, J=7.4 Hz, 2H), 2.09-2.02 (m, 2H), 1.82 (d, J=6.0 Hz, 3H).

Intermediate Compound 87'': benzyl 4-((1-acetoxyethoxy)carbonyloxy)butanoate

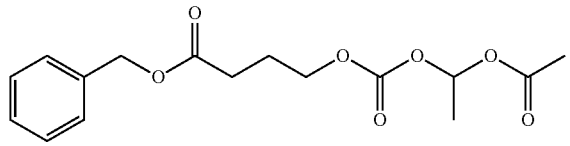 [SMILES: CC(=O)OC(C)OC(=O)OCCCC(=O)OCc1ccccc1]

A solution of benzyl 4-((1-chloroethoxy)carbonyloxy)butanoate (180 mg, 598 μmol), acetic acid (720 mg, 12.0 mmol) and Et₃N (151 mg, 1.5 mmol) in acetone (4 mL) was heated under reflux for 2 days. The reaction was diluted with EA (20 mL) and washed with water (10 mL). The organic layer was separated, dried over Na₂SO₄ and filtered. The filtrate was concentrated and the residue was purified by a silica gel flash column with PE/EA=10:1-3:1 to afford the titled compound (120 mg, 64%) as a colorless oil. ¹H NMR was performed at 400 MHz with CDCl₃ as solvent to characterize the titled compound, results are as follows: δ=7.38-7.33 (m, 5H), 6.74 (q, J=3.6 Hz, 1H), 5.13 (s, 2H), 4.21 (t, J=6.2 Hz, 2H), 2.48 (t, J=4.8 Hz, 2H), 2.08 (s, 3H), 2.06-2.01 (m, 2H), 1.51 (d, J=3.6 Hz, 3H).

Compound 87: 4-((1-acetoxyethoxy)carbonyloxy)butanoic Acid

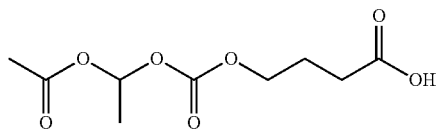 [SMILES: CC(=O)OC(C)OC(=O)OCCCC(=O)O]

Pd/C (10 mg) was added to a mixture of benzyl 4-((1-acetoxyethoxy)carbonyloxy)butanoate (110 mg, 339 μmol) in EA (2 mL). The reaction was stirred under H₂ atmosphere for 16 h at 25° C. After that, the reaction mixture was filtered and the filtrate was concentrated to afford the titled compound (70 mg, 88%) as a colorless oil. ¹H NMR was performed at 400 MHz with CDCl₃ as solvent to characterize the titled compound, results are as follows: δ=6.75 (q, J=5.2 Hz, 1H), 4.23 (t, J=6.2 Hz, 2H), 2.49 (t, J=7.2 Hz, 2H), 2.09 (s, 3H), 2.06-1.99 (m, 2H), 1.52 (d, J=5.2 Hz, 3H).

Example 1-88

Intermediate Compound 88': benzyl 4-(1-(isobutyryloxy)ethoxycarbonyloxy)butanoate

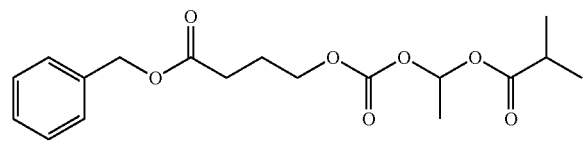 [SMILES: CC(OC(=O)OCCCC(=O)OCc1ccccc1)OC(=O)C(C)C]

A solution of benzyl 4-((1-chloroethoxy)carbonyloxy)butanoate (300 mg, 998 μmol), isobutyric acid (879 mg, 10.0 mmol), NaI (179 mg, 1.2 mmol) and Et₃N (121 mg, 1.2 mmol) in acetone (6 mL) was heated under reflux for 2 days. After that, the reaction mixture was diluted with EA (20 mL) and washed with saturated NaHCO₃ (10 mL). The organic layer was separated, dried over Na₂SO₄ and filtered. The filtrate was concentrated and the residue was purified by a silica gel column with PE/EA=50:1-5:1 to afford the titled compound (300 mg, 85%) as a colorless oil. ¹H NMR was performed at 400 MHz with CDCl₃ as solvent to characterize the titled compound, results are as follows: δ=7.42-7.29 (m, 5H), 6.74 (q, J=5.2 Hz, 1H), 5.12 (s, 2H), 4.21 (t, J=6.2 Hz, 2H), 2.58-2.51 (m, 1H), 2.48 (t, J=7.2 Hz, 2H), 2.06-2.00 (m, 2H), 1.51 (d, J=5.6 Hz, 3H), 1.17 (d, J=7.2 Hz, 6H).

Compound 88: 4-(1-(isobutyryloxy)ethoxycarbonyloxy)butanoic Acid

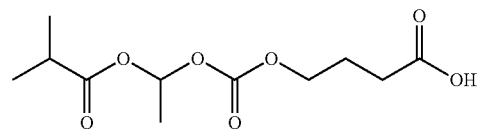 [SMILES: CC(OC(=O)OCCCC(=O)O)OC(=O)C(C)C]

Pd/C (28 mg) was added to a mixture of benzyl 4-(1-(isobutyryloxy)ethoxycarbonyloxy)butanoate (280 mg, 795 μmol) in EA (6 mL). The reaction was stirred under H₂ atmosphere for 16 h at 25° C. After that, the reaction mixture was filtered and the filtrate was concentrated to afford the titled compound (200 mg, 96%) as a colorless oil. ¹H NMR was performed at 400 MHz with CDCl₃ as solvent to characterize the titled compound, results are as follows: δ=6.74 (q, J=5.6 Hz, 1H), 4.23 (t, J=6.0 Hz, 2H), 2.60-2.53 (m, 1H), 2.49 (t, J=7.2 Hz, 2H), 2.06-1.99 (m, 2H), 1.52 (d, J=5.2 Hz, 3H), 1.18 (d, J=6.8 Hz, 6H).

Example 1-89

Intermediate Compound 89': 1-((4-benzyloxy-4-oxobutoxy)carbonyloxy)ethyl benzoate

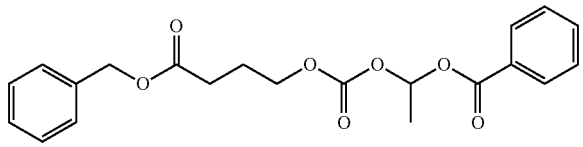 [SMILES: CC(OC(=O)OCCCC(=O)OCc1ccccc1)OC(=O)c1ccccc1]

A solution of benzyl 4-((1-chloroethoxy)carbonyloxy)butanoate (300 mg, 998 μmol), benzoic acid (244 mg, 2.0 mmol), NaI (179 mg, 1.2 mmol) and Et₃N (121 mg, 1.2 mmol) in acetone (6 mL) was heated under reflux for 3 days. After that, the reaction was diluted with EA (20 mL) and washed with saturated NaHCO₃ (10 mL). The organic layer was separated, dried over Na₂SO₄ and filtered. The filtrate was concentrated and the residue was purified by a silica gel flash column with PE/EA=100:1-10:1 to afford the titled compound (240 mg, 62%) as a colorless oil. ¹H NMR was performed at 400 MHz with CDCl₃ as solvent to characterize the titled compound, results are as follows: δ=8.05 (d, J=7.2 Hz, 2H), 7.58 (t, J=7.4 Hz, 1H), 7.44 (t, J=7.6 Hz, 2H), 7.39-7.28 (m, 5H), 7.02 (q, J=5.6 Hz, 1H), 5.11 (s, 2H), 4.32-4.12 (m, 2H), 2.48 (t, J=7.6 Hz, 2H), 2.07-1.97 (m, 2H), 1.65 (d, J=5.6 Hz, 3H).

Compound 89:
4-(1-(benzoyloxy)ethoxycarbonyloxy)butanoic Acid

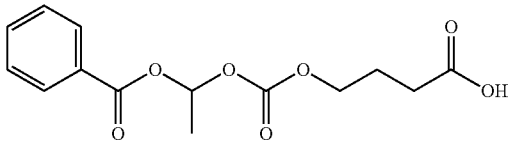 [SMILES: CC(OC(=O)OCCCC(=O)O)OC(=O)c1ccccc1]

Pd/C (20 mg) was added to a mixture of 1-((4-benzyloxy-4-oxobutoxy)carbonyloxy)ethyl benzoate (200 mg, 518 μmol) in EA (4 mL). The reaction was stirred under $H_2$ atmosphere for 16 h at 25° C. After that, the reaction mixture was filtered and the filtrate was concentrated to afford the titled compound (120 mg, 78%) as a sticky oil. $^1$H NMR was performed at 400 MHz with $CDCl_3$ as solvent to characterize the titled compound, results are as follows: δ=8.06 (d, J=7.2 Hz, 2H), 7.59 (t, J=7.4 Hz, 1H), 7.45 (t, J=7.6 Hz, 2H), 7.03 (q, J=5.6 Hz, 1H), 4.24 (t, J=6.4 Hz, 2H), 2.49 (t, J=7.2 Hz, 2H), 2.06-1.99 (m, 2H), 1.66 (d, J=5.6 Hz, 3H).

Example 1-90

Intermediate Compound 90': benzyl 4-(3,10,10-trimethyl-5,8-dioxo-2,4,9-trioxa-7-azaundecan-1-oyloxy)butanoate A solution of benzyl 4-((1-chloroethoxy)carbonyloxy) butanoate (450 mg, 1.5 mmol), 2-(tert-butoxycarbonylamino)acetic acid (524 mg, 3.0 mmol), NaI (449 mg, 3.0 mmol) and $Et_3N$ (182 mg, 1.8 mmol) in acetone (10 mL) was heated under reflux for 3 days. The reaction mixture was filtered and the filtrate was concentrated. The residue was purified by a silica gel flash column with PE/EA=10:1-1.1 to afford the titled compound (390 mg, 59%) as a colorless sticky oil. $^1$H NMR was performed at 400 MHz with $CDCl_3$ as solvent to characterize the titled compound, results are as follows: δ=7.39-7.31 (m, 5H), 6.80 (q, J=5.6 Hz, 1H), 5.12 (s, 2H), 4.97 (br. s., 1H), 4.21 (t, J=6.2 Hz, 2H), 4.03-3.84 (m, 2H), 2.48 (t, J=7.4 Hz, 2H), 2.06-2.00 (m, 2H), 1.53 (d, J=5.2 Hz, 3H), 1.44 (s, 9H).

Intermediate Compound 90": 2,2,9-trimethyl-4,7,11-trioxo-3,8,10,12-tetraoxa-5-azahexadecan-16-oic Acid Pd/C (38 mg) was added to a mixture of benzyl 4-(3,10,10-trimethyl-5,8-dioxo-2,4,9-trioxa-7-azaundecan-1-oyloxy)butanoate (380 mg, 865 μmol) in EA (8 mL). The reaction was stirred under $H_2$ atmosphere for 16 h at 25° C. After that, the reaction mixture was filtered and the filtrate was concentrated to afford the titled compound (280 mg, 93%) as a sticky oil. $^1$H NMR was performed at 400 MHz with $CDCl_3$ as solvent to characterize the titled compound, results are as follows: δ=6.82 (q, J=5.2 Hz, 1H), 5.03 (br. s., 1H), 4.34-4.15 (m, 2H), 3.96 (d, J=6.0 Hz, 2H), 2.49 (t, J=7.0 Hz, 2H), 2.13-1.96 (m, 2H), 1.54 (d, J=5.6 Hz, 3H), 1.45 (s, 9H).

Compound 90:
4-(1-(2-aminoacetoxy)ethoxycarbonyloxy)butanoic Acid

A solution of 2,2,9-trimethyl-4,7,11-trioxo-3,8,10,12-tetraoxa-5-azahexadecan-16-oic acid (280 mg, 802 μmol) in HCl/EA (5 mL, ~2 M) was stirred for 16 h at 25° C. The precipitate was formed and filtered. The filtered cake was washed with EA (10 mL) and then dried in vacuo to afford the titled compound (168 mg, 84%) as a white solid in HCl salt form. $^1$H NMR was performed at 400 MHz with $D_2O$ as solvent to characterize the titled compound, results are as follows: δ=6.81 (q, J=5.6 Hz, 1H), 4.22 (t, J=6.0 Hz, 2H), 3.94 (s, 2H), 2.44 (t, J=7.2 Hz, 2H), 1.98-1.92 (m, 2H), 1.52 (d, J=5.2 Hz, 3H).

Example 2: Metabolic Stability Assay of the Test Compounds

Rat/Human Liver S9 Fractions Metabolic Stability Assay

The protocol for rat/human liver S9 fractions metabolic stability assay is employed to determine the half-life ($T_{1/2}$) of the compounds of the present disclosure and their releasing efficiency of converting from the prodrugs to GHB in vitro.

The following is the study outline for S9 assay: 1) For GHB releasing efficiency assay, pooled liver S9 fractions (human or rat) in mixed gender were obtained from commercial vendors (e.g., Xenotech) and stored at −80° C. prior to use. 2) A master solution in the incubation plate containing phosphate buffer, ultra-pure $H_2O$, $MgCl_2$ solution and liver S9 fraction was made to keep S9 fractions at 1 mg/mL final concentration. The mixture was pre-warmed at 37° C. water bath for 5 minutes. 3) Add 4 μL of 500 μM test compound solution to the master solution plate at the final concentration of 5 μM test compound. The reaction was started with the addition of 40 μL of 10 mM NADPH and carried out at 37° C. 4) 50 μL aliquots of the reaction solution were taken out and put into new plates at different time points including 0, 15, 30, 45 and 60 minutes, and incubated at 37° C. water bath with shaking at 60 rpm. The reaction was stopped by adding 200 μL of cold quench solution (methanol containing internal standards) at the appointed time points. The plates were centrifuged at 3220 g at 4° C. for 40 minutes to precipitate protein. 5) 100 μL of the supernatant was transferred to a new plate. The supernatant was diluted with water according to the LC/MS signal response and peak shape, mixed well and analyzed using LC/MS/MS for measurement of test compounds and GHB. The measurement results were then used for calculation of half-life ($T_{1/2}$) of the test compounds and their conversion efficiency into GHB in S9 fractions. GHB releasing efficiency is calculated by dividing the detected amount of GHB by the total amount of GHB that can be released by the test compound. Data are shown as below in Table 1.

TABLE 1

Metabolic Stability of Test Compounds in Human and Rat Liver S9 Fractions

| Test Compounds | Species | $T_{1/2}$ (min) | GHB releasing efficiency (%) at 60 min point |
|---|---|---|---|
| Compound 32 | Human | 40.43 | 47 |
| 4-(phenoxycarbonyloxy) butanoic acid | Rat | 8.50 | 74 |
| hydrochloride salt of Compound 57 | Human | 2.15 | 61 |
| (S)-4-(2-amino-3-phenylpropanoyloxy) butanoic acid hydrochloride | Rat | 2.48 | 69 |
| Compound 66 | Human | 9.21 | 78 |
| 4-(2-acetamidoacetoxy) butanoic acid | Rat | 8.00 | 71 |
| Compound 67 | Human | 83.17 | 35 |
| (S)-4-(2-acetamido-3-methylbutanoyloxy) butanoic acid | Rat | 74.22 | 32 |
| Compound 64 | Human | 58.01 | 42 |
| 4-(2-isobutyramidoacetoxy) butanoic acid | Rat | 62.66 | 30 |
| Compound 89 | Human | 10.54 | 42 |
| 4-(1-(benzoyloxy)ethoxycarbonyloxy) butanoic acid | Rat | 17.48 | 51 |

The in vitro GHB releasing efficiency assay employing rat/human liver S9 fractions had shown that the prodrug compounds could be converted to GHB with variable releasing efficiencies, which suggested that they would be converted into GHB in the systemic circulation after being administered to rat/human.

Rat/Human Hepatocytes Metabolic Stability Assay

The protocol for rat/human hepatocytes metabolic stability assay is employed to determine the half-life ($T_{1/2}$) of the compounds of the present disclosure and their releasing efficiency of converting from the prodrugs to GHB in vitro.

The following is the study outline for hepatocytes assay:
1) For GHB releasing efficiency assay, rat hepatocytes in male gender and human hepatocytes in mixed gender were obtained from commercial vendors (e.g., Bioreclamation-IVT) and stored at −150° C. prior to use. 2) 30 mM stock solutions of test compounds were prepared in DMSO. Thawing medium and supplement incubation medium (serum-free) were placed in a 37° C. water bath for at least 15 minutes prior to use. Stock solutions were diluted to 500 μM by combining 295 μL acetonitrile and 5 μL of 30 mM stock solution. 3) Vials of cryopreserved hepatocytes were removed from storage, ensured that vials remain at cryogenic temperatures. The pressure was removed by loosening and re-tightening the cap. The vials were thawed in a 37° C. water bath with gently shaking. Vials were kept in water bath until all ice crystals had dissolved and were no longer visible. Vials were sprayed with 70% ethanol before being transferred to a biosafety cabinet. And then the contents were poured into the 50 mL thawing medium conical tube. Vials were centrifuged at 100 g for 10 minutes at room temperature. Thawing medium was aspirated and hepatocytes were resuspended with serum-free incubation medium to yield ~1.5×10⁶ cells/mL. 4) Cell viability and density were counted using a Trypan Blue exclusion, and then cells were diluted with serum-free incubation medium to a working cell density of 1×10⁶ viable cells/ml. 5) A portion of the hepatocytes at 1×10⁶ viable cells/mL was boiled for 10 min prior to adding to the plate as negative control to eliminate the enzymatic activity so that little or no substrate turnover should be observed. The inactivated hepatocytes were used to prepare negative samples, which were used to exclude the misleading factor that resulted from instability of chemical itself. 6) Aliquots of 247.5 μL hepatocytes were dispensed into each well of a 96-well non-coated plate. The plate was placed in the incubator on an orbital shaker at 500 rpm for approximately 10 minutes. 7) Aliquots of 2.5 μL of the 500 μM test compounds were added into respective wells of the non-coated 96-well plate to start the reaction. This assay was performed in duplicate. The plate was incubated in the incubator on an orbital shaker at 500 rpm for the designed time points. 8) 25 μL of contents were transferred and mixed with 6 volumes (150 μL) of cold acetonitrile with internal standard to terminate the reaction at time points of 0, 5, 15, 30, 60, 90 and 120 minutes. Samples were centrifuges for 25 minutes at 3220 g and aliquots of 100 μL of the supernatants were used for LC-MS/MS analysis for measurement of test compounds and GHB. The measurement results were then used for calculation of half-life ($T_{1/2}$) of the test compounds and their conversion efficiency into GHB in hepatocytes. Data are shown as below in Table 2.

TABLE 2

Metabolic Stability of Test Compounds in Human and Rat Hepatocytes

| Test Compounds | Species | $T_{1/2}$ (min) | GHB releasing efficiency (%) at 120 min point |
|---|---|---|---|
| Compound 58 | Human | 159.97 | 73 |
| (S)-4-(2-amino-3-methylbutanoyloxy) butanoic acid | Rat | 46.66 | 46 |
| Compound 66 | Human | 24.95 | 46 |
| 4-(2-acetamidoacetoxy) butanoic acid | Rat | 16.68 | 35 |
| Compound 67 | Human | 219.89 | 22 |
| (S)-4-(2-acetamido-3-methylbutanoyloxy) butanoic acid | Rat | 130.66 | 21 |

The in vitro GHB releasing efficiency assay employing rat/human hepatocytes had shown that prodrug compounds could be converted to GHB with variable releasing efficiencies, which suggested that they would be converted into GHB in the systemic circulation after being administered to rat/human.

Rat/Human Whole Blood Metabolic Stability Assay

The protocol for rat/human whole blood metabolic stability assay is employed to determine the releasing efficiency of the compounds of the present disclosure converting from the prodrugs to GHB in vitro.

The following is the study outline for whole blood assay:
1) For GHB releasing efficiency assay, rat whole blood in mixed gender was obtained from commercial vendors (e.g., SiBeiFu (Beijing) Laboratory Animal Science and Technology Co Ltd) and human whole blood was obtained from healthy volunteers in mixed gender, stored at 4° C. prior to use. 2) The stock solution of test compounds was prepared in DMSO and diluted at the final concentration of 500 μM. 3) 5 μL of 500 μM working solution was spiked to 495 μL whole blood to reach a final concentration of 5 μM. The final concentration of organic solvents was 1%. The assay was performed in duplicate. The reaction samples were incubated at 37° C. at approximately 60 rpm in a water bath. 4) Aliquots of 50 μL were taken from the reaction samples at 0, 15, 30, 45, 60 and 120 minutes. The reaction was stopped by the addition of 7 volumes of cold methanol containing internal standards. 5) All samples were vortexed for 10 minutes, followed by centrifugation at 3220 g for 30 minutes to precipitate proteins. 100 μL of the supernatant was transferred to a new plate. The supernatant was diluted with ultra pure water according to the LC-MS signal response and peak shape. Samples were analyzed using LC/MS/MS for measurement of test compounds and GHB. The measurement results were then used for calculation of conversion efficiency the test compounds into GHB in whole blood. Data are shown as below in Table 3.

TABLE 3

Metabolic Stability of Test Compounds in Human and Rat Whole Blood

| Test Compounds | Species | GHB releasing efficiency (%) at 120 min point |
|---|---|---|
| Compound 58 | Human | 42 |
| (S)-4-(2-amino-3-methylbutanoyloxy) butanoic acid | Rat | 85 |
| Compound 66 | Human | 76 |
| 4-(2-acetamidoacetoxy) butanoic acid | Rat | 100 |
| Compound 67 | Human | 45 |
| (S)-4-(2-acetamido-3-methylbutanoyloxy) butanoic acid | Rat | 83 | use. The animal dosing experiments were carried out in accordance to the National Institutes of Health Guide to the Care and Use of Laboratory Animals and the Animal Welfare Act. For GHB sodium salt, a single dose of 50 mg/kg was administered to each rat in two groups (n=3/group) via intravenous (IV) and oral (PO) administration, respectively. The vehicle used for GHB sodium salt is saline. For other test compounds, a single dose of each test compound was administered to each rat orally (n=3/group). The dosage of each test compound is listed in the Table 4. The vehicle used for dosing test compounds was 0.5% (w/v) Sodium Carboxyl Methyl Cellulose (CMC-Na) in saline. Blood samples were collected at specified time-points (pre-dose, 10 minutes, 0.5 hour, 1 hour, 2 hours, 4 hours, 6 hours) following administration to individual rats within IV and PO group. Blood samples were clotted on ice immediately, plasma samples were then isolated by centrifugation and stored frozen (−80° C.) until further analysis. The concentrations of GHB and all other test compounds were individually determined by LC/MS/MS assay. Various pharmacokinetic parameters were calculated using Phoenix™ WinNonlin® software. To quantify the bioconversion efficiency of the test compounds in the circulation system, the relative bioavailability of GHB sodium salt after PO administration was calculated. The values of relative bioavailability were expressed as the ratio of the AUC of GHB converted from the test compounds versus the AUC of GHB sodium salt administrated via IV alone adjusted by dose. Data are shown as below in Table 4.

TABLE 4

Rat pharmacokinetic parameters of GHB sodium salt and representative compounds

|  |  | $AUC_{last}$ (h*μg/mL) | $T_{max}$ (min) | $C_{max}$ (μg/mL) | Bioavailability F (%) |
|---|---|---|---|---|---|
| GHB sodium salt @ 50 mg/kg | IV | 25.9 |  |  | 100 |
|  | PO | 6.7 | 17 | 7.6 | 26 |
| Compound 32 4-(phenoxycarbonyloxy) butanoic acid @ 89 mg/kg | PO* | 12.4 | 10 | 22.4 | 48** |
| Compound 58 (S)-4-(2-amino-3-methylbutanoyloxy) butanoic acid @ 81 mg/kg | PO* | 14.3 | 17 | 18.5 | 55** |
| Compound 67 (S)-4-(2-acetamido-3-methylbutanoyloxy) butanoic acid @ 97 mg/kg | PO* | 7.4 | 10 | 11.1 | 29** |
| Compound 64 4-(2-isobutyramidoacetoxy) butanoic acid @ 92 mg/kg | PO* | 11.8 | 30 | 8.6 | 45** |

Note:
*measured and calculated based on GHB,
**relative bioavailability

The in vitro GHB releasing efficiency assay employing rat/human whole blood had shown that prodrug compounds could be converted to GHB with variable releasing efficiencies, which suggested that they would be converted into GHB in the systemic circulation after being administered to rat/human.

Example 3: Pharmacokinetic Studies

For rat pharmacokinetic studies, male Sprague-Dawley rats were housed individually and fasted overnight before For dog pharmacokinetic studies, male Beagle dogs were housed individually. Dogs in oral administration groups were fasted overnight before use but with free access to water supply. Dogs in IV groups have free access to food and water. The animal dosing experiments were carried out in accordance with the National Institutes of Health Guide to the Care and Use of Laboratory Animals and the Animal Welfare Act. For GHB sodium salt, a single dose of 20 mg/kg was administered to each dog in two groups (n=3/group) via intravenous (IV) administration. The vehicle used for GHB sodium salt is saline. For other test compounds, a single dose of each test compound was administered to each dog orally (n=3/group). The dosage of each test compound is listed in the Table 5. The vehicle used for dosing test compounds was 0.5% (w/v) Sodium Carboxyl Methyl Cellulose (CMC-Na) in saline. Blood samples were collected at specified time-points (pre-dose, 5 min, 10 min, 20 min, 30 min, 45 min, 1 h, 2 h, 3 h, 4 h, post-dose) following administration to individual dogs within IV and PO group. Blood samples were clotted on ice immediately, plasma samples were then isolated by centrifugation and stored frozen (−80° C.) until further analysis. The concentrations of GHB and all other test compounds were individually determined by LC/MS/MS assay. Various pharmacokinetic parameters were calculated using Phoenix™ WinNonlin® software. To quantify the bioconversion efficiency of the test compounds in the circulation system, the bioavailability of GHB sodium salt after PO administration was calculated. Data are shown as below in Table 5.

TABLE 5

Dog pharmacokinetic parameters of GHB sodium salt and representative compound

|  |  | $AUC_{last}$ (h*µg/mL) | $T_{max}$ (min) | $C_{max}$ (µg/mL) | Bioavailability F (%) |
|---|---|---|---|---|---|
| GHB sodium salt @ 20 mg/kg | IV | 35.652 |  |  | 100 |
| Compound 58 (S)-4-(2-amino-3-methylbutanoyloxy) butanoic acid @ 32 mg/kg | PO* | 17.866 | 13 | 32.4 | 51** |

Note:
*measured and calculated based on GHB,
**relative bioavailability

Example 4: Colonic Absorption in Rat

The purpose of the colonic absorption trial is to evaluate the effect of the improved transport properties of prodrugs on the resulting pharmacokinetics and distribution of GHB. The study is to be conducted by the following general procedures: GHB and the compounds of the present invention are each administered to groups of three to seven male rats through a bolus injection directly into the colon via the indwelling cannula. Following dosing, blood samples are obtained at intervals over 24 hours and are immediately processed to obtain the plasma at 4° C. The concentrations of GHB and all other test compounds are individually determined by HPLC-MS/MS assay. The compounds of the present disclosure demonstrate more effective colonic absorption than GHB.

While the present disclosure has been particularly shown and described with reference to specific embodiments (some of which are preferred embodiments), it should be understood by those skilled in the art that various changes in form and detail may be made therein without departing from the spirit and scope of the present disclosure as disclosed herein.

What is claimed is:

1. A pharmaceutical formulation comprising a compound having the structure of Formula II:

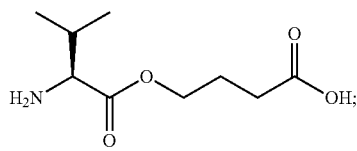

and
a pharmaceutically acceptable carrier.

2. The pharmaceutical formulation of claim 1, wherein the pharmaceutical formulation is a solid.

3. The pharmaceutical formulation of claim 1, wherein the pharmaceutically acceptable carrier comprises a solvent for dissolving or dispersing the compound.

4. The pharmaceutical formulation of claim 3, wherein the solvent comprises water.

5. The pharmaceutical formulation of claim 1, wherein the formulation is in a liquid dosage form.

6. The pharmaceutical formulation of claim 1, wherein the pharmaceutically acceptable carrier comprises a flavoring agent, sucrose, lactose, cellulose sugar, mannitol, maltitol, dextran, sorbitol, starch, agar, alginates, chitins, chitosans, pectins, tragacanth gum, gum arabic, gelatins, collagens, casein, albumin, synthetic or semi-synthetic polymers or glycerides, methyl cellulose, hydroxypropylmethyl-cellulose, or polyvinylpyrrolidone.

7. The pharmaceutical formulation of claim 1, wherein the pharmaceutically acceptable carrier comprises a polymeric excipient.

8. The pharmaceutical formulation of claim 1, wherein the formulation comprises a tablet, a caplet, a capsule, a gel cap, granules, a pill, a powder, a lozenge, a sachet, a cachet, a suspension, an emulsion, a solution, a slurry, or a syrup.

9. The pharmaceutical formulation of claim 1, wherein the pharmaceutical formulation is formulated in a unit dosage form.

10. The pharmaceutical formulation of claim 9, wherein the unit dosage form has a weight from 0.5 grams to 30 grams.

11. The pharmaceutical formulation of claim 10, wherein the pharmaceutical formulation is in a liquid dosage form.

12. The pharmaceutical formulation of claim 11, further comprising a pH adjusting agent selected from sodium hydroxide, hydrochloric acid, or malic acid.

13. The pharmaceutical formulation of claim 1, wherein the pharmaceutical formulation is formulated in a form comprising a quick release form.

14. The pharmaceutical formulation of claim 1, wherein the pharmaceutical formulation is formulated in a form comprising a delayed release form.

15. The pharmaceutical formulation of claim 1, wherein the pharmaceutical formulation is formulated in a form comprising a sustained-release form.

16. A kit comprising:
the pharmaceutical formulation of claim 1; and
instructions for administering the pharmaceutical formulation orally to a subject.

17. The kit of claim 16, wherein the pharmaceutical formulation is an oral solution.

18. A method of treating a subject in need thereof, wherein the method comprises administering to the subject a pharmaceutically effective amount of a compound having the structure of Formula II:

Formula II

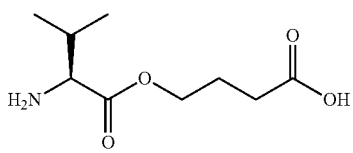

wherein the subject suffers from a disease or condition selected from narcolepsy, excessive daytime sleepiness, cataplexy, fibromyalgia, chronic fatigue, or tardive dyskinesia.

19. The method of claim 18, wherein the disease or condition is narcolepsy.

20. The method of claim 18, wherein the disease or condition is excessive daytime sleepiness.

21. The method of claim 18, wherein the disease or condition is cataplexy.

22. The method of claim 18, wherein administering to the subject the pharmaceutically effective amount of the compound comprises administering the compound no more than one time per day.

23. The method of claim 18, wherein administering to the subject the pharmaceutically effective amount of the compound comprises administering the compound orally, nasally, intravenously, subcutaneously, or intramuscularly.

24. The method of claim 23, wherein administering to the subject the pharmaceutically effective amount of the compound comprises administering the compound orally.

25. The method of claim 24, wherein administering the compound orally comprises administering the compound in an emulsion, syrup, elixir, suspension, slurry, or solution.

26. The method of claim 25, wherein administering the compound orally comprises administering the compound in a solution.

27. The method of claim 18, wherein administering to the subject the pharmaceutically effective amount of the compound comprises administering from 0.5 grams to 30 grams of the compound.

28. The method of claim 18, wherein administering to the subject the pharmaceutically effective amount of the compound comprises administering a quick-release form comprising the compound.

29. The method of claim 18, wherein administering to the subject the pharmaceutically effective amount of the compound comprises administering a sustained-release form comprising the compound.

30. The method of claim 18, wherein administering to the subject the pharmaceutically effective amount of the compound comprises administering a delayed-release form comprising the compound.

* * * * *